US011568956B2

(12) United States Patent
Barden et al.

(10) Patent No.: US 11,568,956 B2
(45) Date of Patent: Jan. 31, 2023

(54) METHODS FOR IDENTIFYING INHIBITORS OF AMYLOID PROTEIN AGGREGATION

(71) Applicant: Treventis Corporation, Bryn Mawr, PA (US)

(72) Inventors: Christopher J. Barden, Toronto (CA); Michael D. Carter, Toronto (CA); Donald F. Weaver, Halifax (CA)

(73) Assignee: Treventis Corporation, Bryn Mawr, PA (US)

( * ) Notice: Subject to any disclaimer, the term of this patent is extended or adjusted under 35 U.S.C. 154(b) by 1058 days.

(21) Appl. No.: 16/172,289

(22) Filed: Oct. 26, 2018

(65) Prior Publication Data

US 2019/0050526 A1 Feb. 14, 2019

Related U.S. Application Data

(60) Continuation of application No. 15/155,643, filed on May 16, 2016, now abandoned, which is a continuation of application No. 13/872,234, filed on Apr. 29, 2013, now abandoned, which is a division of application No. 12/549,851, filed on Aug. 28, 2009, now abandoned.

(60) Provisional application No. 61/092,845, filed on Aug. 29, 2008, provisional application No. 61/092,826, filed on Aug. 29, 2008.

(51) Int. Cl.
| | |
|---|---|
| *G01N 33/48* | (2006.01) |
| *G01N 33/50* | (2006.01) |
| *G16B 15/30* | (2019.01) |
| *G16B 15/00* | (2019.01) |
| *G16B 35/00* | (2019.01) |
| *G16C 20/60* | (2019.01) |
| *G16C 20/64* | (2019.01) |

(52) U.S. Cl.
CPC ............ *G16B 15/30* (2019.02); *G16B 15/00* (2019.02); *G16B 35/00* (2019.02); *G16C 20/60* (2019.02); *G16C 20/64* (2019.02)

(58) Field of Classification Search
CPC ........ G16B 15/30; G16B 15/00; G16B 35/00; G16C 20/60
See application file for complete search history.

(56) References Cited

U.S. PATENT DOCUMENTS

| 5,981,168 A | 11/1999 | Reiner et al. |
| 8,450,481 B2 | 5/2013 | Masliah et al. |
| 2007/0010573 A1 | 1/2007 | Kong et al. |

FOREIGN PATENT DOCUMENTS

WO  WO 2005/014563  2/2005

OTHER PUBLICATIONS

Masuda et al, "Small Molecule Inhibitors of alpha-Synuclein Filament Assembly", Biochemistry, 2006, vol. 45(19), pp. 6085-6094.

(Continued)

*Primary Examiner* — Russell S Negin
(74) *Attorney, Agent, or Firm* — Davidson, Davidson & Kappel, LLC

(57) ABSTRACT

Methods for identifying compounds that are inhibitors or are likely to be inhibitors of amyloid protein aggregation, as well as three-dimensional, non-crystallographic models (i.e. "pseudo-crystal structures") of amyloid aggregation utilized in the methods, are described. Means for creating the three-dimensional, non-crystallographic models (i.e. "pseudo-crystal structures") of amyloid aggregation are also described.

15 Claims, 2 Drawing Sheets

Specification includes a Sequence Listing.

(56) References Cited

OTHER PUBLICATIONS

Masuda et al, "Inhibition of a-synuclein fibril assembly by small molecules: Analysis using epitope-specific antibodies", FEBS Lett., 2009, vol. 583, pp. 787-791.
Anand et al, "The Alzheimer beta-amyloid AB1-39 dimer in an implicit solvent", J. Chem. Phys., 2008, vol. 129, pp. 195102-1-195102-7.
Rauk et al, "The chemistry of Alzheimer's disease", Chem. Soc. Rev., 2009, vol. 38, pp. 2698-2715.
Tarus et al, "Probing the Initial Stage of Aggregation of the Ab1 0-35-protein: Assessing the Propensity for Peptide Dimerization", J. Mol. Biol., 2005, vol. 345, pp. 1141-1156.
Li et al, "Contact regions in the dimer of Alzheimer beta-amyloid domain [1-28] studied by mass spectrometry", Eur. J. Mass Spectrom. (Chichester, England), 2004, vol. 10(2), abstract.
Massi et al, "Simulation study of the structure and dynamics of the Alzheimer's amyloid peptide congener in solution", Biophys. J., 2001, vol. 80, pp. 31-44.
Tjernberg et al, A molecular model of Alzheimer amyloid beta-peptide fibril formation, J. Biol. Chem., 1999, vol. 274 (18), pp. 12619-12625.
Morais-De-Sa et al, The crystal structure of transthyretin in complex with diethylstilbestrol: a promising template for the design of amyloid inhibitors, J. Biol. Chem., 2004, vol. 279(51), pp. 53483-53490.
Peterson et al, "Inhibiting transthyretin conformational changes that lead to amyloid fibril formation", Proc. Natl. Acad. Sci. USA, 1998, vol. 95, pp. 12956-12960.
Tartaglia et al, "Prediction of Aggregation-Prone Regions in Structured Proteins", J. Mol. Biol., 2008, vol. 380, pp. 425-436.
Riviere et al, "Inhibitory activity of stilbenes on Alzheimer's beta-amyloid fibrils in vitro", Bioorg. Med. Chem., 2007, vol. 15, pp. 1160-1167.
Esler et al, "Activation Barriers to Structural Transition Determine Deposition Rates of Alzheimer's Disease Ab Amyloid", J. Struct. Biol., 2000, vol. 130, pp. 174-183.
Massi et al, "Energy Landscape Theory for Alzheimer's Amyloid beta-Peptide Fibril Elongation", Proteins: Structure, Function, and Bioinformatics, 2001, vol. 42, pp. 217-229.
Mukrasch et al, "Sites of Tau Important for Aggregation Populate beta-Structure and Bind to Microtubules and Polyanions", J. Biol. Chem., 2005, vol. 280(26), pp. 24978-24986.
Feng et al, "Small-molecule aggregates inhibit amyloid polymerization", Nat. Chem. Biol., 2008, vol. 4(3), pp. 197-199.
Petkova et al, "Self-Propagating, Molecular-Level Polymorphism in Alzheimer's beta-amyloid Fibrils", Science, 2005, vol. 307, pp. 262-265.
Li et al, "The early events of alpha-synuclein oligomerization revealed by photo-induced cross-linking", Protein Pept. Lett., 2006, vol. 13(4), abstract.
Krishnan et al, "Oxidative Dimer Formation Is the Critical Rate-Limiting Step for Parkinson's Disease alpha-Synuclein Fibrillogenesis", Biochemistry, 2003, vol. 42, pp. 829-837.
Iwata et al, "High-resolution Crystal Structure of beta2-Microglobulin Formed at pH 7.0", J. Biochem., 2007, vol. 142, pp. 413-419.
Schormann et al, "Tertiary structure of an amyloid iunmunoglobulin light chain protein: A proposed model for amyloid fibril formation", Proc. Natl. Acad. Sci. USA, 1995, 92, pp. 9490-9494.
Gazit et al, "A possible role for pi-stacking in the self-assembly of amyloid fibrils", FASEB J., 2002, vol. 16(1), pp. 77-83.
Cohen et al., "Inhibition of Amyloid Fibril Formation and Cytotoxicity by Hydroxyindole Derivatives", Biochemistry, 2006, vol. 45, pp. 4727-4735.
Porat et al, "Inhibition of Islet Amyloid Polypeptide Fibril Formation: A Potential Role for Heteroaromatic Interactions", Biochemistry, 2004, vol. 43, pp. 14454-14462.
Balasubramanian K., "Molecular orbital basis for yellow curry spice curcumin's prevention of Alzheimer's disease", J. Agric. Food Chem., 2006, vol. 54(10), abstract.
Mastrangelo et al, "High-resolution Atomic Force Microscopy of Soluble Aβ42 Oligomers", J. Mol. Biol., 2006, vol. 358(1), pp. 106-119.
Nguyen et al., "Monomer adds to preformed structured oligomers of Abeta-peptides by a two-stage dock-lock mechanism", Proc. Natl. Acad. Sci. USA, 2007, vol. 104, pp. 111-116.
Luhrs et al, "3D structure of Alzheimer's amyloid-beta(1-42) fibrils", Proc. Natl. Acad. Sci. USA, 2005, vol. 102, pp. 17342-17347.
Ulmer et al, "Structure and dynamics of micelle-bound human alpha-synuclein", 2005, J. Biol. Chem., vol. 280, abstract, deposit PDB 10: 1XQ8 (www.pdb.org).
Glabe et al, "Common structure and toxic function of amyloid oligomers implies a common mechanism of pathogenesis", Neurology, vol. 66, pp. S74-S78.
Schwarzman et al, "Transthyretin sequesters amyloid beta protein and prevents amyloid formation", Proc. Natl. Acad. Sci. USA, vol. 91, pp. 8368-8372.
Townsend et al, "Effects of secreted oligomers of amyloid beta-protein on hippocampal synaptic plasticity: a potent role for trimers", J. Physiology, 2006, vol. 572, pp. 477-492.

METHODS FOR IDENTIFYING INHIBITORS OF AMYLOID PROTEIN AGGREGATION

CROSS-REFERENCE TO RELATED APPLICATIONS

This application is a continuation of U.S. patent application Ser. No. 15/155,643, filed on May 16, 2016, which is a continuation of U.S. patent application Ser. No. 13/872,234, filed on Apr. 29, 2013, which is a divisional of U.S. patent application Ser. No. 12/549,851, filed on Aug. 28, 2009, which claims priority to U.S. Provisional Application No. 61/092,826, filed on Aug. 29, 2008, the contents of which are hereby incorporated by reference in their entirety.

FIELD OF THE INVENTION

This invention relates to methods of identifying compounds that are inhibitors or are likely to be inhibitors of amyloid protein aggregation, and three-dimensional, non-crystallographic, models of amyloid receptors and models of amyloid protein aggregation utilized in the methods.

BACKGROUND OF THE INVENTION

The build-up of amyloid proteins in living tissue, a condition known as amyloidosis, is either the cause or a major factor in the pathology of many so-called "amyloid diseases." e.g., Alzheimer's, Parkinson's. Huntington's, and prion diseases.

Certain models of beta-amyloid aggregation that exist in vitro or in vivo (rather than "virtual" (i.e. in silico)) are used for high-throughput screening to discover new compounds that modulate amyloid aggregation (Dolphin et al. 2007, ChemMedChem 2:1613-1623; Gazit, 2006, ACS Chem. Biol. 1:417-419). These existing in vitro or in vivo models however require the synthesis and/or procurement of every candidate compound, as well as the synthesis or incubation of the model systems. In addition, these existing in vitro and in vivo models do not describe a pocket in which the candidate compounds may be inserted, and as such do not furnish a means for de novo design of compounds or for improving the potency of known modulating compounds "virtually" (i.e. in silico).

Most prior work in the field of amyloid modeling focused on the structure and dynamics of aggregation, without regard to the discovery of modulating compounds (see for example Buchete, Tycho, and Hummer, 2005, J. Molec. Biol. 353:804-821, which describes the overall structure of beta-amyloid protofibrils; Luhrs et al, 2005. Proc. Natl. Acad. Sci. USA. 102:17342-17347, which verifies the singular axis of fibril addition). These works also do not describe an amyloid protein pocket for non-peptidic compound insertion nor suggest a means of modulating amyloid protein aggregation.

Mastrangelo et al. (2006. J. Molec. Biol. 358:106-119) describes a model of beta-amyloid fibrillization, consisting of two protofibrils of beta-amyloid and a pocket found between them that can be used to insert modulating, peptidic compounds. These compounds are specific modulators of beta-amyloid fibrillization and not of aggregation, which is a fundamentally different process from fibrillization.

One treatment of amyloid diseases utilizes peptides as modulators of disease targets, being amyloid proteins in this case. (Findeis et al. 1999, Biochemistry 38:6791-6800; Ghanta et al, 1996, J Biol Chem 271:29525-29528; Tjernberg, 1996, J Biol Chem 271:8545-8548; Kokkoni et al, 2006. Biochemistry 45:9906-9918). However, utilities of the peptidic compounds described in these references as drugs is doubtful. e.g., due to in vivo stability issues.

While a number of non-peptidic compound classes have been identified as inhibitors of beta-amyloid build-up, the discovery of further compound classes, as well as the further optimization of known compound classes to improve potency may be haphazard due to the lack of known crystal structures for beta-amyloid protein.

The amyloid diseases remain invariably fatal using current medical practice.

Accordingly, there exists a need for novel methods of identifying compounds that are inhibitors or are likely to be inhibitors of amyloid protein aggregation, and three-dimensional, non-crystallographic, models of amyloid receptors and models of amyloid protein aggregation which may be utilized in these methods.

Definitions

The following terms should have the following meaning whenever used in the present specification, regardless whether the use is singular or plural.

"Crystallized amyloid protein" means an amyloid protein for which a binding pocket is known.

"Uncrystallized amyloid protein" means an amyloid protein for which a binding pocket is unknown.

"Multiply anti-amyloid compound" means a compound that has activity against both a crystallized amyloid protein and an uncrystallized amyloid protein.

"Modulating amyloid aggregation" means changing the distribution of oligomers such that amyloid deposition is reduced in a subject and encompasses a process of inhibition of aggregation.

"Model" means a molecular model, which is a representation of atoms and their positions with respect to each other, substantially including such features as covalent bonds between highly interacting atoms in a molecule and/or non-covalent interactions between the atoms of two or more molecules.

"Super-model" means a model of models.

"Computer modeling program" means any program that can visualize or otherwise manipulate molecular models on a computer, preferably also featuring molecular mechanics or molecular dynamics routines.

"Interacts" means chemical interactions, especially those that result in covalent bonds being formed between atoms in a molecule and/or non-covalent bonds between the atoms of two or more molecules. If said molecules are composed of amino acid residues, it is commonly said that two residues interact when at least one atom from one residue interacts with at least one atom from the other residue.

"Non-crystallographic" means that the model was not directly obtained by the techniques of crystallography, especially X-ray crystallography.

"Candidate model" means a model of an uncrystallized amyloid protein that is to be evaluated for utility as a pseudo-crystal structure of a crystallized or uncrystallized amyloid protein and/or amyloid aggregation.

"Halogen" means fluorine, chlorine, bromine, or iodine.

"Extracting" means the step of operating the computer modeling program such that the relevant subset is highlighted, saved, and/or placed in a different workspace within the program for the purposes of manipulating the subset without reference to the rest of a model. Such a subset may be considered a model in and of itself.

"Validating" means the step of performing docking and/or quantitative structure-activity relationship (QSAR) calculations in a computer modeling program, in order to verify that a given model can generally correctly classify and/or predict the anti-amyloid activity of a set of known positive and negative controls for anti-amyloid activity. In preferred embodiments of the invention, the set is as described in the Examples below.

"Constructing" means operating a computer modeling program to instantiate an in silico representation of a given model.

"Selecting a list of candidate compounds" means choosing a set of compounds for evaluation in a model. Selection of said set may be reference to commercially available screening libraries such as Hit2Lead or Enamine, by reference to an internal list of available and/or proprietary compounds for in vitro or in silico screening, or by utilizing lead-hopping or de novo design methods.

"Iterative docking" means docking each candidate compound in turn into the model using a computer modeling program.

"Scoring" means applying formulas to obtain a score from "scoring functions" pertaining to drug-target interactions, the output of which furnishes a measurement of the degree of complementarity of the compound with respect to the pocket.

"Score cutoff" means some value, usually an absolute energy, that can be set higher or lower depending on the level of activity that is deemed to separate active from inactive, or as a reference between more active and less active.

"Improving potency" means providing a means to furnish a compound analogous to an active compound that has minor structural differences which produce a better modulating effect with respect to the target.

OBJECTS AND SUMMARY OF THE INVENTION

The invention provides methods of utilizing three-dimensional, non-crystallographic, models of amyloid aggregation to identify compounds that are inhibitors or are likely to be inhibitors of amyloid protein aggregation. It also provides three-dimensional, non-crystallographic models, of amyloid receptors and models of amyloid protein aggregation utilized in these methods, as well as methods of producing such models for these methods.

It is an object of the invention to provide three-dimensional pseudo-crystal structures of uncrystallized amyloid proteins.

It is a further object of the invention to provide virtual three-dimensional models of amyloid aggregation and methods for producing such models.

It is also an object of the invention to provide virtual three-dimensional models of amyloid aggregation, indicating pockets in which candidate anti-amyloid models may be placed.

It is another object of the invention to provide methods of constructing three-dimensional pseudo-crystal structures or models of uncrystallized amyloid proteins and of validating the models to verify that the structures can classify and predict anti-amyloid activity of candidate compounds.

It is a further object of the invention to provide methods of utilizing the three-dimensional pseudo-crystal structures or models to identify compounds that modulate or are likely to modulate amyloid aggregation.

It is an additional object of the invention to provide methods of improving the anti-amyloid potency of candidate compounds.

It is a further object of the invention to provide methods of predicting potential interactions between candidate compounds and amyloid proteins.

It is also an object of the invention to provide methods for identification and characterization of previously unknown binding pockets or conformational regions of amyloid proteins.

It is yet another object of the invention to use compound identified or improved using the methods of the invention as therapies for diseases in which amyloidosis occurs.

DETAILED DESCRIPTION

Figure 1:
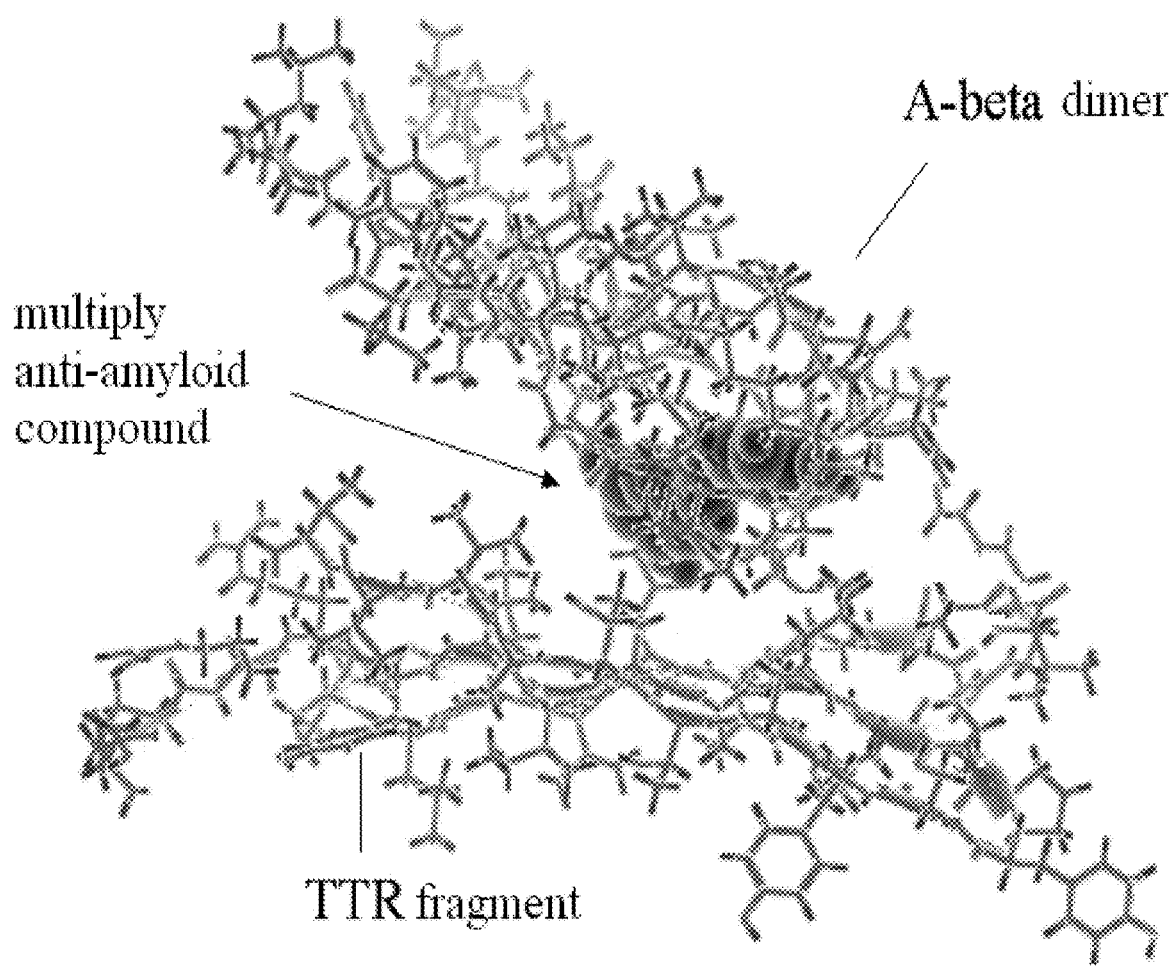
FIG. 1 is a depiction of the super-model developed in Example 1, in which the crystallized amyloid protein is a fragment of transthyretin, the multiply anti-amyloid compound is resveratrol, and the uncrystallized amyloid protein is a dimer of $A\beta_{17\text{-}42}$.

Amyloidosis refers to a variety of conditions in which amyloid proteins are abnormally deposited in organs and/or tissues.

Certain types of amyloidosis occur principally in the central nervous system. e.g., with aggregation of beta-amyloid protein in Alzheimer's Disease, alpha-synuclein in Parkinson's Disease, huntingtin protein in Huntington's Disease, and prion protein in Creutzfeldt-Jacob and other prion diseases. Other types of amyloidosis are systemic in nature, as, e.g., with aggregation of transthyretin in senile systemic amyloidosis.

Historically, aggregations of protein were classified as "amyloid" if they displayed apple-green birefringence under polarized light when stained with the dyes Congo red or Thioflavin T (ThT) (Sipe and Cohen, 2000, J. Struct. Biol. 130:88-98). That definition of "amyloid protein" has been expanded in recent years to apply to any fibrous structure which is ordered and insoluble, and which is composed of fibrils of approximately 10 nm in width and up to several microns in length (Zheng, Ma. and Nussinov, 2006. Phys. Biol. 3:P1-P4).

An "amyloidogenic" polypeptide is one which, regardless of sequence, can polymerize in a cross-β sheet conformation in vitro or in vivo to form amyloid protein (Xu, 2007, Amyloid 14:119-31). "Amyloidogenic" polypeptides include. e.g., amyloid light chain, amyloid associated protein, β amyloid, transthyretin, $\beta_2$ microglobulin, amylin, prion related protein, and other amyloid proteins.

All amyloid proteins have commonalities. However, whether certain amyloid proteins are related depends on the amyloid proteins having commonality of both pathology and location. For example, beta-amyloid protein and huntingtin protein are both located in a human brain, but their divergence in pathology is sufficient to consider them unrelated. Beta-amyloid protein, tau protein, and alpha-synuclein protein on the other hand are related, all being located in the human brain and being thought to have overlapping roles in the pathology of neurodegenerative diseases, e.g., Alzheimer's disease and Parkinson's disease. Nevertheless, given the preponderance of non-peptidic anti-amyloid compounds that inhibit aggregation of more than one amyloid protein, it is reasonable to assume that models of amyloid protein aggregation provided by the present invention will have significant utility even with unrelated amyloid proteins, in addition to having utility with the related amyloid proteins (i.e., beta-amyloid protein, tau protein, and alpha-synuclein protein).

A lock and key analogy is commonly used to characterize drug-target interactions where a specific "key" (compound/drug) interacts only with its respective molecular "lock" (target/receptor). An appropriate degree of shape and electronic complimentarily between the drug and target must occur to produce drug-target interactions which are necessary for a pharmacological response. The specific location on the "lock" or target is often referred to as the active or catalytic site, and the intuitive shape of the active site is that of a pocket. Thus a "binding pocket," or more simply "pocket." is used in the art to refer to that space on the target in which a molecule can be inserted to modulate activity of the target. The three-dimensional shape and electronic properties of the pocket form the basis for rational drug design and for virtual screening techniques (e.g., in silico) utilized in the methods of the present invention, provides means for identifying the pocket for non-peptidic compound insertion and suggests means for modulating amyloid protein aggregation.

"Rational drug design" attempts to formulate drug design hypotheses that specify and optimize the physical contacts between a drug and its target, often by aid of a computer. Such "computer-aided drug design" generally depends on high resolution, three-dimensional models of the target, and such models are usually constructed by X-ray crystallography of a crystal form of the target. Crystallographic techniques are the primary means of obtaining three-dimensional structure and binding information in the art. In the absence of a solved, high-resolution (i.e. below 2 angstroms) crystal structure of a given amyloid protein indicating the binding mode of an anti-amyloid compound and/or the chemical interactions essential to aggregation, rational design of anti-amyloid compounds for said protein was generally considered haphazard and difficult prior to the methods and models of the present invention.

The virtual screening techniques utilized in the methods of the present invention and the virtual models of the present invention allow, e.g., for the virtual identification of the binding pockets of amyloid proteins, and construction of three-dimensional non-crystallographic models of amyloid receptors and models of amyloid aggregation. The methods of the present invention generally do not require construction of crystal forms of the target by X-ray crystallography, and instead provide or utilize non-crystallographic models ("pseudo-crystal structures") that could approximate or exceed the utility of traditional crystal structures.

Candidate Models

The invention provides for candidate models of amyloid receptors and of amyloid protein aggregation to be constructed, evaluated and subsequently validated. The models of the present invention are based, in part, both on the symmetry inherent in many anti-amyloid compounds and on the multi-target activity of such compounds.

The models of the present invention may be referred to as "pseudo-crystal structures" or as surrogate models, as the models are not obtained by the technique of crystallography. As stated above and as demonstrated by the examples below, the utility of "pseudo-crystal structures" of the present invention may approach and exceed that of crystal structures.

Successful candidate models (e.g., pseudo-crystal structures) will include elements directly related to the process of aggregation and will be of sufficient detail to enable the design of compounds for disrupting or otherwise altering the interactions essential to amyloid protein aggregation. Indeed, if a pseudo-crystal structure does not indicate the binding mode of an anti-amyloid compound and/or the chemical interactions essential to aggregation, then it is not a proper model of amyloid protein aggregation and would not be expected to have utility to enable the design of anti-amyloid compounds.

Successful candidate models in accordance with the present invention may comprise pseudo-crystal structures of uncrystallized amyloid proteins. Such pseudo-crystal structures generally comprise two parts. The first part generally comprises an amyloid monomer, and the second part generally comprises an amyloid monomer or an amyloid oligomer. The first part is generally positioned with respect to the second part such that it forms a pocket in conjunction with the second part, such that a candidate compound may be inserted into the pocket, thereby potentially modulating amyloid aggregation.

The amyloid monomer comprises one peptide chain from an amyloid oligomer or amyloid protein. The amyloid monomer in the first part and the amyloid monomer (or each monomer in an amyloid oligomer) in the second part may comprise the same sequence or different sequences with respect to the first part.

The amyloid oligomer comprises a heterogeneous or homogeneous link comprising an amyloid protein (or amyloidogenic fragments thereof). For example, in certain embodiments, the amyloid oligomer comprises an amyloid protein (e.g., either beta-amyloid protein, tau protein, alpha-synuclein protein, huntingtin protein, or prion protein) or amyloidogenic fragments thereof; and in other embodiments the amyloid oligomer comprises two or more amyloid proteins (e.g., a combination of beta-amyloid protein and tau protein, a combination of beta-amyloid protein and alpha-synuclein protein, etc.) or amyloidogenic fragments thereof. The amyloid oligomer may also comprise a protein which has not yet shown to be amyloidogenic or a portion of such protein.

In certain embodiments, the amyloid oligomer or amyloidogenic fragment thereof comprises a region comprising approximately residues 17 through 40 of beta-amyloid protein of length 40; approximately residues 17 through 42 of beta-amyloid protein of length 42; approximately residues 1 through 15 of alpha-synuclein protein; approximately residues 25 through 40 or 275 through 280 of tau protein;

approximately residues 90 through 110 of the major prion precursor protein; or approximately residues 5 through 20 of the huntingtin protein.

Figure 2:
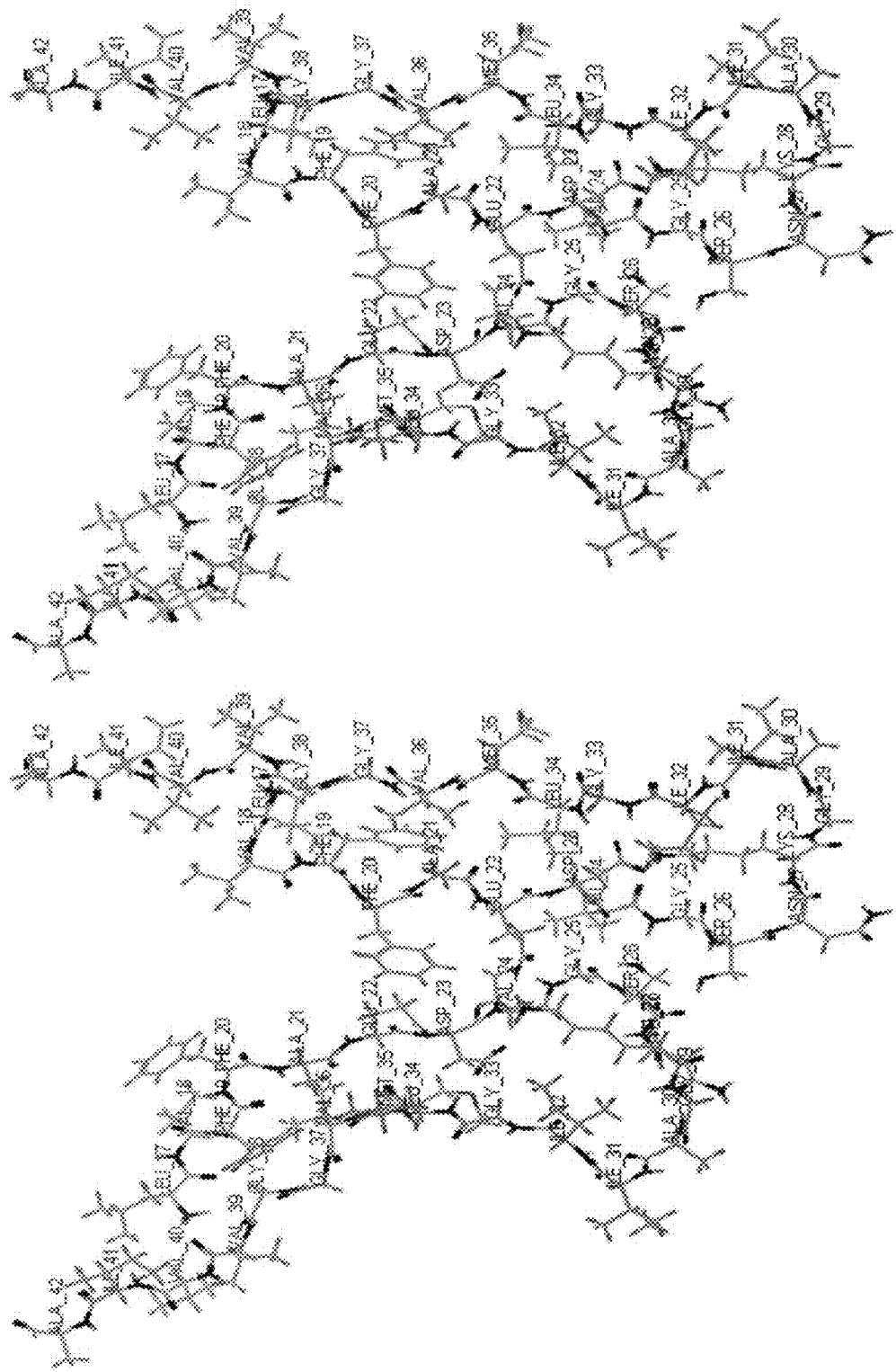
FIG. 2 is a stereographic view of the pseudo-crystal structure, a model of amyloid protein aggregation, of Example 1 with resveratrol bound in its pocket.

In certain embodiments, the model comprises the pseudo-crystal structure formed by SEQ ID: 1 and SEQ ID: 2 and interacting in the manner depicted stereographically in FIG. 2, which is a model of amyloid protein aggregation of Example 1, with resveratrol bound in its pocket. Three-dimensional features of the model may be appreciated by a person of normal binocular vision by superimposing the images visually.

In certain embodiments, the first part comprises substantially SEQ ID: 1 and the second part comprise substantially SEQ ID: 2, wherein SEQ ID: 1 is

```
Leu Val Phe Phe Ala Glu Asp Val Gly Ser Asn
1                   6                    11

Lys Gly Ala Ile Ile Gly Leu Met Val Gly Gly
    Val
                16                   21

Val Ile Ala
        26
``` and,
SEQ ID: 2 is

```
Leu Val Phe Phe Ala Glu Asp Val Gly Ser Asn
1                   6                    11

Lys Gly Ala Ile Ile Gly Leu Met Val Gly Gly
    Val
                16                   21

Val Ile Ala
        26
```

In certain embodiments, the first part is further positioned with respect to the second part such that the amino acid Val at position 8 of SEQ ID: 1 interacts with the amino acid Glu at position 6 of SEQ ID: 2; the amino acid Gly at position 9 of SEQ ID: 1 interacts with the amino acid Glu at position 6 of SEQ ID: 2; the amino acid Ser at position 10 of SEQ ID: 1 interacts with the amino acid Gly at position 9 of SEQ ID: 2; the amino acid Ser at position 10 of SEQ ID: 1 interacts with the amino acid Ser at position 10 of SEQ ID: 2; and the amino acid Lys at position 12 of SEQ ID: 1 interacts with the amino acid Glu at position 6 of SEQ ID: 2.

In certain embodiments, the first part is positioned with respect to the second part in the orientation shown in FIG. 2. FIG. 2 is a stereographic view of the pseudo-crystal structure, a model of amyloid protein aggregation, of Example 1 with resveratrol bound in its pocket. The model of FIG. 2 features two $A\beta_{17\text{-}42}$ monomers bound to each other near the N terminals in a "double candycane" structure. Each monomer is folded in a loop from residues 23 through 33, which is a conformation well supported by electron microscopy and NMR spectroscopy. The loops are stabilized by intra-loop cationic-anionic interactions between $Asp_{23}$ and $Lys_{28}$, and they also show an inter-loop attraction through these same residues. Short-run (up to 100 ns) molecular dynamics calculations on this model indicate that the pocket is stable.

In certain embodiments, a virtual non-crystallographic model of amyloid protein aggregation comprises a pseudo-crystal structure comprising a three-dimensional model of an uncrystallized monomeric amyloid protein and a three-dimensional model of an uncrystallized amyloid protein comprising one or more amyloid peptides; said three-dimensional model of an uncrystallized amyloid protein is positioned with respect to said amyloid monomer model such that it forms a pocket in conjunction with said amyloid monomer model, such that a candidate compound may be inserted into said pocket thereby, e.g., potentially modulating amyloid aggregation.

Aggregation is a fundamentally different process from fibrillization. Aggregation occurs among monomers and oligomers of incipient amyloid protein, while fibrillization is directed to the further lengthening of pre-formed amyloid protofibrils and subsequent assembly into fibrils. Modulators of aggregation are preferred to modulators of fibrillization for treatment of amyloid diseases, since soluble oligomers of beta-amyloid protein are thought to be the pathogenic species in Alzheimer's Disease, rather than the mature fibrils thereof (Klyubin et al, 2008, J. Neurosci, 28:4231-4237; Townsend et al, 2006, J. Physiol. 572:477-492).

For clarity, it should be understood that a model of amyloid protein aggregation promulgated in the present application is substantially a model of addition of monomeric amyloid peptide to an amyloid oligomer or an amyloid protein. In certain embodiments, the monomeric amyloid peptide and the amyloid oligomer (or the amyloid protein) is composed of chains of different amyloid peptides. In other embodiments, the monomeric amyloid peptide and the amyloid oligomer or protein are composed of chains of the same amyloid peptide.

In certain embodiments of the invention, modulating amyloid aggregation may result in greatly increasing the proportion of amyloid peptide assemblies with size n, where n is between 1 and 10. In other embodiments, modulating amyloid aggregation may result in increasing the proportion of amyloid peptide assemblies with size n, where n is between 1 and 5. In still other embodiments of the invention, modulating amyloid aggregation may result in increasing the proportion of amyloid peptide monomer (i.e. where n is only 1).

In certain embodiments, a virtual non-crystallographic model of amyloid protein aggregation comprises a pseudo-crystal structure comprising an amyloid monomer model and a three-dimensional model of an uncrystallized amyloid protein. The "amyloid protein" in the minimal case may comprise only one amyloidogenic peptide having substantially the same sequence as an amyloid protein or an amyloidogenic fragment thereof. The "amyloid protein" may also comprise a plurality of chains of one amyloid protein or amyloidogenic portions thereof, and does not include other amyloid protein or amyloidogenic portions thereof. In certain embodiments, the plurality of chains are aggregated according, e.g., to a building-up principle.

In certain embodiments, the amyloid monomer model and the three-dimensional model of an uncrystallized amyloid protein are both composed of beta-amyloid protein or an amyloidogenic fragment thereof. For example, the amyloids may comprise substantially the sequence of beta-amyloid 1-42 and/or the sequence of beta-amyloid 1-40 and/or the sequence of the beta-amyloid fragment 25-35 and/or the sequences of beta-amyloid fragment 17-42, which are sequences known to form aggregated beta-amyloid (Hughes et al. 2000, J Biol Chem 275:25109-25115).

In certain embodiments, candidate models of amyloid protein aggregation comprise a pseudo-crystal structure comprising a three-dimensional model of an uncrystallized, monomeric amyloid protein and a three-dimensional model of an uncrystalized amyloid protein comprising one or more amyloid peptides positioned with respect to the monomeric amyloid protein model such that it forms a pocket in conjunction with the monomeric amyloid protein. In one embodiment, the monomeric amyloid model is substantially SEQ ID: 1; and the amyloid protein model comprises SEQ ID: 2.

In certain embodiments three-dimensional, non-crystallographic models, of amyloid aggregation comprise pseudo-crystal structures for amyloid proteins that lack extant crystal structures (e.g., beta-amyloid protein, tau, alpha-synuclein, huntingtin, and prion protein, etc.).

In certain embodiments of the invention, a model may be recorded in a mathematical form using a combination of atomic information and three-dimensional coordinates (e.g. in the PDB format, or in the proprietary format of a computer modeling program), which are then visualized or otherwise represented virtually, e.g., in a computer modeling program. In certain embodiments, the model reflects the likely protonation state at physiological pH such that basic moieties of the model are protonated and acidic moieties are deprotonated in a manner consistent with valence considerations. In further embodiments, force fields and charges are applied appropriate to the model such that molecular mechanics and/or dynamics can be used; details on these and other computational techniques characteristically found in computer modeling programs are described, e.g., in A. Leach, Molecular Modeling: Principles and Applications, $2^{nd}$ edition, Prentice Hall, 2001, herein incorporated by reference.

The models of the present invention may, e.g., enable the identification of new chemical classes of modulators of their respective amyloid protein and related amyloid proteins. For example, if a candidate compound has a three-dimensional shape and electronic properties that will allow it to "fit" into the pseudo-crystal structure and interact with the pseudo-crystal structure, it is likely to be a potential modulator of the amyloid protein aggregation.

The models of the present invention may also provide a means of improvement in potency for compounds known to have modulating effects on a relevant amyloid protein, as they may suggest structural modification to the compounds known to have modulating effects on the amyloid protein, to allow the compounds to better "fit" and interact with the three-dimensional pseudo-crystal structure. They may also provide means to the de novo design of compounds which may "fit" into the three-dimensional structure.

The models may further provide means for the identification and discovery of the compounds which may be useful in modulation of either or both aggregation and fibrillization.

Construction of Models

The present invention further provide means for constructing surrogate models (i.e., non-crystallographic virtual models) of amyloid protein aggregation which may be used for drug design much as crystal structures are customarily used but at a lower cost and without a need for synthesis of every candidate compound.

For example, the three-dimensional, non-crystallographic models of amyloid aggregation models in accordance with the present invention may be constructed. e.g., virtually (e.g., in a computer modeling system), depicted pictorially, instantiated in a physical form by way of a modeling kit, or visualized mentally. The virtual modeling afforded by the present invention allows for greatly reduced cost and labor as compared to in vitro or in vivo systems, as it does not require the synthesis and/or procurement of every candidate compound. In particular, it allows for the screening and prediction of the anti-amyloid properties of a candidate compound based on its three-dimensional shape and electronic configuration, even before the compounds are synthesized. It disposes of a potentially great number of candidate compounds which will not "fit" into the three-dimensional, non-crystallographic, models of the amyloid aggregation afforded by the present invention, and are therefore are unlikely to have anti-amyloid activity.

Generally, construction of the non-crystallographic models is performed manually, using a molecule or peptide/biomolecule building routine as included in a computer modeling program. In some embodiments of the invention, construction may proceed automatically through the reading of a previously constructed file or sequence.

In certain embodiments, the invention provides means for constructing virtual non-crystallographic models of amyloid aggregations for proteins for which the three-dimensional structure and binding information (e.g., binding mode and chemical interactions essential for aggregation) are known. In other embodiments, the invention provides means for constructing virtual non-crystallographic models of amyloid aggregations for proteins for which the three-dimensional structure and binding information (e.g., binding mode and chemical interactions essential for aggregation) are unknown. In certain embodiments, the means for constructing virtual non-crystallographic models of amyloid aggregations for proteins for which the three-dimensional structure and binding information are known and the means for constructing virtual non-crystallographic models of amyloid aggregations for proteins for which the three-dimensional structure and binding information are unknown are the same.

In certain embodiments, a pseudo-crystal structure of an uncrystallized amyloid protein can be virtually identified and constructed by manipulating a computer program to orient an uncrystallized amyloid protein and/or oligomer such that a pocket is formed around a multiply anti-amyloid compound already bound in the crystallized amyloid protein. The pocket has a particular three-dimensional shape and electronic properties and represents, e.g., a pseudo-crystal structure of the uncrystallized amyloid protein. In certain embodiments, the multiply anti-amyloid compound is removed and is not part of the pseudo-crystal structure. In other embodiments, the multiply anti-amyloid compound is part of the pseudo-crystal structure.

In certain embodiments, a binding pocket corresponds to a common conformational region on a variety of amyloid proteins, e.g., the Common Conformational Motif (CCM). For example, the CCM may correspond to a conformational region found in both Aβ and tau; or a conformational region found in both Aβ and alpha-synuclein; or a conformational region found in both Aβ and transthyretin. The conformational region may also be common to Aβ, tau and alpha-synuclein (which are all located in the human brain and being thought to have overlapping roles in the pathology of neurodegenerative diseases). The binding pocket may therefore be useful for the identification of candidate compounds which are likely to inhibit the aggregation of several amyloid proteins simultaneously (e.g., Aβ and tau; Aβ and alpha synuclein; Aβ, tau and alpha synuclein, etc.). It should be understood for this reason that the CCM is not strictly sequence-dependent.

In certain embodiments, a method of creating pseudo-crystal structures of uncrystallized amyloid protein receptor comprises (1) applying molecular mechanics and/or dynamics to a three-dimensional super-model comprising a crystallized amyloid protein model, a model of multiply anti-amyloid compound bound in the pocket of the crystallized amyloid protein or oligomer, and a candidate model of an uncrystallized amyloid protein, such that a pocket on the uncrystallized amyloid protein or oligomer is formed around the multiply anti-amyloid compound; (2) extracting said uncrystallized amyloid protein model from said super-model; and (3) validating said uncrystallized amyloid protein model with respect to experimental data so as to confirm its utility as a pseudo-crystal structure. In certain embodiments, the extracted model comprises the multiply anti-amyloid compound. In other embodiments, the extracted model is free of the multiply anti-amyloid compound.

Example 1 below describes an exemplary method for construction of one pseudo-crystal structure of beta-amyloid protein in accordance with one embodiment of the invention. In the method of Example 1, the uncrystallized amyloid protein is an amyloidogenic fragment of beta-amyloid protein, the crystallized amyloid protein is transthyretin protein, and the multiply anti-amyloid compound is resveratrol. In particular, the pseudo-crystal structure of Example 1 has two parts: one monomer of an amyloidogenic beta-amyloid fragment (i.e. the "amyloid monomer"); and another monomer of an amyloidogenic beta-amyloid fragment, which could have multiple additional peptides attached thereon without disrupting its interaction with the amyloid monomer (as such, this second part is sometimes referred to as the "amyloid oligomer", as it is only contingently monomeric).

In certain embodiments, the invention provides a method of constructing pseudo-crystal structures of uncrystallized amyloid protein which are models of amyloid protein aggregation. This method's first step is to apply molecular mechanics and/or dynamics to a three-dimensional super-model comprising a crystallized amyloid protein model, a model of multiply anti-amyloid compound bound in the pocket of the crystallized amyloid protein, and a candidate model of an uncrystallized amyloid protein or oligomer, such that a pocket on the uncrystallized amyloid protein is formed around the multiply anti-amyloid compound.

The method's second step is to extract said uncrystallized amyloid protein or oligomer model from the super-model. In certain embodiments, the extracted model comprises the multiply anti-amyloid compound. In other embodiments, the extracted model is free of the multiply anti-amyloid compound.

The method's third step is to validate said uncrystallized amyloid protein model with respect to experimental data so as to confirm its utility as a pseudo-crystal structure.

The crystallized amyloid protein may be transthyretin, islet amyloid polypeptide, beta-2-microglobulin, and insulin protein; and the uncrystallized amyloid protein may be either of beta-amyloid, tau, alpha-synuclein, huntingtin, or prion protein; an amyloidogenic fragment of any of the foregoing, or composed of a heterogeneous combination of such proteins.

A multiply anti-amyloid compound may be resveratrol, or a compound having low energy conformations that overlap geometrically and electrostatically with resveratrol. In certain embodiments, a multiply anti-amyloid compound is a compound selected from the lists of compounds provided in paragraphs [00106] to [0117] of the present application.

Once a model (i.e., a pseudo-crystal structure) is constructed, it is then extracted and validated with respect to experimental data to verify that it can classify and predict, e.g., the anti-amyloid activity of candidate compounds. In certain embodiments, validation comprises performing docking and/or quantitative structure-activity relationship (QSAR) calculations in a computer modeling program, in order to verify that a given model can generally correctly classify and/or predict the anti-amyloid activity of a set of known positive and negative controls for anti-amyloid activity. Examples of computer modeling programs include but are not limited to MOE, Sybyl, Cerius$^2$, CHARMm, DOCK, AUTODOCK, GLIDE, and FlexX.

Manuals of these computer modeling programs are herein incorporated by reference in their entirety.

Example 2 below describes an exemplary method for validating an exemplary of amyloid protein aggregation.

Once validated, the resulting pseudo-crystal structure can be used as a three-dimensional, non-crystallographic, model of amyloid aggregation in the methods of the present invention.

THE METHODS OF THE INVENTION

The methods of the invention may be used to identify or improve the potency of candidate compounds that are anti-amyloid with respect to the amyloid protein or fragment thereof depicted in a particular three-dimensional, non-crystallographic, model, or is related to the amyloid protein or fragment thereof that is depicted in the model. The methods of the invention may also be used to identify, or improve the potency of, compounds that are anti-amyloid with respect to an amyloid protein or fragment thereof that is unrelated to the amyloid protein or fragment thereof that is depicted in a particular three-dimensional non-crystallographic model.

In certain embodiments, the methods of the present invention utilize the "virtual" non-crystallographic models to identify new compounds which may be inhibitors or likely to be inhibitors of amyloid protein aggregation, as well as improve existing modulators of amyloid proteins, all without the construction of crystal form of the target by X-ray crystallography.

In certain embodiments, the models are used to predict the potential interactions between a candidate compound and an amyloid protein, e.g., by allowing visualization of the candidate compound fitting into the binding pocket.

One empirical determinant for whether two atoms interact is their proximity to each other in a given chemical system. For example, a covalent bond between carbons is approximately 1.5 angstroms in interatomic distance, while a weak non-covalent bond between atoms could be as long as 3 angstroms (although stronger non-covalent bonds may approach 1.5 angstroms in length). The hydrogens in the head group of a protonated Lys residue interacting with the oxygens in the head group of a deprotonated Glu residue is an example of a primarily ionic non-covalent bond. The hydrogen in the head group of a Ser residue interacting with the carbonyl oxygen in the backbone of a different Ser residue, or a hydrogen in the backbone of a Gly residue interacting with the oxygen in the head group of a Ser residue, are examples of primarily hydrogen bonds. The virtual visualization provided by the methods of the present invention supply a means of predicting the likelihood of these interactions between a candidate model compound and a particular binding pocket. If the visualization shows that the modeling compound is unlikely to interact with a particular binding pocket on an amyloid protein, it is unlikely that the modeling compound will be useful as an inhibitor, e.g., of the amyloid protein aggregation. To the contrary, if the compound is likely to interact with the binding pocket of the amyloid aggregation, it is likely that the compound may be capable of modulating activity and potentially preventing or minimizing aggregation of this particular amyloid protein.

In the context of a pseudo-crystal structures described in the present application, one of the most important intermolecular interactions are those which hold the amyloid oligomer together as well as those which attract the amyloid monomer. The latter said interactions are pivotal to the conformation and eventual incorporation of the amyloid monomer into the amyloid oligomer, a process which is believed to continue repeatedly until reaching the critical size at which fibrillization occurs. By inserting into the pocket where these intermolecular interactions occur, the candidate compound may disrupt or otherwise alter the process of aggregation. Whether the candidate compound can do so depends, e.g., on its shape and electronic complementarity, i.e., the ability of moieties on the compound to interact with important residues in the pocket. The visualization of the fitting provided by the present invention will allow the prediction of whether the candidate compound is likely to interact with the important residues of the pocket. Other intermolecular interactions, which may be less important to describing aggregation, yet are potentially of importance in achieving the desired accuracy with respect to a given model of amyloid protein aggregation. The presently claimed methods may also have utility in predicting these other intermolecular interactions.

A common interaction within such systems involves ionic, acid-base interactions such as Lys-Glu and Lys-Asp as well as hydrogen-bonding interactions such as Ser-Ser. Therefore, regions of amyloid proteins or amyloidogenic fragments thereof that should make excellent models include but are not limited to the following: in beta-amyloid protein of length 40, approximately residues 17 through 40; in beta-amyloid protein of length 42, approximately residues 17 through 42; in alpha-synuclein, approximately residues 1 through 15; in tau protein, approximately residues 25 through 40 or approximately residues 275 through 280; in the major prion precursor protein, approximately residues 90 through 110; and in huntingtin, approximately residues 5 through 20.

Chemical interaction is a matter of degree: especially in non-covalent bonds, the type of bonding involved can often be an admixture of one or more types of bonding named above, possibly including other effects such as hydrophobic or van der Waals interactions.

Selected examples of chemical interactions which may be predicted utilizing the methods of the present invention include (but are not limited) to non-covalent bonds including, e.g., ionic, dipole-dipole, dipole-induced dipole, and hydrogen bonding.

Covalent bonds may also be predicted by the methods of the present invention. Covalent bonds are the most permanent of chemical interactions and are generally not altered by intermolecular interactions, which are governed primarily by non-covalent bonds.

In certain embodiments, the present invention provides method for identification and characterization of a previously unknown binding pocket or a conformational region of an amyloid, and subsequent utilization of the previously unknown pocket/conformational region as a screening tool for identification and optimization of anti-amyloid compounds. In these embodiments, the binding pocket is identified in silico, e.g., by using molecular modeling (especially optimization and dynamical techniques) on a "super-model" comprising a model of amyloid protein for which a binding pocket is known (a "crystallized amyloid protein"); a model of a compound (a "multiply anti-amyloid compound") that has activity against said crystallized amyloid protein, as well as having activity against an amyloid protein for which a binding pocket is unknown (an "uncrystallized amyloid protein"); and a candidate model for said uncrystallized amyloid protein. In certain embodiments, these methods further allow for the construction of a pseudo-crystal structure of beta-amyloid protein or a receptor having utility in identification and optimization of anti-amyloid compounds.

A crystallized amyloid protein may be selected, e.g., from the group consisting of transthyretin, islet amyloid polypeptide, beta-2-microglobulin, and insulin protein. In certain embodiments, the crystallized amyloid protein is transthyretin protein, or an amyloidogenic fragments thereof.

An uncrystalized amyloid protein may be selected, e.g., from the group consisting of beta-amyloid, tau, alpha-synuclein, huntingtin, and prion protein. In certain embodiments, the uncrystalized amyloid protein is beta-amyloid proteins, and amyloidogenic fragments thereof.

A multiply anti-amyloid compound may be any compound which has activity against any crystallized amyloid protein. In a preferred embodiment, the multiply anti-amyloid compound is resveratrol or an analog thereof.

In certain embodiments, the crystallized amyloid protein is selected from the group of transthyretin, islet amyloid polypeptide, beta-2-microglobulin, and insulin protein; and the uncrystallized amyloid protein is selected from the group of beta-amyloid, tau, alpha-synuclein, huntingtin, and prion protein. In certain embodiments, the crystallized amyloid protein is transthyretin protein or an amyloidogenic fragment thereof, and the uncrystallized amyloid protein is beta-amyloid protein or an amyloidogenic fragment thereof, and the multiply anti-amyloid compound is resveratrol.

The invention further encompasses and provides a method of identifying compounds that modulate amyloid aggregation. The method generally comprises the steps of constructing a pseudo-crystal structure in a computer modeling program; selecting a list of candidate compounds; constructing said candidate compounds in a computer modeling program; performing an iterative docking and scoring of all candidate compounds, by means of docking each candidate compound into the pocket formed by said model and scoring each candidate compound to reflect its degree of complementarity with respect to said pocket; and identifying compounds that modulate amyloid aggregation by reference to a score cutoff that substantially distinguishes active compounds from inactive compounds.

A candidate compound may, e.g., be a compounds of Formulas Ia, Ib, Ic, pharmaceutically acceptable salts, stereo-isomers, polymorphs, metabolites, prod-drugs, analogs and combinations of any of the foregoing:

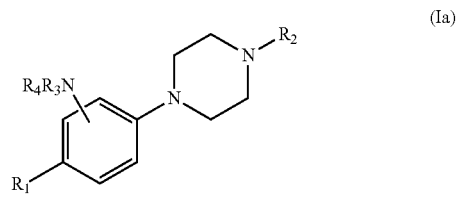

(Ia)

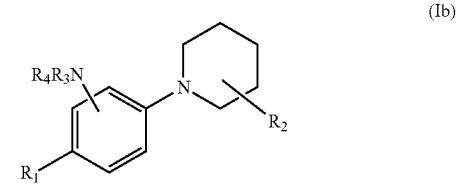

(Ib)

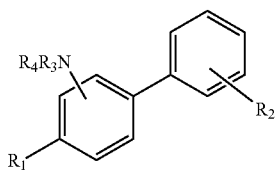

wherein

R₁ is selected from the group consisting of H, nitro, carboxylic acid, alkylcarboxylic acid, acetamide connected in either direction. N-(2-ethanol)amine, N-(2-morpholinethyl)amine, amine optionally substituted with one or more alkyl groups, amide optionally substituted with one or more alkyl groups, and alkoxy;

R₂ is selected from the group consisting of H, carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups;

R₃ is selected from the group consisting of H, alkyl, furanylalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and R₄ is selected from the group consisting of H, alkyl, or phenyl optionally substituted with any one or more halogen, alkyl, or alkoxy groups.

In certain embodiments, R₁ is selected from the group consisting of nitro, acetamide connected in either direction, N-(2-ethanol)amine, amino optionally substituted with any one or more alkyl groups, and amide optionally substituted with any one or more alkyl groups: R₂ is selected from the group consisting of carboxylic acid, amide optionally substituted with any one or more of alkyl or aryl groups, and phenonyl optionally substituted with any one or more of alkoxy, alkyl, or aryl groups; R₃ is selected from the group consisting of methyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and R₄ is selected from the group consisting of H, alkoxy, and aryl.

In other embodiments, R₁ is selected from the group consisting of nitro, acetamide connected in either direction, N-(2-ethanol)amine, amino optionally substituted with methyl or dimethyl, amide optionally substituted with methyl, ethyl, dimethyl, or diethyl, and methoxy; R₂ is selected from the group consisting of phenonyl optionally substituted with any one or more of methoxy, alkyl, or halogen, amide optionally substituted with any one or more of methyl, phenyl, benzyl, or dimethyl, and carboxylic acid; R₃ is selected from the group consisting of methyl, phenyl optionally substituted with any one or more of halogen, alkyl, or methoxy, benzyl optionally substituted with any one or more of halogen, alkyl, or methoxy, and phenonyl optionally substituted with any one or more of halogen, alkyl, or methoxy; and R₄ is selected from the group consisting of H, methyl, and phenyl optionally substituted with any one or more of halogen, alkyl, or alkoxy.

The compounds disclosed in Formulas Ia. Ib and Ic should be understood as also accommodating methyl, ethyl, methoxy, fluoro, or chloro groups at any position otherwise occupied by a ring hydrogen. Moreover, R₃ and R₄ may be used in combination to produce a nitro moiety on the phenyl ring, or to create ring systems such as morpholine, quinoline, or isoquinoline.

In certain embodiments, a candidate compound is a compound of Formula Ia, pharmaceutically acceptable salts, stereo-isomers, polymorphs, metabolites, prod-drugs and combinations thereof:

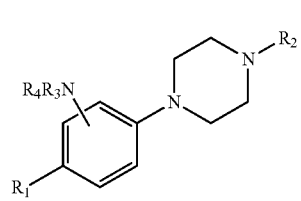

wherein the NR₃R₄ moiety is connected ortho to the R₁ moiety on the phenyl ring;

R₁ is selected from the group consisting of nitro, amino optionally substituted with methyl or dimethyl, and amide optionally substituted with methyl, dimethyl, ethyl, or diethyl;

R₂ is phenonyl optionally substituted with halogen or methoxy;

R₃ is selected from the group consisting of phenyl optionally substituted with halogen or methoxy and benzyl optionally substituted with halogen or methoxy; and R₄ is selected from the group consisting of H, methyl, and phenyl; with the following exception: when R₁ is nitro. R₄ is H, and R₃ is benzyl optionally substituted with fluoro or isopropyl.

In other embodiments, a candidate compound is a compound of Formula Ic, pharmaceutically acceptable salts, stereo-isomers, polymorphs, metabolites, prod-drugs and combinations thereof:

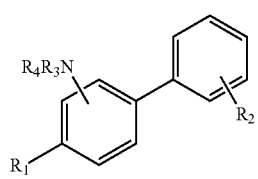

wherein the NR₃R₄ moiety is connected ortho to the R₁ moiety on the phenyl ring;

R₁ is selected from the group consisting of nitro, amino optionally substituted with methyl or dimethyl, and amide optionally substituted with methyl, dimethyl, ethyl, or diethyl; the R₂ moiety is connected meta with respect to the phenyl ring;

R₂ is carboxylic acid;

R₃ is selected from the group consisting of phenyl optionally substituted by any one or more of methoxy or halogen and benzyl optionally substituted by any one or more of methoxy or halogen; and R₄ is selected from the group consisting of H and methyl.

In additional embodiments, a candidate compound is a compound of Formula II:

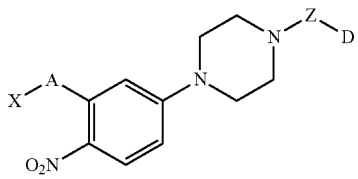

wherein

X is selected from the group consisting of hydrogen, methyl, amine, methoxy, phenyl optionally substituted with up to a total of three methyl and/or methoxy and/or halogen groups, cyclopentane, morpholine, piperidine, N-methylpiperidine, N-ethylpiperidine, (N,N-diethyl)formamide, pyridine, pyrazine, pyrrole, pyrrolidine, furan, thiophene, tetrahydrofuran, pyran, tetrahydroisoquinoline, isoquinoline, quinoline. N-phenylpiperazine optionally substituted with up to a total of three methoxy and/or halogen groups, or N-benzylpiperazine;

A is an optional spacer group, attachable in either direction, selected from the group consisting of —NH—, —NHCH$_2$—, —NHCH$_2$CH$_2$—. —NHCH$_2$CH$_2$O—, and —NHCH$_2$(CH$_3$);

D is selected from the group consisting of methyl, isopropyl, tert-butyl, dimethylamine, morpholine, alcohol, phenyl optionally substituted with up to a total of three methyl and/or ethyl and/or methoxy and/or halogen and/or acetamide and/or ethoxy and/or cyano groups, pyridine, pyrazine, pyrrole, pyrrolidine, furan, thiophene, tetrahydrofuran, and pyran; and Z is an optional spacer group, selected from the group consisting of —CH$_2$—, —SO$_2$—, —SO$_2$CH$_2$—, —CH$_2$C(=O)—, —CH$_2$CH$_2$—, —C(=O)—, and —C(=S)NHC(=O)—.

In other embodiments, A is absent (thus X is directly connected to the phenyl ring at the position held by A); X is tetrahydroisoquinoline, attached to the phenyl ring by its lone nitrogen; Z is —C(=O)—; and D is methyl. In other embodiments, A is absent; X is morpholine, attached to the phenyl ring by its lone nitrogen; Z is —CH$_2$—; and D is methyl.

In certain additional embodiments, a candidate compound is a compound of Formula III:

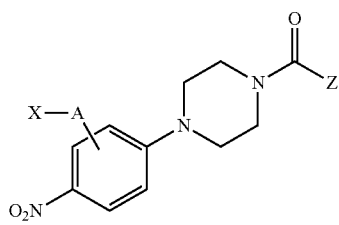

wherein

X is selected from the group consisting of methyl, methylamine, halogen, and phenyl optionally substituted with up to a total of three methyl and/or methoxy and/or halogen groups;

A is an optional spacer group, attachable in either direction, selected from the group consisting of —NH—. —N(CH$_3$)H—, —O—, —OCH$_3$—, —C(=O)NH—, and —NHCH$_2$—; and Z is selected from the group consisting of phenyl optionally substituted with up to a total of three methyl and/or ethyl and/or methoxy and/or halogen and/or acetamide and/or ethoxy and/or cyano groups; excepting those compounds that include X as phenyl and A as —NHCH$_2$—, the nitrogen in said A being connected to the nitro-containing phenyl ring in said formula and the carbon in said A being connected to said X in said formula.

In certain embodiments, a candidate compound is selected from the group consisting of:
(4-(4-nitro-3-(phenylamino)phenyl)piperazin-1-yl)(phenyl) methanone;
5-(4-dimethylcarbamylpiperazin-1-yl)-2-nitro-N-phenyl-benzenamine;
N-methyl-5-(4-benzoylpiperazin-1-yl)-2-nitro-N-phenyl-benzenamine;
N,N-dimethyl-5-(4-methylpiperazin-1-yl)-2-nitrobenzenamine;
N-(2-(4-benzoylpiperazin-1-yl)-5-nitrophenyl)acetamide;
2-(benzylamino)-N,N-dimethyl-4-(4-benzoylpiperazin-1-yl)benzamide;
2-(benzylamino)-N-ethyl-4-(4-benzoylpiperazin-1-yl)benzamide;
3'-(benzyl amino)-4'-nitrophenyl-3-carboxylic acid;
3'-(benzylamino)-4'-nitro-N-phenylbiphenyl-3-carboxamide;
ethyl-1-(3-(benzylamino)-4-nitrophenyl) piperidine-4-carboxylate; N-(2-(4-benzoylpiperazin-1-yl)-5-nitrophenyl) benzenamine;
(4-(4-amino-3-(phenylamino)phenyl)piperazin-1-yl)(phenyl)methanone;
1-(3-(benzylamino)-4-nitrophenyl) piperidine-3-carboxylic acid;
4'-nitro-3'-(phenylamino) biphenyl-3-carboxylic acid;
N,N-dimethyl-2-(4-benzoylpiperazin-1-yl)-5-nitrobenzenamine;
4'-amino-3'-(phenylamino) biphenyl-3-carboxylic acid;
(4-(3-(N-benzyl-N-phenylamino)-4-aminophenyl)piperazin-1-yl)(phenyl)methanone;
(4-(3-(N-methyl-N-phenylamino)-4-(dimethylamino)phenyl)piperazin-1-yl)(phenyl)methanone;
(4-(4-(dimethylamino)-3-(phenylamino)phenyl)piperazin-1-yl)(phenyl)methanone;
(4-(3-(N-methyl-N-phenylamino)-4-aminophenyl)piperazin-1-yl)(phenyl)methanone;
(4-(3-(N-methyl-N-phenylamino)-4-(methylamino)phenyl) piperazin-1-yl)(phenyl)methanone;
(4-(4-(methylamino)-3-(phenylamino)phenyl)piperazin-1-yl)(phenyl)methanone;
2-(4-(4-benzoylpiperazin-1-yl)-2-(phenylamino)phenylamino)ethanol;
N-benzyl-2-(4-benzoylpiperazin-1-yl)-5-nitrobenzenamine;
N-(4-(4-benzoylpiperazin-1-yl)-2-(phenylamino)phenyl) acetamide;
4-(4-benzoylpiperazin-1-yl)-N1-(2-morpholinoethyl)-N2-phenylbenzene-1.2-diamine,
pharmaceutically acceptable salts, stereo-isomers, polymorphs, metabolites, prod-drugs, analogs and combinations thereof.

In other embodiments, a candidate compound is selected from the group consisting of:
[4-[4-nitro-3-(tricyclo[3.3.1.13,7]dec-2-ylamino)phenyl]-1-piperazinyl]phenylmethanone;
2-(4-benzoyl-1-piperazinyl)-5-nitrobenzonitrile,
[4-[3-[(4-methyl-4H-1,2,4-triazol-3-yl)thio]-4-nitrophenyl]-1-piperazinyl]phenylmethanone,

[4-[4-nitro-3-(2-propen-1-ylamino)phenyl]-1-piperazinyl]
phenylmethanone,
[4-[3-[(2-methylpropyl)amino]-4-nitrophenyl]-1-piperazinyl]phenylmethanone,
[4-[4-nitro-3-[[(tetrahydro-2-furanyl)methyl]amino]phenyl]-1-piperazinyl]phenylmethanone,
[4-[3-[(2,2-dimethylpropyl)amino]-4-nitrophenyl]-1-piperazinyl]phenylmethanone,
[4-[3-(ethylamino)-4-nitrophenyl]-1-piperazinyl]phenylmethanone,
[4-(2-methyl-4-nitrophenyl)-1-piperazinyl]phenylmethanone,
5-[[2-(4-benzoyl-1-piperazinyl)-5-nitrophenyl]methylene]-2,4,6(1H,3H,5H)-pyrimidinetrione,
[4-[2-(2,5-dimethyl-1H-pyrrol-1-yl)-4-nitrophenyl]-1-piperazinyl]phenylmethanone,
[4-[4-nitro-2-(1H-pyrrol-1-yl)phenyl]-1-piperazinyl]phenylmethanone,
2-[5-(4-benzoyl-1-piperazinyl)-2-nitrophenyl]-4-methyl-1(2H)phthalazinone,
[4-[3-(methylamino)-4-nitrophenyl]-1-piperazinyl]phenylmethanone,
[4-[4-nitro-3-[(3-pyridinylmethyl)amino]phenyl]-1-piperazinyl]phenylmethanone,
[4-[3-(3,4-dihydro-2(1H)-isoquinolinyl)-4-nitrophenyl]-1-piperazinyl]phenylmethanone,
[4-[4-nitro-3-(1-piperidinyl)phenyl]-1-piperazinyl]phenylmethanone,
[4-[4-nitro-2-(trifluoromethyl)phenyl]-1-piperazinyl]phenylmethanone,
[4-[4-nitro-3-[(1-phenylethyl)amino]phenyl]-1-piperazinyl]phenylmethanone,
[4-[3-(4-morpholinyl)-4-nitrophenyl]-1-piperazinyl]phenylmethanone,
[4-[4-nitro-3-[(1-tricyclo[3.3.1.13,7]dec-1-ylethyl)amino]phenyl]-1-piperazinyl]phenylmethanone,
[4-[4-nitro-3-[(phenylmethyl)amino]phenyl]-1-piperazinyl]phenylmethanone,
[4-[4-nitro-3-[(2-phenylethyl)amino]phenyl]-1-piperazinyl]phenylmethanone,
[4-[3-[(2-furanylmethyl)amino]-4-nitrophenyl]-1-piperazinyl]phenylmethanone,
[4-[3-(3,5-dimethyl-1H-pyrazol-1-yl)-4-nitrophenyl]-1-piperazinyl]phenylmethanone,
[4-[3-(cyclopropylamino)-4-nitrophenyl]-1-piperazinyl]phenylmethanone,
[4-(2-chloro-4-nitrophenyl)-1-piperazinyl]phenylmethanone,
[4-(2-fluoro-4-nitrophenyl)-1-piperazinyl]phenylmethanone,
1-benzoyl-4-(3-formyl-4-nitrophenyl)piperazine,
1-benzoyl-4-[3-[(2,5-dioxo-4-imidazolidinylidene)methyl]-4-nitrophenyl]piperazine,
1-(3-amino-4-nitrophenyl)-4-benzoylpiperazine, 1-benzoyl-4-(4-nitrophenyl)piperazine,
(2,4-dichlorophenyl)[4-[4-nitro-3-[(phenylmethyl)amino]phenyl]-1-piperazinyl]methanone,
(5-chloro-2-methoxyphenyl)[4-[4-nitro-3-[(phenylmethyl)amino]phenyl]-1-piperazinyl]methanone,
[4-[4-nitro-3-[(phenylmethyl)amino]phenyl]-1-piperazinyl](4-propoxyphenyl)methanone,
(3,4-dimethoxyphenyl)[4-[4-nitro-3-[(1-phenylethyl)amino]phenyl]-1-piperazinyl]methanone,
(3,4-dimethoxyphenyl)[4-[4-nitro-3-[(phenylmethyl)amino]phenyl]-1-piperazinyl]methanone,
(3-chloro-4-methylphenyl)[4-[4-nitro-3-[(phenylmethyl)amino]phenyl]-1-piperazinyl]methanone,
(2-methoxy-3-methylphenyl)[4-[4-nitro-3-[(phenylmethyl)amino]phenyl]-1-piperazinyl]methanone,
(2-methoxy-3-methylphenyl)[4-[4-nitro-3-[(1-phenylethyl)amino]phenyl]-1-piperazinyl]methanone,
[4-(1-methylethoxy)phenyl][4-[4-nitro-3-[(1-phenylethyl)amino]phenyl]-1-piperazinyl]methanone,
[4-(1-methylethoxy)phenyl][4-[4-nitro-3-[(phenylmethyl)amino]phenyl]-1-piperazinyl]methanone,
[3-(1-methylethoxy)phenyl][4-[4-nitro-3-[(1-phenylethyl)amino]phenyl]-1-piperazinyl]methanone,
[3-(1-methylethoxy)phenyl][4-[4-nitro-3-[(phenylmethyl)amino]phenyl]-1-piperazinyl]methanone,
(4-ethylphenyl)[4-[4-nitro-3-[(1-phenylethyl)amino]phenyl]-1-piperazinyl]methanone,
(4-ethylphenyl)[4-[4-nitro-3-[(phenylmethyl)amino]phenyl]-1-piperazinyl]methanone,
(3-ethoxyphenyl)[4-[4-nitro-3-[(1-phenylethyl)amino]phenyl]-1-piperazinyl]methanone,
(3-ethoxyphenyl)[4-[4-nitro-3-[(phenylmethyl)amino]phenyl]-1-piperazinyl]methanone,
(3,4-dichlorophenyl)[4-[4-nitro-3-[(1-phenylethyl)amino]phenyl]-1-piperazinyl]methanone,
(3,4-dichlorophenyl) [4-[4-nitro-3-[(phenylmethyl)amino]phenyl]-1-piperazinyl]methanone,
[4-(1-methylethyl)phenyl][4-[4-nitro-3-[(1-phenylethyl)amino]phenyl]-1-piperazinyl]methanone,
(2-iodophenyl)[4-[4-nitro-3-[(phenylmethyl)amino]phenyl]-1-piperazinyl]methanone,
[4-(1,1-dimethylethyl)phenyl][4-[4-nitro-3-[(phenylmethyl)amino]phenyl]-1-piperazinyl]methanone,
(3-bromophenyl)[4-[4-nitro-3-[(1-phenylethyl)amino]phenyl]-1-piperazinyl]methanone,
[4-[4-nitro-3-[(1-phenylethyl)amino]phenyl]-1-piperazinyl]phenylmethanone,
(2-bromophenyl)[4-[4-nitro-3-[(1-phenylethyl)amino]phenyl]-1-piperazinyl]methanone,
(4-butoxyphenyl)[4-[4-nitro-3-[(phenylmethyl)amino]phenyl]-1-piperazinyl]methanone,
[4-(1-methylethyl)phenyl][4-[4-nitro-3-[(phenylmethyl)amino]phenyl]-1-piperazinyl]methanone,
(4-ethoxyphenyl)[4-[4-nitro-3-[(1-phenylethyl)amino]phenyl]-1-piperazinyl]methanone,
(2-methylphenyl)[4-[4-nitro-3-[(phenylmethyl)amino]phenyl]-1-piperazinyl]methanone,
(2-methylphenyl)[4-[4-nitro-3-[(1-phenylethyl)amino]phenyl]-1-piperazinyl]methanone,
(3-fluorophenyl)[4-[4-nitro-3-[(1-phenylethyl)amino]phenyl]-1-piperazinyl]methanone,
(3-fluorophenyl)[4-[4-nitro-3-[(phenylmethyl)amino]phenyl]-1-piperazinyl]methanone,
(3-methoxyphenyl) [4-[4-nitro-3-[(phenylmethyl)amino]phenyl]-1-piperazinyl]methanone,
(3-bromophenyl)[4-[4-nitro-3-[(phenylmethyl)amino]phenyl]-1-piperazinyl]methanone,
[4-(1,1-dimethylethyl)phenyl][4-[4-nitro-3-[(1-phenylethyl)amino]phenyl]-1-piperazinyl]methanone,
(4-ethoxyphenyl)[4-[4-nitro-3-[(phenylmethyl)amino]phenyl]-1-piperazinyl]methanone,
[4-[4-nitro-3-[(phenylmethyl)amino]phenyl]-1-piperazinyl]phenylmethanone,
(4-fluorophenyl)[4-[4-nitro-3-[(1-phenylethyl)amino]phenyl]-1-piperazinyl]methanone,
(4-chlorophenyl)[4-[4-nitro-3-[(1-phenylethyl)amino]phenyl]-1-piperazinyl]methanone,
(4-fluorophenyl)[4-[4-nitro-3-[(phenylmethyl)amino]phenyl]-1-piperazinyl]methanone, (2-chlorophenyl)[4-[4-nitro-3-[(1-phenyl ethyl)amino]phenyl]-1-piperazinyl]methanone,
(4-methylphenyl)[4-[4-nitro-3-[(1-phenylethyl)amino]phenyl]-1-piperazinyl]methanone,
[4-[3-[[(4-chlorophenyl)methyl]amino]-4-nitrophenyl]-1-piperazinyl](2-fluorophenyl)methanone,
(2-chlorophenyl)[4-[3-[[(4-chlorophenyl)methyl]amino]-4-nitrophenyl]-1-piperazinyl]methanone,
(4-bromophenyl)[4-[3-[[(4-chlorophenyl)methyl]amino]-4-nitrophenyl]-1-piperazinyl]methanone,
(2-chloro-4,5-difluorophenyl)[4-[4-nitro-3-[(phenylmethyl)amino]phenyl]-1-piperazinyl]methanone,
(2-chlorophenyl)[4-[4-nitro-3-[(phenylmethyl)amino]phenyl]-1-piperazinyl]methanone,
(4-methylphenyl)[4-[4-nitro-3-[(phenylmethyl)amino]phenyl]-1-piperazinyl]methanone,
(2-bromophenyl)[4-[4-nitro-3-[(phenylmethyl)amino]phenyl]-1-piperazinyl]methanone,
[4-[3-[[(4-chlorophenyl)methyl]amino]-4-nitrophenyl]-1-piperazinyl](4-methylphenyl)methanone,
[4-[3-[[[4-(1-methylethyl)phenyl]methyl]amino]-4-nitrophenyl]-1-piperazinyl](4-methylphenyl)methanone,
(3,5-dichloro-4-methoxyphenyl)[4-[3-[[[4-(1-methylethyl)phenyl]methyl]amino]-4-nitrophenyl]-1-piperazinyl]methanone,
(2-fluorophenyl)[4-[4-nitro-3-[(phenylmethyl)amino]phenyl]-1-piperazinyl]methanone,
(2-fluorophenyl) [4-[3-[[[4-(1-methylethyl)phenyl]methyl]amino]-4-nitrophenyl]-1-piperazinyl]methanone,
(4-chlorophenyl)[4-[3-[[[4-(1-methylethyl)phenyl]methyl]amino]-4-nitrophenyl]-1-piperazinyl]methanone,
[4-[3-[[(4-chlorophenyl)methyl]amino]-4-nitrophenyl]-1-piperazinyl](3-methylphenyl)methanone,
(3-methylphenyl)[4-[4-nitro-3-[(phenylmethyl)amino]phenyl]-1-piperazinyl]methanone,
(3-chlorophenyl)[4-[4-nitro-3-[(1-phenylethyl)amino]phenyl]-1-piperazinyl]methanone,
(3-chlorophenyl)[4-[3-[[(4-chlorophenyl)methyl]amino]-4-nitrophenyl]-1-piperazinyl]methanone,
(2-chloro-4,5-difluorophenyl)[4-[4-nitro-3-[(1-phenylethyl)amino]phenyl]-1-piperazinyl]methanone,
(2-chloro-4,5-difluorophenyl)[4-[3-[[(4-chlorophenyl)methyl]amino]-4-nitrophenyl]-1-piperazinyl]methanone,
(4-bromophenyl)[4-[4-nitro-3-[(1-phenylethyl)amino]phenyl]-1-piperazinyl]methanone,
(3-chlorophenyl)[4-[4-nitro-3-[(phenylmethyl)amino]phenyl]-1-piperazinyl]methanone,
(4-methoxyphenyl)[4-[4-nitro-3-[(1-phenylethyl)amino]phenyl]-1-piperazinyl]methanone,
[4-[3-[[(4-chlorophenyl)methyl]amino]-4-nitrophenyl]-1-piperazinyl](4-methoxyphenyl)methanone,
(4-methoxyphenyl)[4-[4-nitro-3-[(phenylmethyl)amino]phenyl]-1-piperazinyl]methanone,
[4-[3-[[(4-chlorophenyl)methyl]amino]-4-nitrophenyl]-1-piperazinyl](2-methoxyphenyl)methanone,
(2-methoxyphenyl)[4-[4-nitro-3-[(phenylmethyl)amino]phenyl]-1-piperazinyl]methanone,
(4-bromophenyl)[4-[4-nitro-3-[(phenylmethyl)amino]phenyl]-1-piperazinyl]methanone,
(2-bromophenyl)[4-[3-[[(4-chlorophenyl)methyl]amino]-4-nitrophenyl]-1-piperazinyl]methanone,
pharmaceutically acceptable salts, stereo-isomers, polymorphs, metabolites, prod-drugs, analogs and combinations of any of the foregoing.

In certain embodiments, the candidate compound is represented by one of one of the following structural formulas:

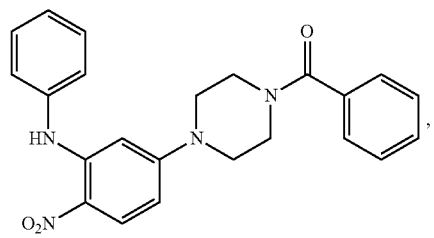

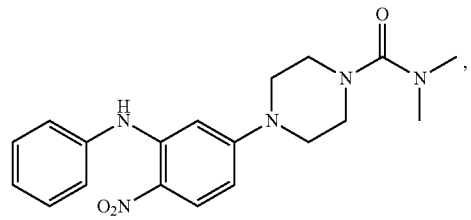

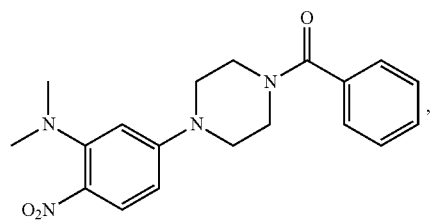

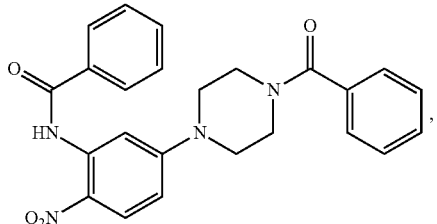

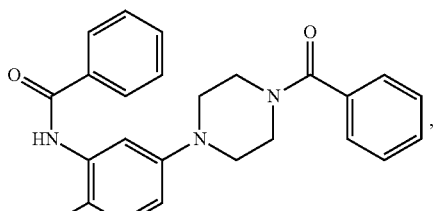

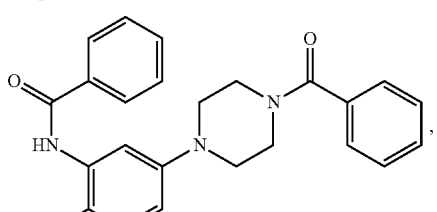

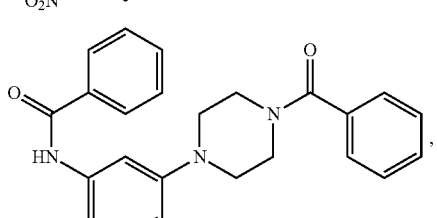

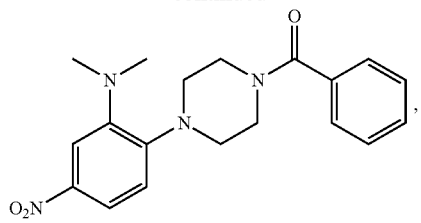
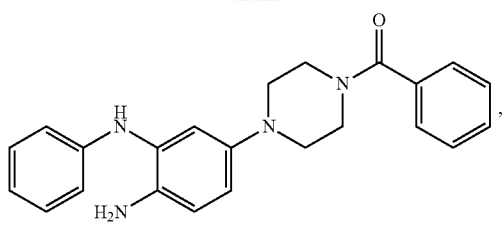
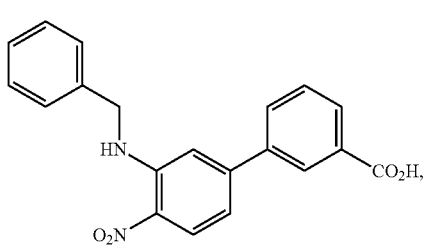
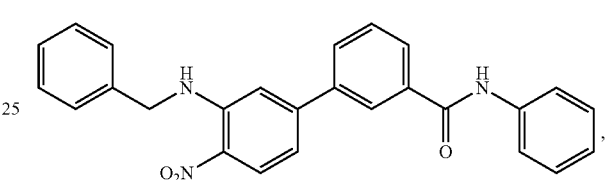
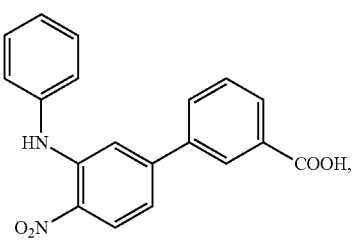
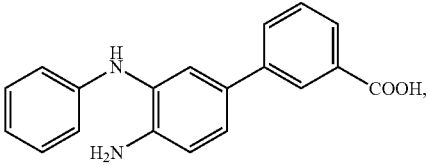
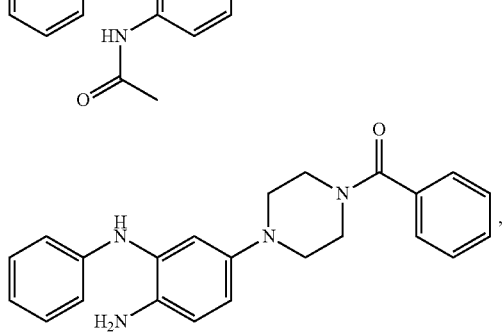

-continued

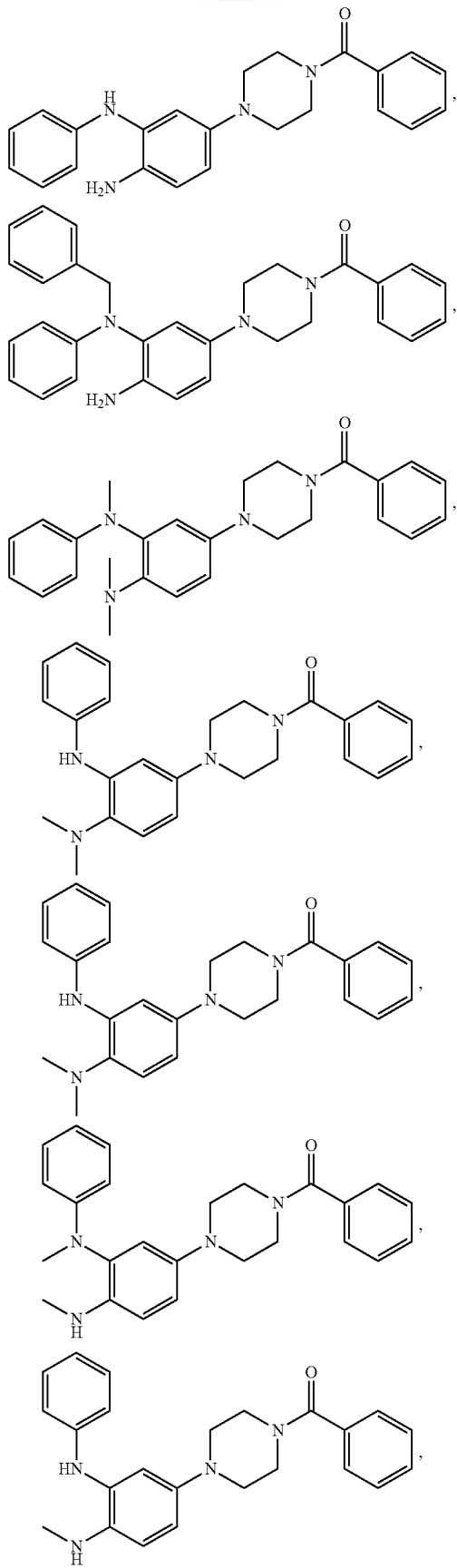

-continued

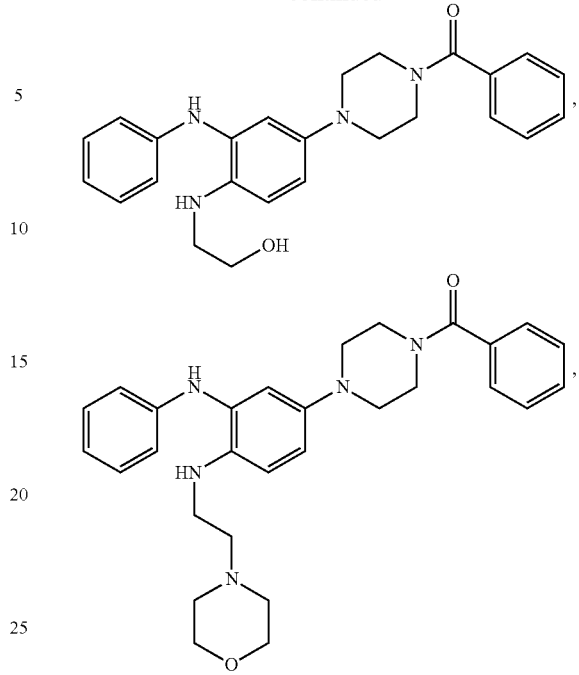

pharmaceutically acceptable salts, stereo-isomers, polymorphs, metabolites, pro-drugs, analogs and mixtures of any of the foregoing.

In certain embodiments, the candidate compound has activity against both Aβ and A-Syn, as determined by a ThT functional aggregation assay.

In certain embodiments, the candidate compound has activity against both Aβ and tau, as determined by a ThT functional aggregation assay.

In certain embodiments, the candidate compound only has activity against Aβ, as determined by a ThT functional aggregation assay.

In certain embodiments, the IC50/μM for Aβ for the candidate compound is from about 0.5 to about 5734, as determined by ThT functional aggregation assay. In certain embodiments, the IC50/μM for Aβ is from about 0.8 to about 180. In certain embodiments, the IC50/μM for Aβ is from about 0.8 to about 107. In certain embodiments, the IC50/μM for Aβ is 0.85, 0.88, 1.47, 1.9, 2.3, 2.29, 3.5, 7.5, 8.4, 9.64, 15.5, 18, 23, 25, 26.5, 54, 66, 84, 90, 92, and 100.

In certain embodiment, the IC50/μM for A-syn for A-Syn, as determined by A-Syn functional ThT aggregation assay, for the candidate compound is from about 1 to about 70. In certain embodiment, the IC50/μM for A-syn is from about 5 to about 50. In certain embodiment, the IC50/μM for A-syn is 4, 5, 10, 15 or 45.

In certain embodiments, the IC50/μM for Aβ for the candidate compound is 0.85, 9.64, 25, 1.47, 9.23, 27, 26.6, or 3.5; and the IC50/μM for A-syn is 6.34, 5, 4, 7, 8, 10, 15, or 45.

One example of a pseudo-crystal structure utilized in these methods is the one formed by SEQ ID: 1 and SEQ ID: 2 when interacting in the manner depicted in FIG. 2.

In certain embodiments, a method of identifying compounds that modulate amyloid aggregation comprises the steps of constructing a pseudo-crystal structure in a computer modeling program; selecting a list of candidate compounds; constructing said candidate compounds in a computer modeling program; performing an iterative docking and scoring of all candidate compounds, by means of docking each candidate compound into the pocket formed by said model and scoring each candidate compound to reflect its degree of complementarity with respect to said pocket; and identifying compounds that modulate amyloid aggregation by reference to a score cutoff that substantially distinguishes active compounds from inactive compounds. A score cutoff is usually an absolute energy, that can be set higher or lower depending on the level of activity that is deemed to separate active from inactive, or as a reference between more active and less active. In some embodiments, the score cutoff is the value of a known active compound. In other embodiments, the score cutoff is the value that distinguishes a small part (i.e. 1% to 10%) of a set of compounds as being substantially more active than other members of the set.

In certain embodiments, the pseudo-crystal structure comprises a three-dimensional model of uncrystallized, monomeric amyloid protein and a three-dimensional model of uncrystallized amyloid protein or oligomer comprising one or more amyloid peptides, said amyloid protein or oligomer model to be positioned with respect to said amyloid monomer model such that it forms a pocket in conjunction with said amyloid monomer model, such that a compound may be inserted into said pocket thereby modulating amyloid aggregation.

In certain embodiments, the amyloid monomer model and the amyloid protein or oligomer model are both composed of beta-amyloid protein or an amyloidogenic fragment thereof.

In other embodiments, said amyloid monomer model is substantially SEQ ID: 1 and said amyloid oligomer model is substantially SEQ ID: 2. In certain embodiments, said amyloid monomer model is further positioned with respect to said amyloid protein model such that the amino acid Val at position 8 of SEQ ID: 1 interacts with the amino acid Glu at position 6 of SEQ ID: 2; the amino acid Gly at position 9 of SEQ ID: 1 interacts with the amino acid Glu at position 6 of SEQ ID: 2; the amino acid Ser at position 10 of SEQ ID: 1 interacts with the amino acid Gly at position 9 of SEQ ID: 2; the amino acid Ser at position 10 of SEQ ID: 1 interacts with the amino acid Ser at position 10 of SEQ ID: 2; and the amino acid Lys at position 12 of SEQ ID: 1 interacts with the amino acid Glu at position 6 of SEQ ID: 2. In certain embodiments, the amyloid monomer model is positioned with respect to the amyloid protein model substantially in the orientation shown in FIG. 2. In certain embodiments, the candidate compounds are drawn from proprietary compound collections and/or from commercially available screening libraries.

The process of docking as implemented in the computer modeling program or programs is described, e.g., in the manuals of said program or programs. Docking may be performed, e.g., interactively or in batch mode. Computer modeling programs especially suited to docking include, but are not restricted to, DOCK. AUTODOCK, GLIDE, and FlexX. The manuals of these programs are herein incorporated by reference in their entirety for all purposes.

Scoring functions are generally applied after docking and may be integral to a given docking method. Examples of scoring functions include DrugScore, London, and Affinity dG. In some embodiments, the scoring function may be a composite of two or more scoring functions.

In certain embodiments, a method of improving potency of a compound known to modulate amyloid aggregation comprising the steps of constructing a pseudo-crystal structure in a computer modeling program; selecting a list of candidate compounds; constructing said candidate compounds in a computer modeling program; performing an iterative docking and scoring of all candidate compounds, by means of docking each candidate compound into the pocket formed by said model and scoring each candidate compound to reflect its degree of complementarity with respect to said pocket; and identifying compounds that modulate amyloid aggregation by reference to a score cutoff that substantially distinguishes more active compounds from less active compounds. In certain embodiments of the invention, the list of candidate compounds includes both the compound known to be active and analogs of said compound, and the score cutoff is that score which belongs to the compound known to be active. In certain embodiments, the pocket comprises substantially SEQ ID: 1 and amyloid oligomer model has substantially SEQ ID: 2, wherein SEQ ID: 1 is

```
Leu Val Phe Phe Ala Glu Asp Val Gly Ser Asn
1                   6                       11

Lys Gly Ala Ile Ile Gly Leu Met Val Gly Gly
    Val
                16                      21

Val Ile Ala
        26
``` and,
SEQ ID: 2 is

```
Leu Val Phe Phe Ala Glu Asp Val Gly Ser Asn
1                   6                       11

Lys Gly Ala Ile Ile Gly Leu Met Val Gly Gly
    Val
                16                      21

Val Ile Ala
        26
```

In certain embodiments, the two sequences comprising the pocket are not substantially the same.

In certain embodiments, the present invention uses known non-peptidic compounds amyloid and/or amyloidogenic fragments to identify new compounds which may be inhibitors or likely to be inhibitors of amyloid protein aggregation. For example, a wide variety of non-peptidic compounds have shown the ability to inhibit the aggregation of amyloid proteins in vitro, and many such compounds can inhibit the aggregation of beta-amyloid protein as well as other kinds of amyloid (see for example Klabunde et al, 2000, Nat. Struct. Biol. 7:312-321; Green et al, 2003, J. Am. Chem. Soc. 125:13404-13414; Masuda et al, 2006, Biochemistry 45:6085-6094; Ono et al, 2003, J. Neurochem 87:172-181; Tagliavini et al, 2000. J. Mol Biol. 300:1309-1322). In addition, a number of amyloid proteins or amyloidogenic fragments thereof have been crystallized, including islet amyloid polypeptide or amylin (Willzius et al. 2008. Protein Sci. Jun. 12 online); beta-2-microglobulin or light chain (Iwata et al, 2007, J. Biochem. 142:413-419; Schormann et al, 1995, Proc. Natl. Acad. Sci. USA 92:9490-9494), insulin; and notably transthyretin, which has been crystallized several times in co-crystal with known inhibitors (Hamilton et al, 1993, J. Biol. Chem. 268:2416-2424; Peterson et al. 1998, Proc. Natl. Acad. Sci. USA 95:12956-12960; Klabunde et al, 2000, Nat. Struct. Biol. 7:312-321). Some known compounds have also been shown to have beneficial in vivo effects, including reducing the size of amyloid plaques and delaying mortality in mouse models of amyloid disease (Chen et al, 2000, Nat. Med. 6:797-801; Imbimbo et al. 2007, Pharmacol. Res. 55:318-328). It is postulated that compounds that modulate the aggregation of amyloid protein in vitro (so-called "anti-amyloid compounds") and have in vivo effects may be beneficial for the treatment of amyloid diseases, e.g., Alzheimer's Disease. In certain embodiments, the present invention uses these known compounds to identify new compounds which may be inhibitors or likely to be inhibitors of amyloid protein aggregation. One compound which may be used in the methods of the present invention (e.g., as a multiply anti-amyloid compound) is resveratrol, an antioxidant component of red wine and an inhibitor of beta-amyloid aggregation at an effective concentration of 5.6 µM (Riviere et al. 2007, Bioorg. Med. Chem. 15:1160-1167).

In certain embodiments, the invention is directed to methods of improving potency of a compound known to modulate amyloid aggregation comprising the steps of constructing a pseudo-crystal structure in a computer modeling program; selecting a list of candidate compounds; constructing said candidate compounds in a computer modeling program; performing an iterative docking and scoring of all candidate compounds, by means of docking each candidate compound into the pocket formed by said model and scoring each candidate compound to reflect its degree of complementarity with respect to said pocket; and identifying compounds that modulate amyloid aggregation by reference to a score cutoff that substantially distinguishes more active compounds from less active compounds. In certain embodiments, the pseudo-crystal structure for this method is the one formed by SEQ ID: 1 and SEQ ID: 2 when interacting in the manner depicted in FIG. 2. The list of candidate compounds may include. e.g., both the compound known to be active anti-amyloid compounds and analogs of such compounds, and the score cutoff is that score which belongs to the compound known to be active. In certain embodiments, the known compound is a compound selected from the lists recited in paragraphs [0106] to [0117] of the application. In certain embodiments, the known compound is resveratrol.

The invention also encompasses and provides for use of the compounds identified or improved using the invention's methods as therapies for diseases in which amyloidosis occurs. The disease include (but are not limited to) Alzheimer's disease, Huntington's disease, Parkinson's disease, Creutzfeldt-Jacob disease, amyotrophic lateral sclerosis, and senile systemic amyloidosis. In certain embodiments, the disease is Alzheimer's disease. In certain embodiments, the therapeutic compound inhibits aggregation of one or more of the following amyloidogenic proteins: beta-amyloid protein, tau protein, alpha-synuclein protein, huntingtin protein, prion precursor protein; other amyloidogenic protein not named herein, and combinations of any of the foregoing.

In certain preferred embodiments, both the aggregation of alpha-synuclein protein and of tau protein are inhibited. In certain embodiments, both the aggregation of beta-amyloid protein and of tau protein are inhibited. In certain embodiments, both the aggregation of beta-amyloid protein and of alpha-synuclein protein are inhibited. In certain embodiments, only the aggregation of tau protein, beta-amyloid protein, or alpha-synuclein protein is inhibited. In certain embodiments, the aggregation of beta-amyloid protein, tau protein, and alpha-synuclein protein are all inhibited. In certain embodiments, huntingtin aggregation is inhibited. In certain embodiments, prion protein aggregation is inhibited.

In certain embodiments, the methods comprise administering to a subject a therapeutic compound identified or improved using the invention's methods (including analogs and derivatives of such compounds) and/or pharmaceutically acceptable salts thereof, such that the therapeutic compound inhibits the aggregation of an amyloidogenic protein. The subject in these methods may be, e.g., a vertebrate, a mammal, a human, or a non-human animal. The administration may be, e.g., oral, parenteral, transdermal, intrathecal, or intranasal.

In certain embodiments, the methods comprise using known amyloid and/or amyloidogenic fragments to discover and/or optimize compounds that modulate their respective amyloid protein, and other amyloid proteins, e.g., due to the purported relative universality of amyloid pathogenesis. (Kayed et al. 2003, Science 300:486-489; Bucciantini et al, 2002, Nature 416:507-511). For example, transthyretin is known to bind beta-amyloid protein in vivo, probably as aggregated beta-amyloid (Tsuzuki et al, 2000, Neurosci. Lett. 281:171-174; Liu and Murphy, 2006, Biochemistry 45:15702-15709), and several inhibitors of transthyretin are also known to inhibit beta-amyloid protein. However, as such compounds do not inhibit both transthyretin and beta-amyloid protein with equal potency, the utility of transthyretin crystal structures per se for discovering inhibitors of beta-amyloid protein does not approach what might be expected if a similar crystal structure of beta-amyloid were available. The methods of present invention in certain embodiments provide for the utilization of these compounds (despite the lack of known crystal structure of beta-amyloid) to identify new compounds which may be inhibitors or likely to be inhibitors of simultaneous inhibition of several amyloid proteins.

In other embodiments, the invention relates to methods of virtually screening of compound library, e.g., in silico screening. More specifically, the invention relates to methods of virtually screening a library or libraries to identify compounds that are likely to inhibit amyloid protein aggregation. Such compounds would be of use as therapies for neurodegenerative diseases such as Alzheimer's disease. Parkinson's disease, Huntington's disease, prion diseases, and systemic amyloidosis.

The utility and operation of the embodiments of the invention can be further appreciated by reference to the following non-limiting examples:

Example 1

Construction of a Common Conformational Motif Model and Subsequent Extraction of a Model of Amyloid Protein Aggregation A Common Conformational Motif model was constructed using a computer modeling program in interactive session and validated.

First, resveratrol was drawn and minimized to a root-mean-square gradient of 0.05 using the MMFF94 force field with corresponding partial charges. The PDB structure 1BM7 (www.pdb.org) of transthyretin bound to flufenamic acid was loaded, and resveratrol was manually placed in a position coincident with one of the two flufenamic acid binding sites. The binding site of the other flufenamic acid (i.e. the other homodimer), the flufenamic acid moiety in the resveratrol-occupied binding site, and any solvent molecules were deleted. The 17-42 residue sequence of beta-amyloid protein was then drawn and duplicated, and the two strands of beta-amyloid protein were placed in close, non-overlapping proximity to each other and to resveratrol. The entire structure was then correctly protonated/deprotonated for physiological pH and minimized to a root-mean-square gradient of 0.05 using the MMFF94 force field with corresponding partial charges. The orientation of one strand of beta-amyloid protein with respect to the other was a matter of routine experimentation, as the method furnished both a means of adjusting the structure such that a pocket is formed and a means of validating that the candidate model was useful. Several dozen candidate models were created and extracted. One model was validated as the Common Conformational Motif model and is depicted in FIG. 1.

The model of amyloid protein aggregation was then extracted. The extracted model of amyloid protein aggregation is depicted in FIG. 2. FIG. 2 shows two $A\beta_{17\text{-}42}$ monomers bound to each other near the N terminals in a "double candycane" structure. Each monomer is folded in a loop from residues 23 through 33. The loops are stabilized by intra-loop cationic-anionic interactions between $Asp_{23}$ and $Lys_{28}$, and they also show an inter-loop attraction through these same residues. Short-run (up to 100 ns) molecular dynamics calculations on this model indicate that the pocket is stable.

When the model of amyloid protein aggregation depicted in FIG. 2 was compared to the structure of transthyretin ("TTR") depicted in FIG. 1, a number of similarities were observed. The model of amyloid protein aggregation depicted in FIG. 2 provided a similar expanse of hydrophobic contact by lining up along two flattened sides of what would otherwise be a much smaller area of β-sheet, rather than forming a pocket across the top of several β-sheets. Anti-amyloid compounds in the amyloid protein aggregation model of FIG. 2 were stabilized in the pocket by Lys and Ser and by exterior Leu, just as in the structure of TTR. Similarly, the positive charge of Lys was shared between the substrate and a nearby Asp in both structures.

It was therefore postulated that a small negatively charged compound might be able to fit between both Lys residues and benefit from the salt bridge interaction, as was reported in TTR. It was further postulated that model of amyloid protein aggregation depicted in FIG. 2 may be a transient species on the way to a stacked dimer using a "dock-lock" mechanism. It is known that many anti-amyloid compounds are multiply anti-amyloid. As such, it was postulated that the utility of the models of the present invention extends beyond the prevention of beta-amyloid protein aggregation and includes additional species of the amyloid proteins, therefore we hypothesized that it can be considered a common conformational motif, of utility for other amyloids beyond beta-amyloid protein.

Example 2

Validation of the CCM Model of Amyloid Protein Aggregation of Example 1

A burgeoning number of compounds have been shown to be anti-amyloidogenic and/or anti-fibrillogenic. To validate the model of amyloid protein aggregation constructed in Example 1, and in view of its potential extension to other amyloid proteins like α-synuclein, a set of these compounds was evaluated in an in silico docking screen using a collection of 79 compounds for which $IC_{50}$s have been computed for Aβ, tau, and α-synuclein inhibition. This diverse set comprised polyphenols, benzothiazoles, phenothizaines, macrolides, prophyrins, steroids, derivatives of Congo red, and other anti-amyloid molecules of note.

Among the 39 polyphenols evaluated in the screen, the best docking scores were predicted for purpurogallin, epigallocatechin, catechin gallate, hinokiflavone, myricetin, and gallocatechin gallate—all of which have $IC_{50}$s below 7 µM. The worst scores in the test were predicted for rutin (expt $IC_{50}$ 32 µM) and chlorogenic acid (>40 µM). Since each compound was represented by several poses, computing a ranking for the remaining compounds was somewhat ambiguous. Nevertheless, the preliminary result was encouraging enough to consider a more stringent criterion: the quantitative structure-activity relationship (QSAR). The Masuda test set was subjected to a CoMFA (comparative molecular field analysis) in order to demonstrate the validity of the model of amyloid protein aggregation depicted in FIG. 2.

CoMFA is a 3-D QSAR technique generally used to posit a "pseudoreceptor" when none is known. Because the algorithm is highly sensitive to alignment of compounds with respect to each other, it is often difficult to produce statistically significant results, even with structurally similar compounds. However, when statistically significant results are obtained, this can be a great confirmation of a pharmacophore hypothesis.

Using the three best poses from the docking calculation as the initial test set (3×79=237 total poses), a partial least squares analysis of the fit indicated a cross-validated $r^2$ (i.e. $q^2$) of 0.248. Removing 25 outlying poses improved the leave-one-out $q^2$ to 0.616. A more laborious bootstrapping calculation produced a $q^2$ of 0.619. This result indicated that the CoMFA pseudoreceptor had a good agreement with experiment when the molecules are aligned in accordance with the model of amyloid protein aggregation depicted in FIG. 2. Only eight of the 79 compounds were predicted as false positives:

|  | Predicted | Expt |
| --- | --- | --- |
| Polyphenols |  |  |
| Apigenin | 1.4 | >40 |
| Baicalein | 7.8 | 4.5 |
| Catechin | 10.8 | >40 |
| Catechin gallate | 6.2 | 5.0 |
| chlorogenic acid | >40 | >40 |
| curcumin | 2.0 | 1.7 |
| cyanidin | 4.8 | 4.0 |
| daidzein | 2.8 | >40 |
| delphinidin | 4.4 | 3.0 |
| 2,2'-dihydroxybenzophenone | >40 | >40 |
| 4,4'-dihydroxybenzophenone | 1.6 | >40 |
| dopamine chloride | 6.7 | 28.6 |
| epicatechin | 16.1 | >40 |
| epicatechin 3-gallate | 2.3 | 3.0 |
| epigallocatechin | 8.7 | 7.0 |
| epigallocatechin gallate | 2.5 | 2.0 |
| exifone | 2.2 | 0.7 |
| gallocatechin | 12.4 | 7.0 |
| gallocatechin gallate | 2.1 | 1.5 |
| gingerol | 19.8 | 25.0 |
| gossypetin | 1.2 | 1.3 |
| hinokiflavone | 5.8 | 5.0 |
| hypericin | 1.5 | 0.9 |
| kaempferol | 8.3 | 8.0 |
| luteolin | 3.6 | 3.0 |
| myricetin | 0.9 | 0.9 |
| naringenin | 3.2 | 25.0 |
| 2,3,4,2',4'-pentahydroxybenzophenone | 2.2 | 2.8 |
| procyanidin B1 | 21.6 | 14.0 |
| procyanidin B2 | >40 | >40 |
| purpurogallin | 3.2 | 0.5 |
| quercetin | 4.3 | 5.0 |
| rosmarinic acid | 8.7 | 12.0 |
| rutin | >40 | 32.0 |
| taxifolin | 1.0 | >40 |

-continued

|  | Predicted | Expt |
|---|---|---|
| 2,2',4,4'-tetrahydroxybenzaphenone | 3.2 | >40 |
| theaflavone | 2.8 | 2.0 |
| tocopherol | >40 | >40 |
| 2,3,4-trihydroxybenzophenone | 6.4 | 3.1 |
| anthracycline | | |
| daunorubicin hydrochloride | 1.3 | 1.4 |
| benzothiazoles | | |
| 2-(4-aminophenyl)-6-methylbenzothiazole | 2.4 | 2.0 |
| basic blue 41 | 1.2 | 1.4 |
| 2-[4-(dimethylamino)phenyl]-6-methylbenzothiazole | 2.0 | 2.0 |
| 3,3'-dipropyl thiodicarbocyanine iodine | 0.3 | 0.3 |
| lignans | | |
| magnolol | >40 | >40 |
| sesamin | 19.2 | >40 |
| phenothiazines | | |
| acetopromazine maleate salt | >40 | >40 |
| azure A | 0.5 | 0.4 |
| azure C | 0.5 | 0.2 |
| chlorpromazine hydrochloride | >40 | >40 |
| lacmoid | 3.8 | 1.4 |
| methylene blue | 20.0 | 2.3 |
| perphenazine | >40 | >40 |
| promazine hydrochloride | >40 | >40 |
| propionylpromazine hydrochloride | >40 | >40 |
| quinacrine | 8.9 | 8.4 |
| quinacrine mustard | 1.8 | 1.2 |
| polyene macrolides | | |
| amphotericin B | 2.0 | 2.2 |
| filipin III | 14.7 | 14.6 |
| porphyrins | | |
| ferric dehydroporphyrin IX | 0.2 | 0.2 |
| hematin | 0.2 | 0.2 |
| phthalocyanine tetrasulfonate | 3.9 | 3.2 |
| rifamycin | | |
| rifampicin | 4.0 | 4.9 |
| steroids | | |
| laurochenodeoxycholic acid | >40 | >40 |
| taurohydroxycholic acid | >40 | >40 |
| taurolithocholic acid | >40 | >40 |
| taurolithocholic aicd 3-sulfate | >40 | >40 |
| tauroursodeoxycholic acid | >40 | >40 |
| Congo red and derivatives | | |
| Congo red | 1.0 | 0.9 |
| chlorazol black E | 0.2 | 0.3 |
| BSB | 5.5 | 6.4 |
| FSB | 3.0 | 1.9 |
| Ponceau SS | 1.2 | 1.2 |
| terpenoids | | |
| asiatic acid | >40 | >40 |
| ginkgolide A | >40 | >40 |
| ginkgolide B | 14.4 | 11.0 |
| ginkgolide C | >40 | >40 |
| others | | |
| 4,5-dianilinophthalimide | 5.4 | 2.9 |
| methyl yellow | 2.2 | 1.5 |

It was therefore concluded that the model of amyloid protein aggregation of FIG. 2 has utility in predicting the anti-amyloid effects of candidate compounds tested in the example, and that these compounds have activity against aggregation of β amyloid protein. It was also postulated that, given conformational similarities between certain amyloid proteins, the candidate compounds may inhibit aggregation of other amyloid proteins, and that dimers of beta-amyloid protein in general may have significant utility in predicting the anti-amyloid effects of candidate compounds on other amyloids such as tau, alpha-synuclein, huntingtin, and/or prion protein.

Example 3

Identification of Compounds that Modulate Amyloid Protein Aggregation and Improvement of Potency Using the Common Conformational Motif Model The Common Conformational Motif model created in Example 1 was used to demonstrate its utility for rapid lead discovery.

A simple geometric query against a diverse collection of around 750,000 drug-like compounds was constructed and yielded 1,260 compounds with non-hydrogenic atoms lying within 0.1 Å of each point in the 3-point pharmacophore. Searching in this manner allowed for a quick (<90 min) pre-screening prior to the more computationally laborious docking procedure. Using the parameters for docking as described above, each of the 1,260 compounds were fit into the CCM model (i.e., depicted in FIG. 2).

The top 125 compounds were examined for commercial availability, and six of these compounds, evenly distributed with respect to docking score, were acquired from Hit2Lead for in vitro testing. Three of these compounds were inactive in the ThT assay, one was weakly active, and two were highly active (see U.S. Provisional Application Ser. No. 61/092,845 for initial compound disclosures and subsequent use of the model for improving.

One-half of compounds (50%) initially tested had some activity, and one-third (33.3%) had significant activity, as compared to the typical hit rate of a high-throughput screen (generally no more than 0.5%) with traditional screening techniques. These results therefore confirmed that the screening technique utilized in this example is highly hit-enriched screening technique and may be more effective, as compared to traditional screening techniques.

The present example therefore confirms, e.g., that the model created in Example 1 has utility for rapid lead discovery.

It was then postulated that, e.g., because a number of the compounds described in the application were shown to be multiply anti-amyloid compounds, that pseudo-crystal structures described in the application may be useful for identification and optimization of anti-tau, anti-alpha-synuclein, and other anti-amyloid applications, in addition to being useful in rapid lead discovery of compounds that may prevent aggregation of beta-amyloid protein.

Example 4

Identification of Known Compounds that Modulate Amyloid Protein Aggregation Using the Model of FIG. 2

Further validation of the CCM model of protein aggregation (i.e., the model of FIG. 2) was performed using a screen of the PubChem collection (http://www.ncbi.nlm.nih.gov) using a blank structure query and a limit query of "Pharmacological Action." The query returned 14.172 compounds, consisting entirely of molecules known to have a pharmacological effect.

This set of 14.172 compounds was then downloaded in MDL SDfile format, imported into a molecular modeling program, stripped of counterions and assigned physiologically appropriate protonation states, and minimized using a molecular mechanics force field.

Next, an unguided docking study was performed, using docking parameters and binding site identification identical to that above, on the PubChem set. The results for the top 25, in decreasing order of binding score and repeated hits in parenthesis, were as follows: chlorophyllin (2), epigallocatechin gallate (3), coumermycin A1, chlorotetracycline (2), doxycycline (2), hygromycin B, rolitetracycline, desfarrioxamine, epicatechin gallate, transcycline, oligoadenylade, 8-azido-ADP, citrinin, tetrakis(4-N-methylpyridyl)porphyrin, tetracycline, acteoside, actinonin, lactitol, minocycline, and rocephalin.

What was striking in these results was that they included a number of known anti-amyloid compounds and compound families. Specifically, porphyrins, polyphenols, and tetracyclines constituted fully 60% of the top scores, which is significantly better than most high-throughput screening campaigns. The list also included known anti-amyloid compounds not considered part of any family, including desferrioxamine and the neuroprotectant acteoside.

It was therefore postulated that most of the remaining top twenty five compounds were also likely to have effects against Aβ aggregation, especially given their highly symmetrical structures (coumermycin, hygromycin, oligoadenylate), structural affinity with NSAIDs (citrinin), and/or reported utility in related protein misfolding/aggregation diseases such as Huntington's disease (actinonin) and ALS (rocephalin).

Moreover, some compounds which were known for uses other than anti-amyloid have been identified as being anti-amyloid by the screen. It was therefore postulated that these compounds may have utility in treating Alzheimer's Disease and related disorders (e.g., Parkinson's Disease). For example, exploration of hits in the top 1% included those mentioned above as well as the following, in no particular order of activity: Pradimicin, Oleuropein, Tunicamycin. Hyaluronic acid. Coumermycin, Ouabain. Amikacin, Rifaximin, delavirdine, almitrine, and fluvastatin, lumiracoxib, and fenoterol. It was therefore postulated that these compounds may have utility in treating amyloid diseases.

In this regard, it is notable that even compounds that do not ordinarily cross the blood-brain barrier are often capable of crossing it in patients with neurologic disorders, and that neurologic disorders of the peripheral nervous system also can benefit from anti-amyloid compounds. As such, it was postulated that the physiochemical parameters of an identified anti-amyloid molecule may not need to fit into Log P, molecular weight, and other ranges associated with blood-brain barrier penetration in order to have utility in treatment of neurologic disorders (e.g., Alzheimer's Disease and/or related disorders).

DATA LISTING

The model of FIG. 2 in PDB format.
This listing can be transcribed into a text file (Unicode. ASCII, or other standard encoding), saved to disc as with extension .PDB, and loaded into a PDB-aware visualization or modeling program in order to reconstruct the model.

| HEADER | | | | | | PROTEIN FIBRIL | | | | |
|---|---|---|---|---|---|---|---|---|---|---|
| REMARK | | 99 MOE v2007.09 | | | | (Chemical Computing Group Inc) | | Mon Jun 16 15:27:17 2008 | | |
| ATOM | 1 | N | LEU | E | 17 | −4.245 | −9.375 | 10.249 | 1.00 | 0.00 | N1+ |
| ATOM | 2 | H1 | LEU | E | 17 | −4.274 | −8.787 | 9.368 | 0.00 | 0.00 | H |
| ATOM | 3 | H2 | LEU | E | 17 | −4.396 | −8.764 | 11.070 | 0.00 | 0.00 | H |
| ATOM | 4 | CA | LEU | E | 17 | −5.267 | −10.479 | 10.168 | 1.00 | 0.00 | C |
| ATOM | 5 | C | LEU | E | 17 | −4.618 | −11.861 | 10.006 | 1.00 | 0.00 | C |
| ATOM | 6 | O | LEU | E | 17 | −3.393 | −11.958 | 9.924 | 1.00 | 0.00 | O |
| ATOM | 7 | CB | LEU | E | 17 | −6.281 | −10.169 | 9.008 | 1.00 | 0.00 | C |
| ATOM | 8 | CG | LEU | E | 17 | −7.425 | −9.144 | 9.299 | 1.00 | 0.00 | C |
| ATOM | 9 | CD1 | LEU | E | 17 | −6.943 | −7.714 | 9.627 | 1.00 | 0.00 | C |
| ATOM | 10 | CD2 | LEU | E | 17 | −8.432 | −9.109 | 8.124 | 1.00 | 0.00 | C |
| ATOM | 11 | H3 | LEU | E | 17 | −3.272 | −9.775 | 10.284 | 1.00 | 0.00 | H |
| ATOM | 12 | HA | LEU | E | 17 | −5.791 | −10.502 | 11.115 | 1.00 | 0.00 | H |
| ATOM | 13 | HB2 | LEU | E | 17 | −5.722 | −9.849 | 8.101 | 1.00 | 0.00 | H |
| ATOM | 14 | HB3 | LEU | E | 17 | −6.795 | −11.117 | 8.729 | 1.00 | 0.00 | H |
| ATOM | 15 | HG | LEU | E | 17 | −7.992 | −9.514 | 10.187 | 1.00 | 0.00 | H |
| ATOM | 16 | HD11 | LEU | E | 17 | −7.811 | −7.028 | 9.744 | 1.00 | 0.00 | H |
| ATOM | 17 | HD12 | LEU | E | 17 | −6.372 | −7.687 | 10.576 | 1.00 | 0.00 | H |
| ATOM | 18 | HD13 | LEU | E | 17 | −6.304 | −7.337 | 8.802 | 1.00 | 0.00 | H |
| ATOM | 19 | HD21 | LEU | E | 17 | −9.283 | −8.433 | 8.356 | 1.00 | 0.00 | H |
| ATOM | 20 | HD22 | LEU | E | 17 | −7.942 | −8.747 | 7.195 | 1.00 | 0.00 | H |
| ATOM | 21 | HD23 | LEU | E | 17 | −8.844 | −10.122 | 7.930 | 1.00 | 0.00 | H |
| ATOM | 22 | N | VAL | E | 18 | −5.424 | −12.964 | 9.972 | 1.00 | 0.00 | N |
| ATOM | 23 | CA | VAL | E | 18 | −4.953 | −14.332 | 9.721 | 1.00 | 0.00 | C |
| ATOM | 24 | C | VAL | E | 18 | −4.942 | −14.537 | 8.195 | 1.00 | 0.00 | C |
| ATOM | 25 | O | VAL | E | 18 | −5.993 | −14.639 | 7.554 | 1.00 | 0.00 | O |
| ATOM | 26 | CB | VAL | E | 18 | −5.740 | −15.453 | 10.461 | 1.00 | 0.00 | C |
| ATOM | 27 | CG1 | VAL | E | 18 | −5.106 | −16.852 | 10.206 | 1.00 | 0.00 | C |
| ATOM | 28 | CG2 | VAL | E | 18 | −5.825 | −15.184 | 11.990 | 1.00 | 0.00 | C |
| ATOM | 29 | HN | VAL | E | 18 | −6.412 | −12.896 | 10.080 | 1.00 | 0.00 | H |
| ATOM | 30 | HA | VAL | E | 18 | −3.933 | −14.389 | 10.082 | 1.00 | 0.00 | H |
| ATOM | 31 | HB | VAL | E | 18 | −6.781 | −15.475 | 10.063 | 1.00 | 0.00 | H |
| ATOM | 32 | HG11 | VAL | E | 18 | −5.679 | −17.636 | 10.745 | 1.00 | 0.00 | H |
| ATOM | 33 | HG12 | VAL | E | 18 | −5.126 | −17.113 | 9.127 | 1.00 | 0.00 | H |
| ATOM | 34 | HG13 | VAL | E | 18 | −4.054 | −16.887 | 10.561 | 1.00 | 0.00 | H |
| ATOM | 35 | HG21 | VAL | E | 18 | −6.395 | −15.996 | 12.491 | 1.00 | 0.00 | H |
| ATOM | 36 | HG22 | VAL | E | 18 | −4.811 | −15.143 | 12.443 | 1.00 | 0.00 | H |
| ATOM | 37 | HG23 | VAL | E | 18 | −6.346 | −14.228 | 12.203 | 1.00 | 0.00 | H |
| ATOM | 38 | N | PHE | E | 19 | −3.722 | −14.584 | 7.596 | 1.00 | 0.00 | N |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 39 | CA | PHE | E | 19 | −3.476 | −14.796 | 6.177 | 1.00 | 0.00 | C |
| ATOM | 40 | C | PHE | E | 19 | −3.187 | −16.283 | 5.942 | 1.00 | 0.00 | C |
| ATOM | 41 | O | PHE | E | 19 | −2.095 | −16.776 | 6.243 | 1.00 | 0.00 | O |
| ATOM | 42 | CB | PHE | E | 19 | −2.318 | −13.880 | 5.682 | 1.00 | 0.00 | C |
| ATOM | 43 | CG | PHE | E | 19 | −2.186 | −13.850 | 4.177 | 1.00 | 0.00 | C |
| ATOM | 44 | CD1 | PHE | E | 19 | −2.922 | −12.924 | 3.413 | 1.00 | 0.00 | C |
| ATOM | 45 | CD2 | PHE | E | 19 | −1.293 | −14.712 | 3.515 | 1.00 | 0.00 | C |
| ATOM | 46 | CE1 | PHE | E | 19 | −2.769 | −12.862 | 2.022 | 1.00 | 0.00 | C |
| ATOM | 47 | CE2 | PHE | E | 19 | −1.130 | −14.644 | 2.126 | 1.00 | 0.00 | C |
| ATOM | 48 | CZ | PHE | E | 19 | −1.871 | −13.721 | 1.379 | 1.00 | 0.00 | C |
| ATOM | 49 | HN | PHE | E | 19 | −2.899 | −14.472 | 8.145 | 1.00 | 0.00 | H |
| ATOM | 50 | HA | PHE | E | 19 | −4.374 | −14.519 | 5.636 | 1.00 | 0.00 | H |
| ATOM | 51 | HB2 | PHE | E | 19 | −2.509 | −12.835 | 6.008 | 1.00 | 0.00 | H |
| ATOM | 52 | HB3 | PHE | E | 19 | −1.350 | −14.202 | 6.121 | 1.00 | 0.00 | H |
| ATOM | 53 | HD1 | PHE | E | 19 | −3.604 | −12.243 | 3.901 | 1.00 | 0.00 | H |
| ATOM | 54 | HD2 | PHE | E | 19 | −0.719 | −15.434 | 4.080 | 1.00 | 0.00 | H |
| ATOM | 55 | HE1 | PHE | E | 19 | −3.337 | −12.145 | 1.447 | 1.00 | 0.00 | H |
| ATOM | 56 | HE2 | PHE | E | 19 | −0.430 | −15.302 | 1.632 | 1.00 | 0.00 | H |
| ATOM | 57 | HZ | PHE | E | 19 | −1.746 | −13.671 | 0.307 | 1.00 | 0.00 | H |
| ATOM | 58 | N | PHE | E | 20 | −4.188 | −17.030 | 5.405 | 1.00 | 0.00 | N |
| ATOM | 59 | CA | PHE | E | 20 | −4.165 | −18.482 | 5.235 | 1.00 | 0.00 | C |
| ATOM | 60 | C | PHE | E | 20 | −3.313 | −18.915 | 4.027 | 1.00 | 0.00 | C |
| ATOM | 61 | O | PHE | E | 20 | −3.832 | −19.325 | 2.985 | 1.00 | 0.00 | O |
| ATOM | 62 | CB | PHE | E | 20 | −5.608 | −19.088 | 5.165 | 1.00 | 0.00 | C |
| ATOM | 63 | CG | PHE | E | 20 | −6.384 | −18.903 | 6.453 | 1.00 | 0.00 | C |
| ATOM | 64 | CD1 | PHE | E | 20 | −7.240 | −17.798 | 6.628 | 1.00 | 0.00 | C |
| ATOM | 65 | CD2 | PHE | E | 20 | −6.277 | −19.845 | 7.494 | 1.00 | 0.00 | C |
| ATOM | 66 | CE1 | PHE | E | 20 | −7.970 | −17.638 | 7.813 | 1.00 | 0.00 | C |
| ATOM | 67 | CE2 | PHE | E | 20 | −7.010 | −19.689 | 8.678 | 1.00 | 0.00 | C |
| ATOM | 68 | CZ | PHE | E | 20 | −7.858 | −18.586 | 8.836 | 1.00 | 0.00 | C |
| ATOM | 69 | HN | PHE | E | 20 | −5.048 | −16.597 | 5.154 | 1.00 | 0.00 | H |
| ATOM | 70 | HA | PHE | E | 20 | −3.690 | −18.900 | 6.114 | 1.00 | 0.00 | H |
| ATOM | 71 | HB2 | PHE | E | 20 | −6.180 | −18.626 | 4.331 | 1.00 | 0.00 | H |
| ATOM | 72 | HB3 | PHE | E | 20 | −5.547 | −20.180 | 4.967 | 1.00 | 0.00 | H |
| ATOM | 73 | HD1 | PHE | E | 20 | −7.341 | −17.060 | 5.846 | 1.00 | 0.00 | H |
| ATOM | 74 | HD2 | PHE | E | 20 | −5.629 | −20.702 | 7.382 | 1.00 | 0.00 | H |
| ATOM | 75 | HE1 | PHE | E | 20 | −8.617 | −16.782 | 7.935 | 1.00 | 0.00 | H |
| ATOM | 76 | HE2 | PHE | E | 20 | −6.922 | −20.421 | 9.468 | 1.00 | 0.00 | H |
| ATOM | 77 | HZ | PHE | E | 20 | −8.422 | −18.464 | 9.750 | 1.00 | 0.00 | H |
| ATOM | 78 | N | ALA | E | 21 | −1.962 | −18.826 | 4.174 | 1.00 | 0.00 | N |
| ATOM | 79 | CA | ALA | E | 21 | −0.961 | −19.299 | 3.227 | 1.00 | 0.00 | C |
| ATOM | 80 | C | ALA | E | 21 | 0.265 | −19.892 | 3.935 | 1.00 | 0.00 | C |
| ATOM | 81 | O | ALA | E | 21 | 0.658 | −19.456 | 5.022 | 1.00 | 0.00 | O |
| ATOM | 82 | CB | ALA | E | 21 | −0.506 | −18.178 | 2.263 | 1.00 | 0.00 | C |
| ATOM | 83 | HN | ALA | E | 21 | −1.593 | −18.392 | 4.999 | 1.00 | 0.00 | H |
| ATOM | 84 | HA | ALA | E | 21 | −1.420 | −20.086 | 2.641 | 1.00 | 0.00 | H |
| ATOM | 85 | HB1 | ALA | E | 21 | 0.004 | −17.364 | 2.821 | 1.00 | 0.00 | H |
| ATOM | 86 | HB2 | ALA | E | 21 | 0.203 | −18.574 | 1.505 | 1.00 | 0.00 | H |
| ATOM | 87 | HB3 | ALA | E | 21 | −1.381 | −17.749 | 1.731 | 1.00 | 0.00 | H |
| ATOM | 88 | N | GLU | E | 22 | 0.889 | −20.915 | 3.294 | 1.00 | 0.00 | N |
| ATOM | 89 | CA | GLU | E | 22 | 2.127 | −21.571 | 3.695 | 1.00 | 0.00 | C |
| ATOM | 90 | C | GLU | E | 22 | 2.991 | −21.853 | 2.456 | 1.00 | 0.00 | C |
| ATOM | 91 | O | GLU | E | 22 | 2.485 | −22.046 | 1.343 | 1.00 | 0.00 | O |
| ATOM | 92 | CB | GLU | E | 22 | 1.869 | −22.866 | 4.533 | 1.00 | 0.00 | C |
| ATOM | 93 | CG | GLU | E | 22 | 3.110 | −23.651 | 5.058 | 1.00 | 0.00 | C |
| ATOM | 94 | CD | GLU | E | 22 | 4.098 | −22.807 | 5.870 | 1.00 | 0.00 | C |
| ATOM | 95 | OE1 | GLU | E | 22 | 4.107 | −22.938 | 7.119 | 1.00 | 0.00 | O1− |
| ATOM | 96 | OE2 | GLU | E | 22 | 4.857 | −22.025 | 5.232 | 1.00 | 0.00 | O |
| ATOM | 97 | HN | GLU | E | 22 | 0.553 | −21.237 | 2.412 | 1.00 | 0.00 | H |
| ATOM | 98 | HA | GLU | E | 22 | 2.673 | −20.873 | 4.318 | 1.00 | 0.00 | H |
| ATOM | 99 | HB2 | GLU | E | 22 | 1.263 | −22.574 | 5.421 | 1.00 | 0.00 | H |
| ATOM | 100 | HB3 | GLU | E | 22 | 1.253 | −23.567 | 3.929 | 1.00 | 0.00 | H |
| ATOM | 101 | HG2 | GLU | E | 22 | 2.758 | −24.477 | 5.711 | 1.00 | 0.00 | H |
| ATOM | 102 | HG3 | GLU | E | 22 | 3.668 | −24.105 | 4.214 | 1.00 | 0.00 | H |
| ATOM | 103 | N | ASP | E | 23 | 4.330 | −21.871 | 2.667 | 1.00 | 0.00 | N |
| ATOM | 104 | CA | ASP | E | 23 | 5.370 | −22.061 | 1.667 | 1.00 | 0.00 | C |
| ATOM | 105 | C | ASP | E | 23 | 6.435 | −22.990 | 2.332 | 1.00 | 0.00 | C |
| ATOM | 106 | O | ASP | E | 23 | 6.210 | −23.825 | 1.448 | 1.00 | 0.00 | O |
| ATOM | 107 | CB | ASP | E | 23 | 6.040 | −20.683 | 1.370 | 1.00 | 0.00 | C |
| ATOM | 108 | CG | ASP | E | 23 | 6.797 | −20.649 | 0.046 | 1.00 | 0.00 | C |
| ATOM | 109 | OD1 | ASP | E | 23 | 7.643 | −21.546 | −0.204 | 1.00 | 0.00 | O1− |
| ATOM | 110 | OD2 | ASP | E | 23 | 6.537 | −19.695 | −0.736 | 1.00 | 0.00 | O |
| ATOM | 111 | HN | ASP | E | 23 | 4.638 | −21.817 | 3.645 | 1.00 | 0.00 | H |
| ATOM | 112 | HA | ASP | E | 23 | 4.879 | −22.397 | 0.748 | 1.00 | 0.00 | H |
| ATOM | 113 | HB2 | ASP | E | 23 | 5.239 | −19.918 | 1.301 | 1.00 | 0.00 | H |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 114 | HB3 | ASP | E | 23 | 6.728 | −20.384 | 2.185 | 1.00 | 0.00 | H |
| ATOM | 115 | N | VAL | E | 24 | 7.231 | −24.037 | 2.574 | 1.00 | 0.00 | N |
| ATOM | 116 | CA | VAL | E | 24 | 8.168 | −24.125 | 3.703 | 1.00 | 0.00 | C |
| ATOM | 117 | C | VAL | E | 24 | 9.537 | −24.715 | 3.298 | 1.00 | 0.00 | C |
| ATOM | 118 | O | VAL | E | 24 | 10.575 | −24.135 | 3.628 | 1.00 | 0.00 | O |
| ATOM | 119 | CB | VAL | E | 24 | 7.544 | −24.791 | 4.968 | 1.00 | 0.00 | C |
| ATOM | 120 | CG1 | VAL | E | 24 | 8.427 | −24.572 | 6.227 | 1.00 | 0.00 | C |
| ATOM | 121 | CG2 | VAL | E | 24 | 7.165 | −26.285 | 4.774 | 1.00 | 0.00 | C |
| ATOM | 122 | HN | VAL | E | 24 | 7.136 | −24.802 | 1.922 | 1.00 | 0.00 | H |
| ATOM | 123 | HA | VAL | E | 24 | 8.382 | −23.101 | 3.985 | 1.00 | 0.00 | H |
| ATOM | 124 | HB | VAL | E | 24 | 6.587 | −24.245 | 5.166 | 1.00 | 0.00 | H |
| ATOM | 125 | HG11 | VAL | E | 24 | 7.907 | −24.960 | 7.128 | 1.00 | 0.00 | H |
| ATOM | 126 | HG12 | VAL | E | 24 | 8.621 | −23.490 | 6.387 | 1.00 | 0.00 | H |
| ATOM | 127 | HG13 | VAL | E | 24 | 9.400 | −25.099 | 6.131 | 1.00 | 0.00 | H |
| ATOM | 128 | HG21 | VAL | E | 24 | 6.624 | −26.658 | 5.670 | 1.00 | 0.00 | H |
| ATOM | 129 | HG22 | VAL | E | 24 | 6.494 | −26.404 | 3.898 | 1.00 | 0.00 | H |
| ATOM | 130 | HG23 | VAL | E | 24 | 8.068 | −26.914 | 4.628 | 1.00 | 0.00 | H |
| ATOM | 131 | N | GLY | E | 25 | 9.571 | −25.782 | 2.570 | 1.00 | 0.00 | N |
| ATOM | 132 | CA | GLY | E | 25 | 10.728 | −26.711 | 2.245 | 1.00 | 0.00 | C |
| ATOM | 133 | C | GLY | E | 25 | 11.732 | −26.887 | 3.369 | 1.00 | 0.00 | C |
| ATOM | 134 | O | GLY | E | 25 | 11.461 | −27.541 | 4.381 | 1.00 | 0.00 | O |
| ATOM | 135 | HN | GLY | E | 25 | 8.703 | −26.152 | 2.117 | 1.00 | 0.00 | H |
| ATOM | 136 | HA2 | GLY | E | 25 | 10.344 | −27.695 | 2.018 | 1.00 | 0.00 | H |
| ATOM | 137 | HA3 | GLY | E | 25 | 11.215 | −26.256 | 1.394 | 1.00 | 0.00 | H |
| ATOM | 138 | N | SER | E | 26 | 12.939 | −26.294 | 3.198 | 1.00 | 0.00 | N |
| ATOM | 139 | CA | SER | E | 26 | 13.972 | −26.116 | 4.226 | 1.00 | 0.00 | C |
| ATOM | 140 | C | SER | E | 26 | 14.983 | −25.119 | 3.655 | 1.00 | 0.00 | C |
| ATOM | 141 | O | SER | E | 26 | 16.115 | −25.473 | 3.305 | 1.00 | 0.00 | O |
| ATOM | 142 | CB | SER | E | 26 | 14.653 | −27.454 | 4.655 | 1.00 | 0.00 | C |
| ATOM | 143 | OG | SER | E | 26 | 13.746 | −28.270 | 5.393 | 1.00 | 0.00 | O |
| ATOM | 144 | HN | SER | E | 26 | 13.143 | −25.862 | 2.316 | 1.00 | 0.00 | H |
| ATOM | 145 | HA | SER | E | 26 | 13.512 | −25.665 | 5.095 | 1.00 | 0.00 | H |
| ATOM | 146 | HB2 | SER | E | 26 | 14.987 | −28.007 | 3.751 | 1.00 | 0.00 | H |
| ATOM | 147 | HB3 | SER | E | 26 | 15.537 | −27.247 | 5.297 | 1.00 | 0.00 | H |
| ATOM | 148 | HG | SER | E | 26 | 12.849 | −28.037 | 5.051 | 1.00 | 0.00 | H |
| ATOM | 149 | N | ASN | E | 27 | 14.542 | −23.833 | 3.507 | 1.00 | 0.00 | N |
| ATOM | 150 | CA | ASN | E | 27 | 15.010 | −22.894 | 2.483 | 1.00 | 0.00 | C |
| ATOM | 151 | C | ASN | E | 27 | 14.612 | −23.372 | 1.059 | 1.00 | 0.00 | C |
| ATOM | 152 | O | ASN | E | 27 | 14.216 | −24.523 | 0.833 | 1.00 | 0.00 | O |
| ATOM | 153 | CB | ASN | E | 27 | 16.529 | −22.500 | 2.633 | 1.00 | 0.00 | C |
| ATOM | 154 | CG | ASN | E | 27 | 16.990 | −21.234 | 1.884 | 1.00 | 0.00 | C |
| ATOM | 155 | OD1 | ASN | E | 27 | 16.265 | −20.531 | 1.173 | 1.00 | 0.00 | O |
| ATOM | 156 | ND2 | ASN | E | 27 | 18.302 | −20.924 | 2.051 | 1.00 | 0.00 | N |
| ATOM | 157 | HN | ASN | E | 27 | 13.700 | −23.565 | 3.970 | 1.00 | 0.00 | H |
| ATOM | 158 | HA | ASN | E | 27 | 14.436 | −21.994 | 2.667 | 1.00 | 0.00 | H |
| ATOM | 159 | HB2 | ASN | E | 27 | 16.730 | −22.330 | 3.713 | 1.00 | 0.00 | H |
| ATOM | 160 | HB3 | ASN | E | 27 | 17.156 | −23.355 | 2.302 | 1.00 | 0.00 | H |
| ATOM | 161 | HD21 | ASN | E | 27 | 18.883 | −21.499 | 2.621 | 1.00 | 0.00 | H |
| ATOM | 162 | HD22 | ASN | E | 27 | 18.654 | −20.116 | 1.585 | 1.00 | 0.00 | H |
| ATOM | 163 | N | LYS | E | 28 | 14.695 | −22.445 | 0.075 | 1.00 | 0.00 | N |
| ATOM | 164 | CA | LYS | E | 28 | 14.381 | −22.629 | −1.341 | 1.00 | 0.00 | C |
| ATOM | 165 | C | LYS | E | 28 | 15.351 | −21.770 | −2.154 | 1.00 | 0.00 | C |
| ATOM | 166 | O | LYS | E | 28 | 16.222 | −22.307 | −2.839 | 1.00 | 0.00 | O |
| ATOM | 167 | CB | LYS | E | 28 | 12.877 | −22.355 | −1.687 | 1.00 | 0.00 | C |
| ATOM | 168 | CG | LYS | E | 28 | 11.905 | −23.328 | −0.984 | 1.00 | 0.00 | C |
| ATOM | 169 | CD | LYS | E | 28 | 10.407 | −23.125 | −1.274 | 1.00 | 0.00 | C |
| ATOM | 170 | CE | LYS | E | 28 | 9.565 | −24.127 | −0.470 | 1.00 | 0.00 | C |
| ATOM | 171 | NZ | LYS | E | 28 | 8.121 | −23.991 | −0.712 | 1.00 | 0.00 | N1+ |
| ATOM | 172 | HN | LYS | E | 28 | 15.075 | −21.548 | 0.336 | 1.00 | 0.00 | H |
| ATOM | 173 | HA | LYS | E | 28 | 14.600 | −23.660 | −1.591 | 1.00 | 0.00 | H |
| ATOM | 174 | HB2 | LYS | E | 28 | 12.608 | −21.320 | −1.392 | 1.00 | 0.00 | H |
| ATOM | 175 | HB3 | LYS | E | 28 | 12.733 | −22.451 | −2.786 | 1.00 | 0.00 | H |
| ATOM | 176 | HG2 | LYS | E | 28 | 12.188 | −24.371 | −1.257 | 1.00 | 0.00 | H |
| ATOM | 177 | HG3 | LYS | E | 28 | 12.040 | −23.226 | 0.118 | 1.00 | 0.00 | H |
| ATOM | 178 | HD2 | LYS | E | 28 | 10.112 | −22.090 | −0.985 | 1.00 | 0.00 | H |
| ATOM | 179 | HD3 | LYS | E | 28 | 10.218 | −23.245 | −2.362 | 1.00 | 0.00 | H |
| ATOM | 180 | HE2 | LYS | E | 28 | 9.855 | −25.173 | −0.714 | 1.00 | 0.00 | H |
| ATOM | 181 | HE3 | LYS | E | 28 | 9.735 | −23.955 | 0.615 | 1.00 | 0.00 | H |
| ATOM | 182 | HZ1 | LYS | E | 28 | 7.642 | −24.701 | −0.075 | 1.00 | 0.00 | H |
| ATOM | 183 | HZ2 | LYS | E | 28 | 7.824 | −22.985 | −0.460 | 1.00 | 0.00 | H |
| ATOM | 184 | HZ3 | LYS | E | 28 | 7.862 | −24.209 | −1.698 | 1.00 | 0.00 | H |
| ATOM | 185 | N | GLY | E | 29 | 15.238 | −20.414 | −2.069 | 1.00 | 0.00 | N |
| ATOM | 186 | CA | GLY | E | 29 | 16.221 | −19.472 | −2.602 | 1.00 | 0.00 | C |
| ATOM | 187 | C | GLY | E | 29 | 16.329 | −18.178 | −1.820 | 1.00 | 0.00 | C |
| ATOM | 188 | O | GLY | E | 29 | 16.342 | −17.105 | −2.425 | 1.00 | 0.00 | O |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 189 | HN | GLY | E | 29 | 14.466 | −20.019 | −1.577 | 1.00 | 0.00 | H |
| ATOM | 190 | HA2 | GLY | E | 29 | 17.197 | −19.939 | −2.578 | 1.00 | 0.00 | H |
| ATOM | 191 | HA3 | GLY | E | 29 | 15.907 | −19.224 | −3.607 | 1.00 | 0.00 | H |
| ATOM | 192 | N | ALA | E | 30 | 16.422 | −18.252 | −0.458 | 1.00 | 0.00 | N |
| ATOM | 193 | CA | ALA | E | 30 | 16.545 | −17.145 | 0.489 | 1.00 | 0.00 | C |
| ATOM | 194 | C | ALA | E | 30 | 15.354 | −16.174 | 0.492 | 1.00 | 0.00 | C |
| ATOM | 195 | O | ALA | E | 30 | 14.532 | −16.217 | 1.409 | 1.00 | 0.00 | O |
| ATOM | 196 | CB | ALA | E | 30 | 17.924 | −16.432 | 0.416 | 1.00 | 0.00 | C |
| ATOM | 197 | HN | ALA | E | 30 | 16.394 | −19.157 | −0.010 | 1.00 | 0.00 | H |
| ATOM | 198 | HA | ALA | E | 30 | 16.518 | −17.620 | 1.461 | 1.00 | 0.00 | H |
| ATOM | 199 | HB1 | ALA | E | 30 | 18.057 | −15.934 | −0.568 | 1.00 | 0.00 | H |
| ATOM | 200 | HB2 | ALA | E | 30 | 18.013 | −15.667 | 1.216 | 1.00 | 0.00 | H |
| ATOM | 201 | HB3 | ALA | E | 30 | 18.745 | −17.169 | 0.545 | 1.00 | 0.00 | H |
| ATOM | 202 | N | ILE | E | 31 | 15.230 | −15.285 | −0.535 | 1.00 | 0.00 | N |
| ATOM | 203 | CA | ILE | E | 31 | 14.218 | −14.224 | −0.629 | 1.00 | 0.00 | C |
| ATOM | 204 | C | ILE | E | 31 | 12.989 | −14.791 | −1.375 | 1.00 | 0.00 | C |
| ATOM | 205 | O | ILE | E | 31 | 12.672 | −14.414 | −2.507 | 1.00 | 0.00 | O |
| ATOM | 206 | CB | ILE | E | 31 | 14.773 | −12.883 | −1.203 | 1.00 | 0.00 | C |
| ATOM | 207 | CG1 | ILE | E | 31 | 16.143 | −12.433 | −0.582 | 1.00 | 0.00 | C |
| ATOM | 208 | CG2 | ILE | E | 31 | 13.711 | −11.745 | −1.112 | 1.00 | 0.00 | C |
| ATOM | 209 | CD1 | ILE | E | 31 | 16.172 | −12.182 | 0.938 | 1.00 | 0.00 | C |
| ATOM | 210 | HN | ILE | E | 31 | 15.848 | −15.388 | −1.317 | 1.00 | 0.00 | H |
| ATOM | 211 | HA | ILE | E | 31 | 13.897 | −14.006 | 0.382 | 1.00 | 0.00 | H |
| ATOM | 212 | HB | ILE | E | 31 | 14.972 | −13.051 | −2.289 | 1.00 | 0.00 | H |
| ATOM | 213 | HG12 | ILE | E | 31 | 16.911 | −13.200 | −0.825 | 1.00 | 0.00 | H |
| ATOM | 214 | HG13 | ILE | E | 31 | 16.462 | −11.498 | −1.097 | 1.00 | 0.00 | H |
| ATOM | 215 | HG21 | ILE | E | 31 | 13.430 | −11.548 | −0.056 | 1.00 | 0.00 | H |
| ATOM | 216 | HG22 | ILE | E | 31 | 14.122 | −10.808 | −1.543 | 1.00 | 0.00 | H |
| ATOM | 217 | HG23 | ILE | E | 31 | 12.794 | −12.002 | −1.681 | 1.00 | 0.00 | H |
| ATOM | 218 | HD11 | ILE | E | 31 | 15.913 | −13.106 | 1.499 | 1.00 | 0.00 | H |
| ATOM | 219 | HD12 | ILE | E | 31 | 17.189 | −11.863 | 1.253 | 1.00 | 0.00 | H |
| ATOM | 220 | HD13 | ILE | E | 31 | 15.456 | −11.383 | 1.222 | 1.00 | 0.00 | H |
| ATOM | 221 | N | ILE | E | 32 | 12.276 | −15.746 | −0.715 | 1.00 | 0.00 | N |
| ATOM | 222 | CA | ILE | E | 32 | 11.097 | −16.464 | −1.206 | 1.00 | 0.00 | C |
| ATOM | 223 | C | ILE | E | 32 | 10.373 | −17.088 | −0.006 | 1.00 | 0.00 | C |
| ATOM | 224 | O | ILE | E | 32 | 10.993 | −17.721 | 0.856 | 1.00 | 0.00 | O |
| ATOM | 225 | CB | ILE | E | 32 | 11.393 | −17.479 | −2.356 | 1.00 | 0.00 | C |
| ATOM | 226 | CG1 | ILE | E | 32 | 10.127 | −18.060 | −3.076 | 1.00 | 0.00 | C |
| ATOM | 227 | CG2 | ILE | E | 32 | 12.450 | −18.553 | −1.962 | 1.00 | 0.00 | C |
| ATOM | 228 | CD1 | ILE | E | 32 | 9.433 | −19.286 | −2.452 | 1.00 | 0.00 | C |
| ATOM | 229 | HN | ILE | E | 32 | 12.602 | −16.048 | 0.185 | 1.00 | 0.00 | H |
| ATOM | 230 | HA | ILE | E | 32 | 10.449 | −15.702 | −1.620 | 1.00 | 0.00 | H |
| ATOM | 231 | HB | ILE | E | 32 | 11.890 | −16.860 | −3.146 | 1.00 | 0.00 | H |
| ATOM | 232 | HG12 | ILE | E | 32 | 9.378 | −17.249 | −3.211 | 1.00 | 0.00 | H |
| ATOM | 233 | HG13 | ILE | E | 32 | 10.447 | −18.361 | −4.101 | 1.00 | 0.00 | H |
| ATOM | 234 | HG21 | ILE | E | 32 | 13.389 | −18.065 | −1.627 | 1.00 | 0.00 | H |
| ATOM | 235 | HG22 | ILE | E | 32 | 12.064 | −19.187 | −1.136 | 1.00 | 0.00 | H |
| ATOM | 236 | HG23 | ILE | E | 32 | 12.676 | −19.197 | −2.837 | 1.00 | 0.00 | H |
| ATOM | 237 | HD11 | ILE | E | 32 | 10.124 | −20.154 | −2.407 | 1.00 | 0.00 | H |
| ATOM | 238 | HD12 | ILE | E | 32 | 9.064 | −19.088 | −1.426 | 1.00 | 0.00 | H |
| ATOM | 239 | HD13 | ILE | E | 32 | 8.554 | −19.585 | −3.062 | 1.00 | 0.00 | H |
| ATOM | 240 | N | GLY | E | 33 | 9.029 | −16.901 | 0.075 | 1.00 | 0.00 | N |
| ATOM | 241 | CA | GLY | E | 33 | 8.210 | −17.456 | 1.144 | 1.00 | 0.00 | C |
| ATOM | 242 | C | GLY | E | 33 | 6.829 | −16.852 | 1.184 | 1.00 | 0.00 | C |
| ATOM | 243 | O | GLY | E | 33 | 6.600 | −15.880 | 1.908 | 1.00 | 0.00 | O |
| ATOM | 244 | HN | GLY | E | 33 | 8.548 | −16.391 | 0.632 | 1.00 | 0.00 | H |
| ATOM | 245 | HA2 | GLY | E | 33 | 8.131 | −18.520 | 0.977 | 1.00 | 0.00 | H |
| ATOM | 246 | HA3 | GLY | E | 33 | 8.691 | −17.222 | 2.083 | 1.00 | 0.00 | H |
| ATOM | 247 | N | LEU | E | 34 | 5.864 | −17.435 | 0.423 | 1.00 | 0.00 | N |
| ATOM | 248 | CA | LEU | E | 34 | 4.456 | −17.032 | 0.382 | 1.00 | 0.00 | C |
| ATOM | 249 | C | LEU | E | 34 | 3.710 | −17.618 | 1.602 | 1.00 | 0.00 | C |
| ATOM | 250 | O | LEU | E | 34 | 2.849 | −18.495 | 1.492 | 1.00 | 0.00 | O |
| ATOM | 251 | CB | LEU | E | 34 | 3.807 | −17.395 | −0.999 | 1.00 | 0.00 | C |
| ATOM | 252 | CG | LEU | E | 34 | 2.606 | −16.518 | −1.483 | 1.00 | 0.00 | C |
| ATOM | 253 | CD1 | LEU | E | 34 | 2.248 | −16.841 | −2.954 | 1.00 | 0.00 | C |
| ATOM | 254 | CD2 | LEU | E | 34 | 1.347 | −16.601 | −0.591 | 1.00 | 0.00 | C |
| ATOM | 255 | HN | LEU | E | 34 | 6.101 | −18.272 | −0.128 | 1.00 | 0.00 | H |
| ATOM | 256 | HA | LEU | E | 34 | 4.439 | −15.953 | 0.474 | 1.00 | 0.00 | H |
| ATOM | 257 | HB2 | LEU | E | 34 | 4.604 | −17.288 | −1.771 | 1.00 | 0.00 | H |
| ATOM | 258 | HB3 | LEU | E | 34 | 3.517 | −18.468 | −1.000 | 1.00 | 0.00 | H |
| ATOM | 259 | HG | LEU | E | 34 | 2.950 | −15.455 | −1.466 | 1.00 | 0.00 | H |
| ATOM | 260 | HD11 | LEU | E | 34 | 1.898 | −17.891 | −3.047 | 1.00 | 0.00 | H |
| ATOM | 261 | HD12 | LEU | E | 34 | 1.446 | −16.167 | −3.320 | 1.00 | 0.00 | H |
| ATOM | 262 | HD13 | LEU | E | 34 | 3.136 | −16.709 | −3.608 | 1.00 | 0.00 | H |
| ATOM | 263 | HD21 | LEU | E | 34 | 1.569 | −16.255 | 0.440 | 1.00 | 0.00 | H |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 264 | HD22 | LEU | E | 34 | 0.532 | −15.965 | −0.996 | 1.00 | 0.00 | H |
| ATOM | 265 | HD23 | LEU | E | 34 | 0.984 | −17.650 | −0.534 | 1.00 | 0.00 | H |
| ATOM | 266 | N | MET | E | 35 | 4.075 | −17.119 | 2.814 | 1.00 | 0.00 | N |
| ATOM | 267 | CA | MET | E | 35 | 3.624 | −17.583 | 4.123 | 1.00 | 0.00 | C |
| ATOM | 268 | C | MET | E | 35 | 2.523 | −16.670 | 4.714 | 1.00 | 0.00 | C |
| ATOM | 269 | O | MET | E | 35 | 1.822 | −15.947 | 3.995 | 1.00 | 0.00 | O |
| ATOM | 270 | CB | MET | E | 35 | 4.861 | −17.768 | 5.073 | 1.00 | 0.00 | C |
| ATOM | 271 | CG | MET | E | 35 | 5.942 | −18.759 | 4.568 | 1.00 | 0.00 | C |
| ATOM | 272 | SD | MET | E | 35 | 7.383 | −18.952 | 5.668 | 1.00 | 0.00 | S |
| ATOM | 273 | CE | MET | E | 35 | 8.170 | −17.332 | 5.411 | 1.00 | 0.00 | C |
| ATOM | 274 | HN | MET | E | 35 | 4.792 | −16.420 | 2.823 | 1.00 | 0.00 | H |
| ATOM | 275 | HA | MET | E | 35 | 3.166 | −18.555 | 3.990 | 1.00 | 0.00 | H |
| ATOM | 276 | HB2 | MET | E | 35 | 5.330 | −16.775 | 5.244 | 1.00 | 0.00 | H |
| ATOM | 277 | HB3 | MET | E | 35 | 4.519 | −18.161 | 6.055 | 1.00 | 0.00 | H |
| ATOM | 278 | HG2 | MET | E | 35 | 5.456 | −19.752 | 4.443 | 1.00 | 0.00 | H |
| ATOM | 279 | HG3 | MET | E | 35 | 6.290 | −18.447 | 3.561 | 1.00 | 0.00 | H |
| ATOM | 280 | HE1 | MET | E | 35 | 8.373 | −17.150 | 4.334 | 1.00 | 0.00 | H |
| ATOM | 281 | HE2 | MET | E | 35 | 7.526 | −16.507 | 5.783 | 1.00 | 0.00 | H |
| ATOM | 282 | HE3 | MET | E | 35 | 9.138 | −17.276 | 5.953 | 1.00 | 0.00 | H |
| ATOM | 283 | N | VAL | E | 36 | 2.330 | −16.695 | 6.067 | 1.00 | 0.00 | N |
| ATOM | 284 | CA | VAL | E | 36 | 1.301 | −15.972 | 6.822 | 1.00 | 0.00 | C |
| ATOM | 285 | C | VAL | E | 36 | 1.640 | −14.462 | 6.866 | 1.00 | 0.00 | C |
| ATOM | 286 | O | VAL | E | 36 | 2.086 | −13.905 | 7.875 | 1.00 | 0.00 | O |
| ATOM | 287 | CB | VAL | E | 36 | 1.004 | −16.594 | 8.226 | 1.00 | 0.00 | C |
| ATOM | 288 | CG1 | VAL | E | 36 | −0.158 | −15.864 | 8.962 | 1.00 | 0.00 | C |
| ATOM | 289 | CG2 | VAL | E | 36 | 0.676 | −18.113 | 8.129 | 1.00 | 0.00 | C |
| ATOM | 290 | HN | VAL | E | 36 | 2.894 | −17.297 | 6.623 | 1.00 | 0.00 | H |
| ATOM | 291 | HA | VAL | E | 36 | 0.386 | −16.074 | 6.251 | 1.00 | 0.00 | H |
| ATOM | 292 | HB | VAL | E | 36 | 1.921 | −16.486 | 8.850 | 1.00 | 0.00 | H |
| ATOM | 293 | HG11 | VAL | E | 36 | 0.075 | −14.792 | 9.128 | 1.00 | 0.00 | H |
| ATOM | 294 | HG12 | VAL | E | 36 | −1.101 | −15.941 | 8.383 | 1.00 | 0.00 | H |
| ATOM | 295 | HG13 | VAL | E | 36 | −0.326 | −16.326 | 9.958 | 1.00 | 0.00 | H |
| ATOM | 296 | HG21 | VAL | E | 36 | 0.481 | −18.535 | 9.137 | 1.00 | 0.00 | H |
| ATOM | 297 | HG22 | VAL | E | 36 | −0.224 | −18.282 | 7.499 | 1.00 | 0.00 | H |
| ATOM | 298 | HG23 | VAL | E | 36 | 1.517 | −18.684 | 7.683 | 1.00 | 0.00 | H |
| ATOM | 299 | N | GLY | E | 37 | 1.403 | −13.749 | 5.730 | 1.00 | 0.00 | N |
| ATOM | 300 | CA | GLY | E | 37 | 1.476 | −12.292 | 5.611 | 1.00 | 0.00 | C |
| ATOM | 301 | C | GLY | E | 37 | 0.283 | −11.611 | 6.248 | 1.00 | 0.00 | C |
| ATOM | 302 | O | GLY | E | 37 | −0.559 | −11.032 | 5.560 | 1.00 | 0.00 | O |
| ATOM | 303 | HN | GLY | E | 37 | 1.196 | −14.271 | 4.895 | 1.00 | 0.00 | H |
| ATOM | 304 | HA2 | GLY | E | 37 | 2.377 | −11.951 | 6.105 | 1.00 | 0.00 | H |
| ATOM | 305 | HA3 | GLY | E | 37 | 1.465 | −12.057 | 4.556 | 1.00 | 0.00 | H |
| ATOM | 306 | N | GLY | E | 37 | 0.186 | −11.673 | 7.601 | 1.00 | 0.00 | N |
| ATOM | 307 | CA | GLY | E | 38 | −0.986 | −11.294 | 8.387 | 1.00 | 0.00 | C |
| ATOM | 308 | C | GLY | E | 38 | −1.293 | −9.816 | 8.541 | 1.00 | 0.00 | C |
| ATOM | 309 | O | GLY | E | 38 | −1.508 | −9.350 | 9.663 | 1.00 | 0.00 | O |
| ATOM | 310 | HN | GLY | E | 38 | 0.930 | −12.143 | 8.086 | 1.00 | 0.00 | H |
| ATOM | 311 | HA2 | GLY | E | 38 | −1.847 | −11.747 | 7.917 | 1.00 | 0.00 | H |
| ATOM | 312 | HA3 | GLY | E | 38 | −0.823 | −11.687 | 9.380 | 1.00 | 0.00 | H |
| ATOM | 313 | N | VAL | E | 39 | −1.365 | −9.070 | 7.407 | 1.00 | 0.00 | N |
| ATOM | 314 | CA | VAL | E | 39 | −1.581 | −7.621 | 7.265 | 1.00 | 0.00 | C |
| ATOM | 315 | C | VAL | E | 39 | −2.828 | −7.129 | 8.043 | 1.00 | 0.00 | C |
| ATOM | 316 | O | VAL | E | 39 | −3.865 | −7.803 | 8.123 | 1.00 | 0.00 | O |
| ATOM | 317 | CB | VAL | E | 39 | −1.591 | −7.158 | 5.770 | 1.00 | 0.00 | C |
| ATOM | 318 | CG1 | VAL | E | 39 | −1.813 | −5.628 | 5.590 | 1.00 | 0.00 | C |
| ATOM | 319 | CG2 | VAL | E | 39 | −0.276 | −7.557 | 5.037 | 1.00 | 0.00 | C |
| ATOM | 320 | HN | VAL | E | 39 | −0.196 | −9.555 | 6.546 | 1.00 | 0.00 | H |
| ATOM | 321 | HA | VAL | E | 39 | −0.718 | −7.166 | 7.733 | 1.00 | 0.00 | H |
| ATOM | 322 | HB | VAL | E | 39 | −2.433 | −7.680 | 5.258 | 1.00 | 0.00 | H |
| ATOM | 323 | HG11 | VAL | E | 39 | −2.801 | −5.311 | 5.981 | 1.00 | 0.00 | H |
| ATOM | 324 | HG12 | VAL | E | 39 | −1.021 | −5.044 | 6.104 | 1.00 | 0.00 | H |
| ATOM | 325 | HG13 | VAL | E | 39 | −1.791 | −5.361 | 4.511 | 1.00 | 0.00 | H |
| ATOM | 326 | HG21 | VAL | E | 39 | −0.312 | −7.229 | 3.976 | 1.00 | 0.00 | H |
| ATOM | 327 | HG22 | VAL | E | 39 | 0.607 | −7.082 | 5.516 | 1.00 | 0.00 | H |
| ATOM | 328 | HG23 | VAL | E | 39 | −0.125 | −8.655 | 5.035 | 1.00 | 0.00 | H |
| ATOM | 329 | N | VAL | E | 40 | −2.722 | −5.916 | 8.658 | 1.00 | 0.00 | N |
| ATOM | 330 | CA | VAL | E | 40 | −3.784 | −5.198 | 9.369 | 1.00 | 0.00 | C |
| ATOM | 331 | C | VAL | E | 40 | −4.604 | −4.416 | 8.325 | 1.00 | 0.00 | C |
| ATOM | 332 | O | VAL | E | 40 | −4.082 | −3.559 | 7.606 | 1.00 | 0.00 | O |
| ATOM | 333 | CB | VAL | E | 40 | −3.280 | −4.281 | 10.522 | 1.00 | 0.00 | C |
| ATOM | 334 | CG1 | VAL | E | 40 | −4.454 | −3.576 | 11.262 | 1.00 | 0.00 | C |
| ATOM | 335 | CG2 | VAL | E | 40 | −2.414 | −5.071 | 11.545 | 1.00 | 0.00 | C |
| ATOM | 336 | HN | VAL | E | 40 | −1.866 | −5.410 | 8.597 | 1.00 | 0.00 | H |
| ATOM | 337 | HA | VAL | E | 40 | −4.422 | −5.947 | 9.817 | 1.00 | 0.00 | H |
| ATOM | 338 | HB | VAL | E | 40 | −2.635 | −3.486 | 10.078 | 1.00 | 0.00 | H |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 339 | HG11 | VAL | E | 40 | −4.060 | −2.931 | 12.077 | 1.00 | 0.00 | H |
| ATOM | 340 | HG12 | VAL | E | 40 | −5.031 | −2.922 | 10.575 | 1.00 | 0.00 | H |
| ATOM | 341 | HG13 | VAL | E | 40 | −5.148 | −4.316 | 11.712 | 1.00 | 0.00 | H |
| ATOM | 342 | HG21 | VAL | E | 40 | −2.043 | −4.389 | 12.340 | 1.00 | 0.00 | H |
| ATOM | 343 | HG22 | VAL | E | 40 | −3.003 | −5.878 | 12.029 | 1.00 | 0.00 | H |
| ATOM | 344 | HG23 | VAL | E | 40 | −1.527 | −5.526 | 11.056 | 1.00 | 0.00 | H |
| ATOM | 345 | N | ILE | E | 41 | −5.924 | −4.729 | 8.236 | 1.00 | 0.00 | N |
| ATOM | 346 | CA | ILE | E | 41 | −6.893 | −4.168 | 7.297 | 1.00 | 0.00 | C |
| ATOM | 347 | C | ILE | E | 41 | −7.889 | −3.330 | 8.114 | 1.00 | 0.00 | C |
| ATOM | 348 | O | ILE | E | 41 | −8.504 | −3.828 | 9.064 | 1.00 | 0.00 | O |
| ATOM | 349 | CB | ILE | E | 41 | −7.608 | −5.248 | 6.430 | 1.00 | 0.00 | C |
| ATOM | 350 | CG1 | ILE | E | 41 | −6.621 | −6.237 | 5.713 | 1.00 | 0.00 | C |
| ATOM | 351 | CG2 | ILE | E | 41 | −8.613 | −4.614 | 5.420 | 1.00 | 0.00 | C |
| ATOM | 352 | CD1 | ILE | E | 41 | −5.635 | −5.625 | 4.699 | 1.00 | 0.00 | C |
| ATOM | 353 | HN | ILE | E | 41 | −6.322 | −5.394 | 8.860 | 1.00 | 0.00 | H |
| ATOM | 354 | HA | ILE | E | 41 | −6.357 | −3.510 | 6.624 | 1.00 | 0.00 | H |
| ATOM | 355 | HB | ILE | E | 41 | −8.215 | −5.878 | 7.125 | 1.00 | 0.00 | H |
| ATOM | 356 | HG12 | ILE | E | 41 | −6.032 | −6.778 | 6.487 | 1.00 | 0.00 | H |
| ATOM | 357 | HG13 | ILE | E | 41 | −7.228 | −7.008 | 5.187 | 1.00 | 0.00 | H |
| ATOM | 358 | HG21 | ILE | E | 41 | −9.411 | −4.048 | 5.944 | 1.00 | 0.00 | H |
| ATOM | 359 | HG22 | ILE | E | 41 | −8.092 | −3.930 | 4.717 | 1.00 | 0.00 | H |
| ATOM | 360 | HG23 | ILE | E | 41 | −9.106 | −5.412 | 4.824 | 1.00 | 0.00 | H |
| ATOM | 361 | HD11 | ILE | E | 41 | −4.985 | −6.419 | 4.272 | 1.00 | 0.00 | H |
| ATOM | 362 | HD12 | ILE | E | 41 | −6.178 | −5.137 | 3.863 | 1.00 | 0.00 | H |
| ATOM | 363 | HD13 | ILE | E | 41 | −4.982 | −4.870 | 5.185 | 1.00 | 0.00 | H |
| ATOM | 364 | N | ALA | E | 42 | −8.047 | −2.029 | 7.739 | 1.00 | 0.00 | N |
| ATOM | 365 | CA | ALA | E | 42 | −8.966 | −1.076 | 8.334 | 1.00 | 0.00 | C |
| ATOM | 366 | C | ALA | E | 42 | −10.273 | −1.087 | 7.568 | 1.00 | 0.00 | C |
| ATOM | 367 | H | ALA | E | 42 | −10.303 | −0.735 | 6.660 | 0.00 | 0.00 | H |
| ATOM | 368 | O | ALA | E | 42 | −11.305 | −1.536 | 8.069 | 1.00 | 0.00 | O |
| ATOM | 369 | CB | ALA | E | 42 | −8.369 | 0.348 | 8.322 | 1.00 | 0.00 | C |
| ATOM | 370 | HN | ALA | E | 42 | −7.500 | −1.661 | 6.994 | 1.00 | 0.00 | H |
| ATOM | 371 | HA | ALA | E | 42 | −9.170 | −1.376 | 9.356 | 1.00 | 0.00 | H |
| ATOM | 372 | HB1 | ALA | E | 42 | −7.417 | 0.368 | 8.894 | 1.00 | 0.00 | H |
| ATOM | 373 | HB2 | ALA | E | 42 | −8.162 | 0.694 | 7.287 | 1.00 | 0.00 | H |
| ATOM | 374 | HB3 | ALA | E | 42 | −9.068 | 1.058 | 8.801 | 1.00 | 0.00 | H |
| TER | 375 | | ALA | | 42 | | | | | | |
| ATOM | 376 | N | LEU | E | 17 | −4.694 | −36.140 | 7.746 | 1.00 | 0.00 | N1+ |
| ATOM | 377 | H1 | LEU | E | 17 | −4.458 | −36.755 | 8.545 | 0.00 | 0.00 | H |
| ATOM | 378 | H2 | LEU | E | 17 | −5.616 | −36.439 | 7.314 | 0.00 | 0.00 | H |
| ATOM | 379 | CA | LEU | E | 17 | −4.787 | −34.713 | 8.198 | 1.00 | 0.00 | C |
| ATOM | 380 | C | LEU | E | 17 | −4.985 | −33.740 | 7.028 | 1.00 | 0.00 | C |
| ATOM | 381 | O | LEU | E | 17 | −4.889 | −34.132 | 5.863 | 1.00 | 0.00 | O |
| ATOM | 382 | CB | LEU | E | 17 | −3.484 | −34.357 | 8.997 | 1.00 | 0.00 | C |
| ATOM | 383 | CG | LEU | E | 17 | −3.348 | −34.891 | 10.461 | 1.00 | 0.00 | C |
| ATOM | 384 | CD1 | LEU | E | 17 | −3.351 | −36.431 | 10.610 | 1.00 | 0.00 | C |
| ATOM | 385 | CD2 | LEU | E | 17 | −2.088 | −34.291 | 11.132 | 1.00 | 0.00 | C |
| ATOM | 386 | H3 | LEU | E | 17 | −3.931 | −36.221 | 7.013 | 1.00 | 0.00 | H |
| ATOM | 387 | HA | LEU | E | 17 | −5.656 | −34.629 | 8.839 | 1.00 | 0.00 | H |
| ATOM | 388 | HB2 | LEU | E | 17 | −2.595 | −34.674 | 8.409 | 1.00 | 0.00 | H |
| ATOM | 389 | HB3 | LEU | E | 17 | −3.420 | −33.246 | 9.076 | 1.00 | 0.00 | H |
| ATOM | 390 | HG | LEU | E | 17 | −4.222 | −34.505 | 11.040 | 1.00 | 0.00 | H |
| ATOM | 391 | HD11 | LEU | E | 17 | −3.146 | −36.712 | 11.667 | 1.00 | 0.00 | H |
| ATOM | 392 | HD12 | LEU | E | 17 | −4.339 | −36.863 | 10.355 | 1.00 | 0.00 | H |
| ATOM | 393 | HD13 | LEU | E | 17 | −2.563 | −36.894 | 9.978 | 1.00 | 0.00 | H |
| ATOM | 394 | HD21 | LEU | E | 17 | −2.027 | −34.598 | 12.198 | 1.00 | 0.00 | H |
| ATOM | 395 | HD22 | LEU | E | 17 | −1.165 | −34.631 | 10.616 | 1.00 | 0.00 | H |
| ATOM | 396 | HD23 | LEU | E | 17 | −2.117 | −33.181 | 11.098 | 1.00 | 0.00 | H |
| ATOM | 397 | N | VAL | E | 18 | −5.250 | −32.431 | 7.323 | 1.00 | 0.00 | N |
| ATOM | 398 | CA | VAL | E | 18 | −5.140 | −31.322 | 6.362 | 1.00 | 0.00 | C |
| ATOM | 399 | C | VAL | E | 18 | −3.628 | −31.029 | 6.265 | 1.00 | 0.00 | C |
| ATOM | 400 | O | VAL | E | 18 | −3.062 | −30.266 | 7.053 | 1.00 | 0.00 | O |
| ATOM | 401 | CB | VAL | E | 18 | −6.000 | −30.072 | 6.707 | 1.00 | 0.00 | C |
| ATOM | 402 | CG1 | VAL | E | 18 | −5.834 | −28.954 | 5.638 | 1.00 | 0.00 | C |
| ATOM | 403 | CG2 | VAL | E | 18 | −7.504 | −30.437 | 6.863 | 1.00 | 0.00 | C |
| ATOM | 404 | HN | VAL | E | 18 | −5.442 | −32.132 | 8.254 | 1.00 | 0.00 | H |
| ATOM | 405 | HA | VAL | E | 18 | −5.481 | −31.687 | 5.400 | 1.00 | 0.00 | H |
| ATOM | 406 | HB | VAL | E | 18 | −5.647 | −29.662 | 7.682 | 1.00 | 0.00 | H |
| ATOM | 407 | HG11 | VAL | E | 18 | −6.453 | −28.072 | 5.907 | 1.00 | 0.00 | H |
| ATOM | 408 | HG12 | VAL | E | 18 | −4.779 | −28.612 | 5.576 | 1.00 | 0.00 | H |
| ATOM | 409 | HG13 | VAL | E | 18 | −6.153 | −29.308 | 4.635 | 1.00 | 0.00 | H |
| ATOM | 410 | HG21 | VAL | E | 18 | −8.091 | −29.534 | 7.135 | 1.00 | 0.00 | H |
| ATOM | 411 | HG22 | VAL | E | 18 | −7.914 | −30.840 | 5.913 | 1.00 | 0.00 | H |
| ATOM | 412 | HG23 | VAL | E | 18 | −7.656 | −31.191 | 7.662 | 1.00 | 0.00 | H |
| ATOM | 413 | N | PHE | E | 19 | −2.950 | −31.706 | 5.300 | 1.00 | 0.00 | N |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 414 | CA | PHE | E | 19 | −1.507 | −31.863 | 5.235 | 1.00 | 0.00 | C |
| ATOM | 415 | C | PHE | E | 19 | −0.908 | −31.009 | 4.116 | 1.00 | 0.00 | C |
| ATOM | 416 | O | PHE | E | 19 | −1.194 | −31.223 | 2.934 | 1.00 | 0.00 | O |
| ATOM | 417 | CB | PHE | E | 19 | −1.144 | −33.374 | 5.046 | 1.00 | 0.00 | C |
| ATOM | 418 | CG | PHE | E | 19 | 0.246 | −33.730 | 5.530 | 1.00 | 0.00 | C |
| ATOM | 419 | CD1 | PHE | E | 19 | 0.416 | −34.446 | 6.732 | 1.00 | 0.00 | C |
| ATOM | 420 | CD2 | PHE | E | 19 | 1.389 | −33.412 | 4.774 | 1.00 | 0.00 | C |
| ATOM | 421 | CE1 | PHE | E | 19 | 1.690 | −34.842 | 7.157 | 1.00 | 0.00 | C |
| ATOM | 422 | CE2 | PHE | E | 19 | 2.665 | −33.796 | 5.201 | 1.00 | 0.00 | C |
| ATOM | 423 | CZ | PHE | E | 19 | 2.815 | −34.517 | 6.390 | 1.00 | 0.00 | C |
| ATOM | 424 | HN | PHE | E | 19 | −3.455 | −32.243 | 4.629 | 1.00 | 0.00 | H |
| ATOM | 425 | HA | PHE | E | 19 | −1.099 | −31.539 | 6.186 | 1.00 | 0.00 | H |
| ATOM | 426 | HB2 | PHE | E | 19 | −1.860 | −33.993 | 5.630 | 1.00 | 0.00 | H |
| ATOM | 427 | HB3 | PHE | E | 19 | −1.236 | −33.677 | 3.981 | 1.00 | 0.00 | H |
| ATOM | 428 | HD1 | PHE | E | 19 | −0.444 | −34.712 | 7.329 | 1.00 | 0.00 | H |
| ATOM | 429 | HD2 | PHE | E | 19 | 1.294 | −32.865 | 3.849 | 1.00 | 0.00 | H |
| ATOM | 430 | HE1 | PHE | E | 19 | 1.808 | −35.396 | 8.078 | 1.00 | 0.00 | H |
| ATOM | 431 | HE2 | PHE | E | 19 | 3.534 | −33.535 | 4.610 | 1.00 | 0.00 | H |
| ATOM | 432 | HZ | PHE | E | 19 | 3.799 | −34.822 | 6.714 | 1.00 | 0.00 | H |
| ATOM | 433 | N | PHE | E | 20 | −0.039 | −30.030 | 4.488 | 1.00 | 0.00 | N |
| ATOM | 434 | CA | PHE | E | 20 | 0.810 | −29.269 | 3.578 | 1.00 | 0.00 | C |
| ATOM | 435 | C | PHE | E | 20 | 2.023 | −30.138 | 3.216 | 1.00 | 0.00 | C |
| ATOM | 436 | O | PHE | E | 20 | 2.811 | −30.498 | 4.094 | 1.00 | 0.00 | O |
| ATOM | 437 | CB | PHE | E | 20 | 1.247 | −27.904 | 4.195 | 1.00 | 0.00 | C |
| ATOM | 438 | CG | PHE | E | 20 | 1.908 | −27.003 | 3.173 | 1.00 | 0.00 | C |
| ATOM | 439 | CD1 | PHE | E | 20 | 1.129 | −26.172 | 2.345 | 1.00 | 0.00 | C |
| ATOM | 440 | CD2 | PHE | E | 20 | 3.310 | −26.966 | 3.043 | 1.00 | 0.00 | C |
| ATOM | 441 | CE1 | PHE | E | 20 | 1.735 | −25.324 | 1.410 | 1.00 | 0.00 | C |
| ATOM | 442 | CE2 | PHE | E | 20 | 3.916 | −26.119 | 2.106 | 1.00 | 0.00 | C |
| ATOM | 443 | CZ | PHE | E | 20 | 3.129 | −25.300 | 1.291 | 1.00 | 0.00 | C |
| ATOM | 444 | HN | PHE | E | 20 | 0.114 | −29.837 | 5.453 | 1.00 | 0.00 | H |
| ATOM | 445 | HA | PHE | E | 20 | 0.227 | −29.072 | 2.686 | 1.00 | 0.00 | H |
| ATOM | 446 | HB2 | PHE | E | 20 | 0.355 | −27.366 | 4.583 | 1.00 | 0.00 | H |
| ATOM | 447 | HB3 | PHE | E | 20 | 1.948 | −28.061 | 5.043 | 1.00 | 0.00 | H |
| ATOM | 448 | HD1 | PHE | E | 20 | 0.052 | −26.176 | 2.434 | 1.00 | 0.00 | H |
| ATOM | 449 | HD2 | PHE | E | 20 | 3.929 | −27.588 | 3.674 | 1.00 | 0.00 | H |
| ATOM | 450 | HE1 | PHE | E | 20 | 1.134 | −24.674 | 0.791 | 1.00 | 0.00 | H |
| ATOM | 451 | HE2 | PHE | E | 20 | 4.991 | −26.076 | 2.016 | 1.00 | 0.00 | H |
| ATOM | 452 | HZ | PHE | E | 20 | 3.601 | −24.631 | 0.585 | 1.00 | 0.00 | H |
| ATOM | 453 | N | ALA | E | 21 | 2.164 | −30.498 | 1.906 | 1.00 | 0.00 | N |
| ATOM | 454 | CA | ALA | E | 21 | 3.079 | −31.491 | 1.341 | 1.00 | 0.00 | C |
| ATOM | 455 | C | ALA | E | 21 | 4.497 | −31.514 | 1.936 | 1.00 | 0.00 | C |
| ATOM | 456 | O | ALA | E | 21 | 4.883 | −32.512 | 2.545 | 1.00 | 0.00 | O |
| ATOM | 457 | CB | ALA | E | 21 | 3.099 | −31.403 | −0.206 | 1.00 | 0.00 | C |
| ATOM | 458 | HN | ALA | E | 21 | 1.535 | −30.112 | 1.238 | 1.00 | 0.00 | H |
| ATOM | 459 | HA | ALA | E | 21 | 2.642 | −32.445 | 1.597 | 1.00 | 0.00 | H |
| ATOM | 460 | HB1 | ALA | E | 21 | 3.737 | −32.206 | −0.634 | 1.00 | 0.00 | H |
| ATOM | 461 | HB2 | ALA | E | 21 | 2.074 | −31.531 | −0.614 | 1.00 | 0.00 | H |
| ATOM | 462 | HB3 | ALA | E | 21 | 3.492 | −30.422 | −0.548 | 1.00 | 0.00 | H |
| ATOM | 463 | N | GLU | E | 22 | 5.263 | −30.400 | 1.771 | 1.00 | 0.00 | N |
| ATOM | 464 | CA | GLU | E | 22 | 6.475 | −30.018 | 2.485 | 1.00 | 0.00 | C |
| ATOM | 465 | C | GLU | E | 22 | 7.570 | −31.077 | 2.664 | 1.00 | 0.00 | C |
| ATOM | 466 | O | GLU | E | 22 | 7.654 | −31.678 | 3.738 | 1.00 | 0.00 | O |
| ATOM | 467 | CB | GLU | E | 22 | 7.018 | −28.644 | 1.978 | 1.00 | 0.00 | C |
| ATOM | 468 | CG | GLU | E | 22 | 7.380 | −28.531 | 0.468 | 1.00 | 0.00 | C |
| ATOM | 469 | CD | GLU | E | 22 | 7.607 | −27.099 | −0.012 | 1.00 | 0.00 | C |
| ATOM | 470 | OE1 | GLU | E | 22 | 7.580 | −26.133 | 0.797 | 1.00 | 0.00 | O1− |
| ATOM | 471 | OE2 | GLU | E | 22 | 7.823 | −26.935 | −1.242 | 1.00 | 0.00 | O |
| ATOM | 472 | HN | GLU | E | 22 | 4.917 | −29.682 | 1.178 | 1.00 | 0.00 | H |
| ATOM | 473 | HA | GLU | E | 22 | 6.131 | −29.822 | 3.493 | 1.00 | 0.00 | H |
| ATOM | 474 | HB2 | GLU | E | 22 | 6.226 | −27.892 | 2.186 | 1.00 | 0.00 | H |
| ATOM | 475 | HB3 | GLU | E | 22 | 7.902 | −28.351 | 2.586 | 1.00 | 0.00 | H |
| ATOM | 476 | HG2 | GLU | E | 22 | 8.310 | −29.089 | 0.241 | 1.00 | 0.00 | H |
| ATOM | 477 | HG3 | GLU | E | 22 | 6.560 | −28.945 | −0.157 | 1.00 | 0.00 | H |
| ATOM | 478 | N | ASP | E | 23 | 8.453 | −31.311 | 1.648 | 1.00 | 0.00 | N |
| ATOM | 479 | CA | ASP | E | 23 | 9.659 | −32.116 | 1.788 | 1.00 | 0.00 | C |
| ATOM | 480 | C | ASP | E | 23 | 10.698 | −31.346 | 2.631 | 1.00 | 0.00 | C |
| ATOM | 481 | O | ASP | E | 23 | 11.428 | −30.480 | 2.139 | 1.00 | 0.00 | O |
| ATOM | 482 | CB | ASP | E | 23 | 10.222 | −32.625 | 0.425 | 1.00 | 0.00 | C |
| ATOM | 483 | CG | ASP | E | 23 | 11.244 | −33.725 | 0.658 | 1.00 | 0.00 | C |
| ATOM | 484 | OD1 | ASP | E | 23 | 10.844 | −34.910 | 0.826 | 1.00 | 0.00 | O1− |
| ATOM | 485 | OD2 | ASP | E | 23 | 12.465 | −33.425 | 0.700 | 1.00 | 0.00 | O |
| ATOM | 486 | HN | ASP | E | 23 | 8.323 | −30.871 | 0.766 | 1.00 | 0.00 | H |
| ATOM | 487 | HA | ASP | E | 23 | 9.361 | −32.997 | 2.342 | 1.00 | 0.00 | H |
| ATOM | 488 | HB2 | ASP | E | 23 | 9.402 | −33.049 | −0.193 | 1.00 | 0.00 | H |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 489 | HB3 | ASP | E | 23 | 10.701 | −31.795 | −0.134 | 1.00 | 0.00 | H |
| ATOM | 490 | N | VAL | E | 24 | 10.738 | −31.665 | 3.954 | 1.00 | 0.00 | N |
| ATOM | 491 | CA | VAL | E | 24 | 11.639 | −31.109 | 4.967 | 1.00 | 0.00 | C |
| ATOM | 492 | C | VAL | E | 24 | 13.004 | −31.818 | 4.869 | 1.00 | 0.00 | C |
| ATOM | 493 | O | VAL | E | 24 | 13.086 | −33.050 | 4.779 | 1.00 | 0.00 | O |
| ATOM | 494 | CB | VAL | E | 24 | 11.046 | −31.152 | 6.410 | 1.00 | 0.00 | C |
| ATOM | 495 | CG1 | VAL | E | 24 | 12.015 | −30.571 | 7.480 | 1.00 | 0.00 | C |
| ATOM | 496 | CG2 | VAL | E | 24 | 9.688 | −30.395 | 6.481 | 1.00 | 0.00 | C |
| ATOM | 497 | HN | VAL | E | 24 | 10.056 | −32.300 | 4.304 | 1.00 | 0.00 | H |
| ATOM | 498 | HA | VAL | E | 24 | 11.782 | −30.069 | 4.705 | 1.00 | 0.00 | H |
| ATOM | 499 | HB | VAL | E | 24 | 10.854 | −32.218 | 6.675 | 1.00 | 0.00 | H |
| ATOM | 500 | HG11 | VAL | E | 24 | 11.547 | −30.618 | 8.486 | 1.00 | 0.00 | H |
| ATOM | 501 | HG12 | VAL | E | 24 | 12.962 | −31.149 | 7.527 | 1.00 | 0.00 | H |
| ATOM | 502 | HG13 | VAL | E | 24 | 12.257 | −29.509 | 7.262 | 1.00 | 0.00 | H |
| ATOM | 503 | HG21 | VAL | E | 24 | 9.816 | −29.327 | 6.201 | 1.00 | 0.00 | H |
| ATOM | 504 | HG22 | VAL | E | 24 | 8.938 | −30.846 | 5.799 | 1.00 | 0.00 | H |
| ATOM | 505 | HG23 | VAL | E | 24 | 9.272 | −30.439 | 7.510 | 1.00 | 0.00 | H |
| ATOM | 506 | N | GLY | E | 25 | 14.111 | −31.024 | 4.883 | 1.00 | 0.00 | N |
| ATOM | 507 | CA | GLY | E | 25 | 15.491 | −31.477 | 4.729 | 1.00 | 0.00 | C |
| ATOM | 508 | C | GLY | E | 25 | 16.017 | −31.220 | 3.332 | 1.00 | 0.00 | C |
| ATOM | 509 | O | GLY | E | 25 | 15.815 | −32.033 | 2.430 | 1.00 | 0.00 | O |
| ATOM | 510 | HN | GLY | E | 25 | 13.991 | −30.028 | 5.022 | 1.00 | 0.00 | H |
| ATOM | 511 | HA2 | GLY | E | 25 | 16.089 | −30.927 | 5.442 | 1.00 | 0.00 | H |
| ATOM | 512 | HA3 | GLY | E | 25 | 15.532 | −32.543 | 4.902 | 1.00 | 0.00 | H |
| ATOM | 513 | N | SER | E | 26 | 16.721 | −30.075 | 3.137 | 1.00 | 0.00 | N |
| ATOM | 514 | CA | SER | E | 26 | 17.327 | −29.655 | 1.868 | 1.00 | 0.00 | C |
| ATOM | 515 | C | SER | E | 26 | 18.644 | −30.379 | 1.577 | 1.00 | 0.00 | C |
| ATOM | 516 | O | SER | E | 26 | 19.451 | −30.630 | 2.474 | 1.00 | 0.00 | O |
| ATOM | 517 | CB | SER | E | 26 | 17.571 | −28.122 | 1.768 | 1.00 | 0.00 | C |
| ATOM | 518 | OG | SER | E | 26 | 16.328 | −27.439 | 1.628 | 1.00 | 0.00 | O |
| ATOM | 519 | HN | SER | E | 26 | 16.861 | −29.447 | 3.893 | 1.00 | 0.00 | H |
| ATOM | 520 | HA | SER | E | 26 | 16.623 | −29.917 | 1.088 | 1.00 | 0.00 | H |
| ATOM | 521 | HB2 | SER | E | 26 | 18.115 | −27.758 | 2.668 | 1.00 | 0.00 | H |
| ATOM | 522 | HB3 | SER | E | 26 | 18.180 | −27.881 | 0.869 | 1.00 | 0.00 | H |
| ATOM | 523 | HG | SER | E | 26 | 16.363 | −26.617 | 2.166 | 1.00 | 0.00 | H |
| ATOM | 524 | N | ASN | E | 27 | 18.871 | −30.711 | 0.274 | 1.00 | 0.00 | N |
| ATOM | 525 | CA | ASN | E | 27 | 20.009 | −31.447 | −0.279 | 1.00 | 0.00 | C |
| ATOM | 526 | C | ASN | E | 27 | 20.023 | −32.925 | 0.159 | 1.00 | 0.00 | C |
| ATOM | 527 | O | ASN | E | 27 | 20.841 | −33.343 | 0.984 | 1.00 | 0.00 | O |
| ATOM | 528 | CB | ASN | E | 27 | 21.374 | −30.702 | −0.060 | 1.00 | 0.00 | C |
| ATOM | 529 | CG | ASN | E | 27 | 22.516 | −31.239 | −0.934 | 1.00 | 0.00 | C |
| ATOM | 530 | OD1 | ASN | E | 27 | 22.885 | −30.637 | −1.944 | 1.00 | 0.00 | O |
| ATOM | 531 | ND2 | ASN | E | 27 | 23.095 | −32.400 | −0.539 | 1.00 | 0.00 | N |
| ATOM | 532 | HN | ASN | E | 27 | 18.204 | −30.396 | −0.412 | 1.00 | 0.00 | H |
| ATOM | 533 | HA | ASN | E | 27 | 19.842 | −31.445 | −1.348 | 1.00 | 0.00 | H |
| ATOM | 534 | HB2 | ASN | E | 27 | 21.243 | −29.629 | −0.315 | 1.00 | 0.00 | H |
| ATOM | 535 | HB3 | ASN | E | 27 | 21.668 | −30.760 | 1.008 | 1.00 | 0.00 | H |
| ATOM | 536 | HD21 | ASN | E | 27 | 22.675 | −32.914 | 0.214 | 1.00 | 0.00 | H |
| ATOM | 537 | HD22 | ASN | E | 27 | 23.857 | −32.750 | −1.077 | 1.00 | 0.00 | H |
| ATOM | 538 | N | LYS | E | 28 | 19.102 | −33.739 | −0.428 | 1.00 | 0.00 | N |
| ATOM | 539 | CA | LYS | E | 28 | 18.955 | −35.175 | −0.209 | 1.00 | 0.00 | C |
| ATOM | 540 | C | LYS | E | 28 | 19.695 | −35.968 | −1.294 | 1.00 | 0.00 | C |
| ATOM | 541 | O | LYS | E | 28 | 20.870 | −36.290 | −1.118 | 1.00 | 0.00 | O |
| ATOM | 542 | CB | LYS | E | 28 | 17.450 | −35.571 | −0.050 | 1.00 | 0.00 | C |
| ATOM | 543 | CG | LYS | E | 28 | 16.846 | −35.172 | 1.314 | 1.00 | 0.00 | C |
| ATOM | 544 | CD | LYS | E | 28 | 15.304 | −35.182 | 1.346 | 1.00 | 0.00 | C |
| ATOM | 545 | CE | LYS | E | 28 | 14.738 | −35.040 | 2.763 | 1.00 | 0.00 | C |
| ATOM | 546 | NZ | LYS | E | 28 | 13.306 | −34.710 | 2.730 | 1.00 | 0.00 | N1+ |
| ATOM | 547 | HN | LYS | E | 28 | 18.436 | −33.340 | −1.050 | 1.00 | 0.00 | H |
| ATOM | 548 | HA | LYS | E | 28 | 19.452 | −35.425 | 0.721 | 1.00 | 0.00 | H |
| ATOM | 549 | HB2 | LYS | E | 28 | 16.859 | −35.104 | −0.868 | 1.00 | 0.00 | H |
| ATOM | 550 | HB3 | LYS | E | 28 | 17.340 | −36.675 | −0.145 | 1.00 | 0.00 | H |
| ATOM | 551 | HG2 | LYS | E | 28 | 17.245 | −35.869 | 2.086 | 1.00 | 0.00 | H |
| ATOM | 552 | HG3 | LYS | E | 28 | 17.179 | −34.143 | 1.587 | 1.00 | 0.00 | H |
| ATOM | 553 | HD2 | LYS | E | 28 | 14.952 | −34.334 | 0.713 | 1.00 | 0.00 | H |
| ATOM | 554 | HD3 | LYS | E | 28 | 14.918 | −36.122 | 0.900 | 1.00 | 0.00 | H |
| ATOM | 555 | HE2 | LYS | E | 28 | 14.873 | −35.978 | 3.343 | 1.00 | 0.00 | H |
| ATOM | 556 | HE3 | LYS | E | 28 | 15.255 | −34.220 | 3.305 | 1.00 | 0.00 | H |
| ATOM | 557 | HZ1 | LYS | E | 28 | 12.695 | −35.544 | 2.688 | 1.00 | 0.00 | H |
| ATOM | 558 | HZ2 | LYS | E | 28 | 13.082 | −34.111 | 3.574 | 1.00 | 0.00 | H |
| ATOM | 559 | HZ3 | LYS | E | 28 | 13.075 | −34.124 | 1.855 | 1.00 | 0.00 | H |
| ATOM | 560 | N | GLY | E | 29 | 19.027 | −36.300 | −2.437 | 1.00 | 0.00 | N |
| ATOM | 561 | CA | GLY | E | 29 | 19.565 | −37.146 | −3.501 | 1.00 | 0.00 | C |
| ATOM | 562 | C | GLY | E | 29 | 18.480 | −38.474 | −3.542 | 1.00 | 0.00 | C |
| ATOM | 563 | O | GLY | E | 29 | 18.975 | −39.289 | −2.625 | 1.00 | 0.00 | O |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 564 | HN | GLY | E | 29 | 18.087 | −35.992 | −2.549 | 1.00 | 0.00 | H |
| ATOM | 565 | HA2 | GLY | E | 29 | 19.426 | −36.618 | −4.434 | 1.00 | 0.00 | H |
| ATOM | 566 | HA3 | GLY | E | 29 | 20.606 | −37.358 | −3.299 | 1.00 | 0.00 | H |
| ATOM | 567 | N | ALA | E | 30 | 18.044 | −38.713 | −4.623 | 1.00 | 0.00 | N |
| ATOM | 568 | CA | ALA | E | 30 | 17.195 | −39.887 | −4.853 | 1.00 | 0.00 | C |
| ATOM | 569 | C | ALA | E | 30 | 16.033 | −40.028 | −3.856 | 1.00 | 0.00 | C |
| ATOM | 570 | O | ALA | E | 30 | 14.870 | −40.004 | −4.264 | 1.00 | 0.00 | O |
| ATOM | 571 | CB | ALA | E | 30 | 17.996 | −41.209 | −5.016 | 1.00 | 0.00 | C |
| ATOM | 572 | HN | ALA | E | 30 | 18.002 | −38.032 | −5.347 | 1.00 | 0.00 | H |
| ATOM | 573 | HA | ALA | E | 30 | 16.728 | −39.708 | −5.812 | 1.00 | 0.00 | H |
| ATOM | 574 | HB1 | ALA | E | 30 | 18.515 | −41.475 | −4.071 | 1.00 | 0.00 | H |
| ATOM | 575 | HB2 | ALA | E | 30 | 17.320 | −42.045 | −5.296 | 1.00 | 0.00 | H |
| ATOM | 576 | HB3 | ALA | E | 30 | 18.761 | −41.098 | −5.813 | 1.00 | 0.00 | H |
| ATOM | 577 | N | ILE | E | 31 | 16.329 | −40.162 | −2.532 | 1.00 | 0.00 | N |
| ATOM | 578 | CA | ILE | E | 31 | 15.363 | −40.317 | −1.441 | 1.00 | 0.00 | C |
| ATOM | 579 | C | ILE | E | 31 | 14.825 | −38.916 | −1.073 | 1.00 | 0.00 | C |
| ATOM | 580 | O | ILE | E | 31 | 15.252 | −38.282 | −0.104 | 1.00 | 0.00 | O |
| ATOM | 581 | CB | ILE | E | 31 | 15.912 | −41.130 | −0.230 | 1.00 | 0.00 | C |
| ATOM | 582 | CG1 | ILE | E | 31 | 16.630 | −42.468 | −0.626 | 1.00 | 0.00 | C |
| ATOM | 583 | CG2 | ILE | E | 31 | 14.803 | −41.375 | 0.839 | 1.00 | 0.00 | C |
| ATOM | 584 | CD1 | ILE | E | 31 | 15.789 | −43.516 | −1.380 | 1.00 | 0.00 | C |
| ATOM | 585 | HN | ILE | E | 31 | 17.299 | −40.107 | −2.271 | 1.00 | 0.00 | H |
| ATOM | 586 | HA | ILE | E | 31 | 14.533 | −40.888 | −1.840 | 1.00 | 0.00 | H |
| ATOM | 587 | HB | ILE | E | 31 | 16.694 | −40.500 | 0.259 | 1.00 | 0.00 | H |
| ATOM | 588 | HG12 | ILE | E | 31 | 17.520 | −42.222 | −1.248 | 1.00 | 0.00 | H |
| ATOM | 589 | HG13 | ILE | E | 31 | 17.021 | −42.937 | 0.304 | 1.00 | 0.00 | H |
| ATOM | 590 | HG21 | ILE | E | 31 | 13.963 | −41.963 | 0.413 | 1.00 | 0.00 | H |
| ATOM | 591 | HG22 | ILE | E | 31 | 15.222 | −41.940 | 1.698 | 1.00 | 0.00 | H |
| ATOM | 592 | HG23 | ILE | E | 31 | 14.402 | −40.417 | 1.230 | 1.00 | 0.00 | H |
| ATOM | 593 | HD11 | ILE | E | 31 | 15.426 | −43.112 | −2.349 | 1.00 | 0.00 | H |
| ATOM | 594 | HD12 | ILE | E | 31 | 16.402 | −44.418 | −1.591 | 1.00 | 0.00 | H |
| ATOM | 595 | HD13 | ILE | E | 31 | 14.911 | −43.829 | −0.776 | 1.00 | 0.00 | H |
| ATOM | 596 | N | ILE | E | 32 | 13.866 | −38.413 | −1.894 | 1.00 | 0.00 | N |
| ATOM | 597 | CA | ILE | E | 32 | 13.175 | −37.125 | −1.794 | 1.00 | 0.00 | C |
| ATOM | 598 | C | ILE | E | 32 | 11.673 | −37.376 | −2.006 | 1.00 | 0.00 | C |
| ATOM | 599 | O | ILE | E | 32 | 11.276 | −38.069 | −2.950 | 1.00 | 0.00 | O |
| ATOM | 600 | CB | ILE | E | 32 | 13.798 | −36.046 | −2.733 | 1.00 | 0.00 | C |
| ATOM | 601 | CG1 | ILE | E | 32 | 13.397 | −34.568 | −2.405 | 1.00 | 0.00 | C |
| ATOM | 602 | CG2 | ILE | E | 32 | 13.703 | −36.399 | −4.249 | 1.00 | 0.00 | C |
| ATOM | 603 | CD1 | ILE | E | 32 | 12.021 | −34.061 | −2.875 | 1.00 | 0.00 | C |
| ATOM | 604 | HN | ILE | E | 32 | 13.600 | −38.950 | −2.697 | 1.00 | 0.00 | H |
| ATOM | 605 | HA | ILE | E | 32 | 13.305 | −36.780 | −0.776 | 1.00 | 0.00 | H |
| ATOM | 606 | HB | ILE | E | 32 | 14.892 | −36.078 | −2.497 | 1.00 | 0.00 | H |
| ATOM | 607 | HG12 | ILE | E | 32 | 13.485 | −34.405 | −1.308 | 1.00 | 0.00 | H |
| ATOM | 608 | HG13 | ILE | E | 32 | 14.163 | −33.909 | −2.876 | 1.00 | 0.00 | H |
| ATOM | 609 | HG21 | ILE | E | 32 | 14.149 | −37.394 | −4.455 | 1.00 | 0.00 | H |
| ATOM | 610 | HG22 | ILE | E | 32 | 12.644 | −36.415 | −4.583 | 1.00 | 0.00 | H |
| ATOM | 611 | HG23 | ILE | E | 32 | 14.247 | −35.643 | −4.853 | 1.00 | 0.00 | H |
| ATOM | 612 | HD11 | ILE | E | 32 | 11.908 | −34.171 | −3.974 | 1.00 | 0.00 | H |
| ATOM | 613 | HD12 | ILE | E | 32 | 11.192 | −34.601 | −2.378 | 1.00 | 0.00 | H |
| ATOM | 614 | HD13 | ILE | E | 32 | 11.913 | −32.983 | −2.623 | 1.00 | 0.00 | H |
| ATOM | 615 | N | GLY | E | 33 | 10.798 | −36.830 | −1.114 | 1.00 | 0.00 | N |
| ATOM | 616 | CA | GLY | E | 33 | 9.354 | −37.053 | −1.143 | 1.00 | 0.00 | C |
| ATOM | 617 | C | GLY | E | 33 | 8.801 | −37.518 | 0.184 | 1.00 | 0.00 | C |
| ATOM | 618 | O | GLY | E | 33 | 8.339 | −38.654 | 0.302 | 1.00 | 0.00 | O |
| ATOM | 619 | HN | GLY | E | 33 | 11.092 | −36.185 | −0.384 | 1.00 | 0.00 | H |
| ATOM | 620 | HA2 | GLY | E | 33 | 8.892 | −36.106 | −1.383 | 1.00 | 0.00 | H |
| ATOM | 621 | HA3 | GLY | E | 33 | 9.122 | −37.819 | −1.871 | 1.00 | 0.00 | H |
| ATOM | 622 | N | LEU | E | 34 | 8.823 | −36.622 | 1.207 | 1.00 | 0.00 | N |
| ATOM | 623 | CA | LEU | E | 34 | 8.145 | −36.731 | 2.499 | 1.00 | 0.00 | C |
| ATOM | 624 | C | LEU | E | 34 | 6.660 | −37.126 | 2.362 | 1.00 | 0.00 | C |
| ATOM | 625 | O | LEU | E | 34 | 5.918 | −36.579 | 1.541 | 1.00 | 0.00 | O |
| ATOM | 626 | CB | LEU | E | 34 | 8.344 | −34.415 | 3.327 | 1.00 | 0.00 | C |
| ATOM | 627 | CG | LEU | E | 34 | 7.941 | −35.418 | 4.838 | 1.00 | 0.00 | C |
| ATOM | 628 | CD1 | LEU | E | 34 | 8.825 | −34.451 | 5.664 | 1.00 | 0.00 | C |
| ATOM | 629 | CD2 | LEU | E | 34 | 6.448 | −35.085 | 5.072 | 1.00 | 0.00 | C |
| ATOM | 630 | HN | LEU | E | 34 | 9.416 | −35.803 | 1.082 | 1.00 | 0.00 | H |
| ATOM | 631 | HA | LEU | E | 34 | 8.659 | −37.529 | 3.017 | 1.00 | 0.00 | H |
| ATOM | 632 | HB2 | LEU | E | 34 | 9.434 | −35.189 | 3.272 | 1.00 | 0.00 | H |
| ATOM | 633 | HB3 | LEU | E | 34 | 7.822 | −34.577 | 2.813 | 1.00 | 0.00 | H |
| ATOM | 634 | HG | LEU | E | 34 | 8.133 | −36.439 | 5.243 | 1.00 | 0.00 | H |
| ATOM | 635 | HD11 | LEU | E | 34 | 8.647 | −33.401 | 5.351 | 1.00 | 0.00 | H |
| ATOM | 636 | HD12 | LEU | E | 34 | 8.585 | −34.534 | 6.746 | 1.00 | 0.00 | H |
| ATOM | 637 | HD13 | LEU | E | 34 | 9.901 | −34.688 | 5.530 | 1.00 | 0.00 | H |
| ATOM | 638 | HD21 | LEU | E | 34 | 5.779 | −35.811 | 4.569 | 1.00 | 0.00 | H |

-continued

| HEADER | | | | | PROTEIN FIBRIL | | | | | |
|---|---|---|---|---|---|---|---|---|---|---|
| REMARK | | 99 MOE v2007.09 | | | (Chemical Computing Group Inc) | | | Mon Jun 16 15:27:17 2008 | | |
| ATOM | 639 | HD22 | LEU | E | 34 | 6.209 | −35.100 | 6.156 | 1.00 | 0.00 | H |
| ATOM | 640 | HD23 | LEU | E | 34 | 6.211 | −34.073 | 4.675 | 1.00 | 0.00 | H |
| ATOM | 641 | N | MET | E | 35 | 6.217 | −38.123 | 3.183 | 1.00 | 0.00 | N |
| ATOM | 642 | CA | MET | E | 35 | 4.910 | −38.770 | 3.124 | 1.00 | 0.00 | C |
| ATOM | 643 | C | MET | E | 35 | 3.765 | −37.812 | 3.481 | 1.00 | 0.00 | C |
| ATOM | 644 | O | MET | E | 35 | 3.585 | −37.420 | 4.638 | 1.00 | 0.00 | O |
| ATOM | 645 | CB | MET | E | 35 | 4.833 | −40.051 | 4.011 | 1.00 | 0.00 | C |
| ATOM | 646 | CG | MET | E | 35 | 5.798 | −41.192 | 3.604 | 1.00 | 0.00 | C |
| ATOM | 647 | SD | MET | E | 35 | 5.642 | −42.707 | 4.610 | 1.00 | 0.00 | S |
| ATOM | 648 | CE | MET | E | 35 | 6.391 | −42.115 | 6.158 | 1.00 | 0.00 | C |
| ATOM | 649 | HN | MET | E | 35 | 6.827 | −38.499 | 3.871 | 1.00 | 0.00 | H |
| ATOM | 650 | HA | MET | E | 35 | 4.779 | −39.088 | 2.097 | 1.00 | 0.00 | H |
| ATOM | 651 | HB2 | MET | E | 35 | 5.024 | −39.765 | 5.068 | 1.00 | 0.00 | H |
| ATOM | 652 | HB3 | MET | E | 35 | 3.798 | −40.460 | 3.961 | 1.00 | 0.00 | H |
| ATOM | 653 | HG2 | MET | E | 35 | 5.593 | −41.452 | 2.541 | 1.00 | 0.00 | H |
| ATOM | 654 | HG3 | MET | E | 35 | 6.847 | −40.826 | 3.644 | 1.00 | 0.00 | H |
| ATOM | 655 | HE1 | MET | E | 35 | 7.428 | −41.752 | 5.989 | 1.00 | 0.00 | H |
| ATOM | 656 | HE2 | MET | E | 35 | 5.802 | −41.284 | 6.601 | 1.00 | 0.00 | H |
| ATOM | 657 | HE3 | MET | E | 35 | 6.437 | −42.932 | 6.909 | 1.00 | 0.00 | H |
| ATOM | 658 | N | VAL | E | 36 | 2.966 | −37.423 | 2.450 | 1.00 | 0.00 | N |
| ATOM | 659 | CA | VAL | E | 36 | 1.879 | −36.446 | 2.512 | 1.00 | 0.00 | C |
| ATOM | 660 | C | VAL | E | 36 | 0.637 | −37.124 | 3.120 | 1.00 | 0.00 | C |
| ATOM | 661 | O | VAL | E | 36 | −0.166 | −37.757 | 2.424 | 1.00 | 0.00 | O |
| ATOM | 662 | CB | VAL | E | 36 | 1.582 | −35.759 | 1.142 | 1.00 | 0.00 | C |
| ATOM | 663 | CG1 | VAL | E | 36 | 0.490 | −34.657 | 1.266 | 1.00 | 0.00 | C |
| ATOM | 664 | CG2 | VAL | E | 36 | 2.873 | −35.169 | 0.501 | 1.00 | 0.00 | C |
| ATOM | 665 | HN | VAL | E | 36 | 3.162 | −37.755 | 1.533 | 1.00 | 0.00 | H |
| ATOM | 666 | HA | VAL | E | 36 | 2.204 | −35.668 | 3.190 | 1.00 | 0.00 | H |
| ATOM | 667 | HB | VAL | E | 36 | 1.193 | −36.535 | 0.443 | 1.00 | 0.00 | H |
| ATOM | 668 | HG11 | VAL | E | 36 | −0.466 | −35.076 | 1.643 | 1.00 | 0.00 | H |
| ATOM | 669 | HG12 | VAL | E | 36 | 0.814 | −33.845 | 1.946 | 1.00 | 0.00 | H |
| ATOM | 670 | HG13 | VAL | E | 36 | 0.286 | −34.209 | 0.270 | 1.00 | 0.00 | H |
| ATOM | 671 | HG21 | VAL | E | 36 | 2.633 | −34.629 | −0.439 | 1.00 | 0.00 | H |
| ATOM | 672 | HG22 | VAL | E | 36 | 3.379 | −34.468 | 1.197 | 1.00 | 0.00 | H |
| ATOM | 673 | HG23 | VAL | E | 36 | 3.597 | −35.972 | 0.250 | 1.00 | 0.00 | H |
| ATOM | 674 | N | GLY | E | 37 | 0.443 | −36.995 | 4.463 | 1.00 | 0.00 | N |
| ATOM | 675 | CA | GLY | E | 37 | −0.684 | −37.578 | 5.203 | 1.00 | 0.00 | C |
| ATOM | 676 | C | GLY | E | 37 | −2.018 | −36.872 | 5.009 | 1.00 | 0.00 | C |
| ATOM | 677 | O | GLY | E | 37 | −2.704 | −36.541 | 5.983 | 1.00 | 0.00 | O |
| ATOM | 678 | HN | GLY | E | 37 | 1.129 | −36.501 | 5.000 | 1.00 | 0.00 | H |
| ATOM | 679 | HA2 | GLY | E | 37 | −0.802 | −38.602 | 4.875 | 1.00 | 0.00 | H |
| ATOM | 680 | HA3 | GLY | E | 37 | −0.432 | −37.512 | 6.252 | 1.00 | 0.00 | H |
| ATOM | 681 | N | GLY | E | 38 | −2.423 | −36.650 | 3.731 | 1.00 | 0.00 | N |
| ATOM | 682 | CA | GLY | E | 38 | −3.565 | −35.839 | 3.306 | 1.00 | 0.00 | C |
| ATOM | 683 | C | GLY | E | 38 | −4.940 | −36.477 | 3.363 | 1.00 | 0.00 | C |
| ATOM | 684 | O | GLY | E | 38 | −5.800 | −36.135 | 2.551 | 1.00 | 0.00 | O |
| ATOM | 685 | HN | GLY | E | 38 | −1.826 | −37.022 | 3.007 | 1.00 | 0.00 | H |
| ATOM | 686 | HA2 | GLY | E | 38 | −3.596 | −34.961 | 3.934 | 1.00 | 0.00 | H |
| ATOM | 687 | HA3 | GLY | E | 38 | −3.385 | −35.582 | 2.272 | 1.00 | 0.00 | H |
| ATOM | 688 | N | VAL | E | 39 | −5.190 | −37.396 | 4.335 | 1.00 | 0.00 | H |
| ATOM | 689 | CA | VAL | E | 39 | −6.488 | −38.012 | 4.618 | 1.00 | 0.00 | C |
| ATOM | 690 | C | VAL | E | 39 | −7.270 | −37.008 | 5.483 | 1.00 | 0.00 | C |
| ATOM | 691 | O | VAL | E | 39 | −7.001 | −36.850 | 6.682 | 1.00 | 0.00 | O |
| ATOM | 692 | CB | VAL | E | 39 | −6.406 | −39.429 | 5.261 | 1.00 | 0.00 | C |
| ATOM | 693 | CG1 | VAL | E | 39 | −7.819 | −40.027 | 5.516 | 1.00 | 0.00 | C |
| ATOM | 694 | CG2 | VAL | E | 39 | −5.568 | −40.403 | 4.385 | 1.00 | 0.00 | C |
| ATOM | 695 | HN | VAL | E | 39 | −4.429 | −37.670 | 4.917 | 1.00 | 0.00 | H |
| ATOM | 696 | HA | VAL | E | 39 | −7.000 | −38.124 | 3.670 | 1.00 | 0.00 | H |
| ATOM | 697 | HB | VAL | E | 39 | −5.895 | −39.340 | 6.247 | 1.00 | 0.00 | H |
| ATOM | 698 | HG11 | VAL | E | 39 | −8.406 | −39.393 | 6.213 | 1.00 | 0.00 | H |
| ATOM | 699 | HG12 | VAL | E | 39 | −8.388 | −40.127 | 4.566 | 1.00 | 0.00 | H |
| ATOM | 700 | HG13 | VAL | E | 39 | −7.733 | −41.035 | 5.974 | 1.00 | 0.00 | H |
| ATOM | 701 | HG21 | VAL | E | 39 | −5.510 | −41.402 | 4.867 | 1.00 | 0.00 | H |
| ATOM | 702 | HG22 | VAL | E | 39 | −6.027 | −40.529 | 3.382 | 1.00 | 0.00 | H |
| ATOM | 703 | HG23 | VAL | E | 39 | −4.530 | −40.034 | 4.251 | 1.00 | 0.00 | H |
| ATOM | 704 | N | VAL | E | 40 | −8.241 | −36.292 | 4.858 | 1.00 | 0.00 | N |
| ATOM | 705 | CA | VAL | E | 40 | −9.103 | −35.281 | 5.475 | 1.00 | 0.00 | C |
| ATOM | 706 | C | VAL | E | 40 | −10.416 | −35.968 | 5.885 | 1.00 | 0.00 | C |
| ATOM | 707 | O | VAL | E | 40 | −11.125 | −36.545 | 5.054 | 1.00 | 0.00 | O |
| ATOM | 708 | CB | VAL | E | 40 | −9.351 | −34.024 | 4.589 | 1.00 | 0.00 | C |
| ATOM | 709 | CG1 | VAL | E | 40 | −10.227 | −32.964 | 5.318 | 1.00 | 0.00 | C |
| ATOM | 710 | CG2 | VAL | E | 40 | −8.011 | −33.379 | 4.132 | 1.00 | 0.00 | C |
| ATOM | 711 | HN | VAL | E | 40 | −8.399 | −36.424 | 3.882 | 1.00 | 0.00 | H |
| ATOM | 712 | HA | VAL | E | 40 | −9.601 | −34.939 | 6.371 | 1.00 | 0.00 | H |
| ATOM | 713 | HB | VAL | E | 40 | −9.899 | −34.345 | 3.673 | 1.00 | 0.00 | H |

-continued

| HEADER | | | | | PROTEIN FIBRIL | | | | |
|---|---|---|---|---|---|---|---|---|---|
| REMARK | 99 MOE v2007.09 | | | | (Chemical Computing Group Inc) | | Mon Jun 16 15:27:17 2008 | | |
| ATOM | 714 | HG11 | VAL | E | 40 | −10.381 | −32.079 | 4.663 | 1.00 | 0.00 | H |
| ATOM | 715 | HG12 | VAL | E | 40 | −11.230 | −33.369 | 5.567 | 1.00 | 0.00 | H |
| ATOM | 716 | HG13 | VAL | E | 40 | −9.743 | −32.619 | 6.256 | 1.00 | 0.00 | H |
| ATOM | 717 | HG21 | VAL | E | 40 | −8.207 | −32.485 | 3.502 | 1.00 | 0.00 | H |
| ATOM | 718 | HG22 | VAL | E | 40 | −7.403 | −33.066 | 5.006 | 1.00 | 0.00 | H |
| ATOM | 719 | HG23 | VAL | E | 40 | −7.410 | −34.091 | 3.527 | 1.00 | 0.00 | H |
| ATOM | 720 | N | ILE | E | 41 | −10.751 | −35.908 | 7.203 | 1.00 | 0.00 | N |
| ATOM | 721 | CA | ILE | E | 41 | −11.966 | −36.466 | 7.800 | 1.00 | 0.00 | C |
| ATOM | 722 | C | ILE | E | 41 | −13.051 | −35.375 | 7.786 | 1.00 | 0.00 | C |
| ATOM | 723 | O | ILE | E | 41 | −12.874 | −34.293 | 8.357 | 1.00 | 0.00 | O |
| ATOM | 724 | CB | ILE | E | 41 | −11.750 | −37.067 | 9.220 | 1.00 | 0.00 | C |
| ATOM | 725 | CG1 | ILE | E | 41 | −10.532 | −38.054 | 9.311 | 1.00 | 0.00 | C |
| ATOM | 726 | CG2 | ILE | E | 41 | −13.054 | −37.722 | 9.772 | 1.00 | 0.00 | C |
| ATOM | 727 | CD1 | ILE | E | 41 | −10.581 | −39.309 | 8.417 | 1.00 | 0.00 | C |
| ATOM | 728 | HN | ILE | E | 41 | −10.162 | −35.435 | 7.8484 | 1.00 | 0.00 | H |
| ATOM | 729 | HA | ILE | E | 41 | −12.287 | −37.278 | 7.159 | 1.00 | 0.00 | H |
| ATOM | 730 | HB | ILE | E | 41 | −11.507 | −36.219 | 9.904 | 1.00 | 0.00 | H |
| ATOM | 731 | HG12 | ILE | E | 41 | −9.601 | −37.494 | 9.073 | 1.00 | 0.00 | H |
| ATOM | 732 | HG13 | ILE | E | 41 | −10.437 | −38.384 | 10.370 | 1.00 | 0.00 | H |
| ATOM | 733 | HG21 | ILE | E | 41 | −13.880 | −36.983 | 9.847 | 1.00 | 0.00 | H |
| ATOM | 734 | HG22 | ILE | E | 41 | −13.387 | −38.557 | 9.121 | 1.00 | 0.00 | H |
| ATOM | 735 | HG23 | ILE | E | 41 | −12.874 | −38.127 | 10.790 | 1.00 | 0.00 | H |
| ATOM | 736 | HD11 | ILE | E | 41 | −9.674 | −39.929 | 8.578 | 1.00 | 0.00 | H |
| ATOM | 737 | HD12 | ILE | E | 41 | −11.470 | −39.931 | 8.656 | 1.00 | 0.00 | H |
| ATOM | 738 | HD13 | ILE | E | 41 | −10.623 | −39.030 | 7.343 | 1.00 | 0.00 | H |
| ATOM | 739 | N | ALA | E | 42 | −14.200 | −35.665 | 7.117 | 1.00 | 0.00 | N |
| ATOM | 740 | CA | ALA | E | 42 | −15.376 | −34.818 | 7.035 | 1.00 | 0.00 | C |
| ATOM | 741 | C | ALA | E | 42 | −16.315 | −35.048 | 8.212 | 1.00 | 0.00 | C |
| ATOM | 742 | H | ALA | E | 42 | −16.713 | −34.272 | 8.647 | 0.00 | 0.00 | H |
| ATOM | 743 | O | ALA | E | 42 | −16.591 | −365.175 | 8.635 | 1.00 | 0.00 | O |
| ATOM | 744 | CB | ALA | E | 42 | −16.139 | −35.030 | 5.708 | 1.00 | 0.00 | C |
| ATOM | 745 | HN | ALA | E | 42 | −14.299 | −36.539 | 6.652 | 1.00 | 0.00 | H |
| ATOM | 746 | HA | ALA | E | 42 | −15.047 | −33.788 | 7.079 | 1.00 | 0.00 | H |
| ATOM | 747 | HB1 | ALA | E | 42 | −15.467 | −34.837 | 4.844 | 1.00 | 0.00 | H |
| ATOM | 748 | HB2 | ALA | E | 42 | −16.519 | −36.071 | 5.631 | 1.00 | 0.00 | H |
| ATOM | 749 | HB3 | ALA | E | 42 | −17.002 | −34.335 | 5.635 | 1.00 | 0.00 | H |
| TER | 750 | | ALA | | 42 | | | | | | |
| HETATM | 751 | C | * | | 53 | 9.744 | −25.831 | −3.543 | 0.00 | 0.00 | C |
| HETATM | 752 | H | * | | 53 | 9.721 | −26.606 | −2.793 | 0.00 | 0.00 | H |
| HETATM | 753 | C | * | | 53 | 10.953 | −25.485 | −4.191 | 0.00 | 0.00 | C |
| HETATM | 754 | C | * | | 53 | 12.240 | −26.077 | −3.862 | 0.00 | 0.00 | C |
| HETATM | 755 | H | * | | 53 | 13.086 | −25.808 | −4.512 | 0.00 | 0.00 | H |
| HETATM | 756 | C | * | | 53 | 12.487 | −26.907 | −2.815 | 0.00 | 0.00 | C |
| HETATM | 757 | H | * | | 53 | 11.648 | −27.207 | −2.169 | 0.00 | 0.00 | H |
| HETATM | 758 | C | * | | 53 | 13.793 | −27.472 | −2.513 | 0.00 | 0.00 | C |
| HETATM | 759 | C | * | | 53 | 10.919 | −24.274 | −5.175 | 0.00 | 0.00 | C |
| HETATM | 760 | H | * | | 53 | 11.823 | −24.190 | −5.694 | 0.00 | 0.00 | H |
| HETATM | 761 | C | * | | 53 | 9.724 | −23.811 | −5.478 | 0.00 | 0.00 | C |
| HETATM | 762 | O | * | | 53 | 9.702 | −22.789 | −6.448 | 0.00 | 0.00 | O |
| HETATM | 763 | H | * | | 53 | 10.584 | −22.706 | −6.812 | 0.00 | 0.00 | H |
| HETATM | 764 | C | * | | 53 | 8.547 | −24.143 | −4.805 | 0.00 | 0.00 | C |
| HETATM | 765 | H | * | | 53 | 7.632 | −23.614 | −5.026 | 0.00 | 0.00 | H |
| HETATM | 766 | C | * | | 53 | 8.557 | −25.151 | −3.839 | 0.00 | 0.00 | C |
| HETATM | 767 | O | * | | 53 | 7.372 | −25.430 | −3.127 | 0.00 | 0.00 | O |
| HETATM | 768 | H | * | | 53 | 7.560 | −26.138 | −2.437 | 0.00 | 0.00 | H |
| HETATM | 769 | C | * | | 53 | 15.002 | −26.920 | −3.000 | 0.00 | 0.00 | C |
| HETATM | 770 | H | * | | 53 | 15.006 | −26.007 | −3.577 | 0.00 | 0.00 | H |
| HETATM | 771 | C | * | | 53 | 10.227 | −27.545 | −2.744 | 0.00 | 0.00 | C |
| HETATM | 772 | H | * | | 53 | 17.133 | −27.111 | −3.140 | 0.00 | 0.00 | H |
| HETATM | 773 | C | * | | 53 | 16.268 | −28.721 | −1.992 | 0.00 | 0.00 | C |
| HETATM | 774 | O | * | | 53 | 17.505 | −29.359 | −1.788 | 0.00 | 0.00 | O |
| HETATM | 775 | H | * | | 53 | 18.150 | −28.868 | −2.305 | 0.00 | 0.00 | H |
| HETATM | 776 | C | * | | 53 | 15.089 | −29.261 | −1.468 | 0.00 | 0.00 | C |
| HETATM | 777 | H | * | | 53 | 15.123 | −30.165 | −0.878 | 0.00 | 0.00 | H |
| HETATM | 778 | C | * | | 53 | 13.859 | −28.637 | −1.721 | 0.00 | 0.00 | C |
| HETATM | 779 | H | * | | 53 | 12.960 | −29.082 | −1.315 | 0.00 | 0.00 | H |
| CONECT | 5 | 22 | | | | | | | | | |
| CONECT | 24 | 38 | | | | | | | | | |
| CONECT | 40 | 58 | | | | | | | | | |
| CONECT | 60 | 78 | | | | | | | | | |
| CONECT | 80 | 88 | | | | | | | | | |
| CONECT | 90 | 103 | | | | | | | | | |
| CONECT | 105 | 115 | | | | | | | | | |
| CONECT | 117 | 131 | | | | | | | | | |
| CONECT | 133 | 138 | | | | | | | | | |

-continued

| HEADER | | PROTEIN FIBRIL | | |
|---|---|---|---|---|
| REMARK | | 99 MOE v2007.09 | (Chemical Computing Group Inc) | Mon Jun 16 15:27:17 2008 |
| CONECT | 140 | 149 | | |
| CONECT | 151 | 163 | | |
| CONECT | 165 | 185 | | |
| CONECT | 187 | 192 | | |
| CONECT | 194 | 202 | | |
| CONECT | 204 | 221 | | |
| CONECT | 223 | 240 | | |
| CONECT | 242 | 247 | | |
| CONECT | 249 | 266 | | |
| CONECT | 268 | 283 | | |
| CONECT | 285 | 299 | | |
| CONECT | 301 | 306 | | |
| CONECT | 308 | 313 | | |
| CONECT | 315 | 329 | | |
| CONECT | 331 | 345 | | |
| CONECT | 347 | 364 | | |
| CONECT | 380 | 397 | | |
| CONECT | 399 | 413 | | |
| CONECT | 415 | 433 | | |
| CONECT | 435 | 453 | | |
| CONECT | 455 | 463 | | |
| CONECT | 465 | 478 | | |
| CONECT | 480 | 490 | | |
| CONECT | 492 | 506 | | |
| CONECT | 508 | 513 | | |
| CONECT | 515 | 524 | | |
| CONECT | 526 | 538 | | |
| CONECT | 540 | 560 | | |
| CONECT | 562 | 567 | | |
| CONECT | 569 | 577 | | |
| CONECT | 579 | 596 | | |
| CONECT | 598 | 615 | | |
| CONECT | 617 | 622 | | |
| CONECT | 624 | 641 | | |
| CONECT | 643 | 658 | | |
| CONECT | 660 | 674 | | |
| CONECT | 676 | 681 | | |
| CONECT | 683 | 688 | | |
| CONECT | 690 | 704 | | |
| CONECT | 706 | 720 | | |
| CONECT | 722 | 739 | | |
| CONECT | 751 | 752 | 753 | 766 |
| CONECT | 753 | 754 | 759 | |
| CONECT | 754 | 755 | 756 | |
| CONECT | 756 | 757 | 758 | |
| CONECT | 758 | 769 | 778 | |
| CONECT | 759 | 760 | 761 | |
| CONECT | 761 | 762 | 764 | |
| CONECT | 762 | 763 | | |
| CONECT | 764 | 765 | 766 | |
| CONECT | 766 | 767 | | |
| CONECT | 767 | 768 | | |
| CONECT | 769 | 770 | 771 | |
| CONECT | 771 | 772 | 773 | |
| CONECT | 773 | 774 | 776 | |
| CONECT | 774 | 775 | | |
| CONECT | 776 | 777 | 778 | |
| CONECT | 778 | 779 | | |
| END | | | | |

The present example is further evidence that pseudo-crystal structures described in the application have utility and may be used for virtual (in silico) screening in Alzheimer Disease, and, possibly, related disorders, e.g., Parkinson's Disease.

Example 5

Using the methods described in the applications, many compounds in the following Table were identified and predicted to have an anti-amyloid activity at Aβ and/or A-Syn amyloid proteins. Some of these compounds were synthesized and some of the compounds were obtained from commercial sources.

The anti-amyloid activity of these compounds was evaluated by ThT aggregation assays of Aβ 1-40 and alpha synuclein, as set forth below. The column "A-Syn" below is a functional ThT aggregation assay of alpha synuclein.

| Structure | Aβ - ThT (IC$_{50}$/μM) | A-syn |
|---|---|---|
| 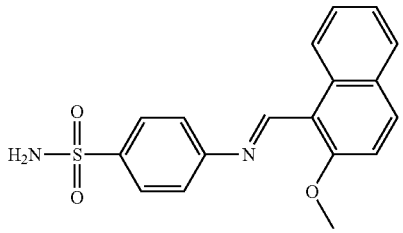 [SMILES: COc1ccc2ccccc2c1/C=N/c1ccc(S(N)(=O)=O)cc1] | >20 | |
| 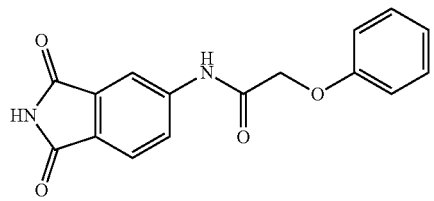 [SMILES: O=C(COc1ccccc1)Nc1ccc2c(c1)C(=O)NC2=O] | >20 | |
| 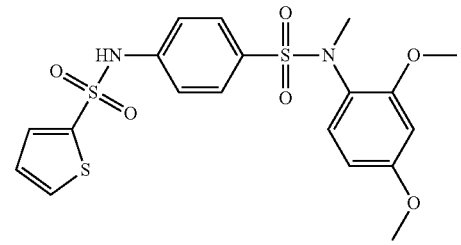 [SMILES: COc1ccc(N(C)S(=O)(=O)c2ccc(NS(=O)(=O)c3cccs3)cc2)c(OC)c1] | >20 | |
| 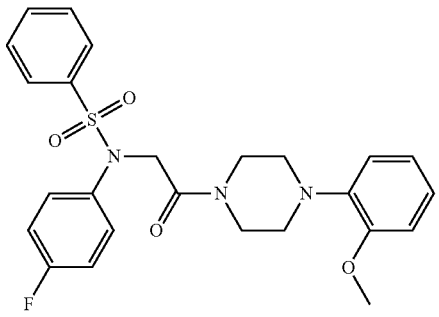 [SMILES: COc1ccccc1N1CCN(C(=O)CN(c2ccc(F)cc2)S(=O)(=O)c2ccccc2)CC1] | >20 | |
| 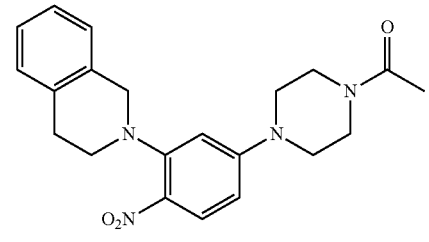 [SMILES: CC(=O)N1CCN(c2ccc([N+](=O)[O-])c(N3CCc4ccccc4C3)c2)CC1] | 4.03 | |
| 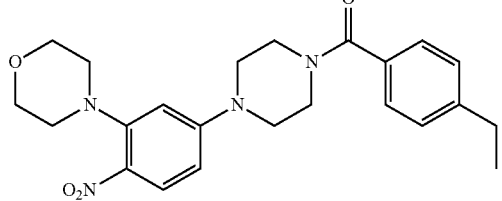 | 2.7 | |

-continued

| Structure | Aβ - ThT (IC$_{50}$/μM) | A-syn |
|---|---|---|
| [structure: 3-methyl-5-oxo-4,5-dihydro-1H-pyrazol-4-yl acetohydrazide linked via CH=N to 3-(benzyloxy)phenyl] | >20 | |
| [structure: benzoylglycine hydrazide linked via CH=N to 3-phenyl-1H-pyrazol-4-yl] | >20 | |
| [structure: 4-(pyrimidin-2-yl)piperazin-1-yl carbonyl-phenyl-C≡C-C(CH$_3$)$_2$-OH] | >20 | |
| [structure: furan-2-ylmethylamino-nitrophenyl-piperazinyl-(2-fluorobenzoyl)] | 2.1 | |
| [structure: 4-chlorobenzylamino-nitrophenyl-piperazinyl-(4H-1,2,4-triazol-3-yl)carbonyl] | 1.4 | |
| [structure: isoxazol-5-ylmethylamino-nitrophenyl-piperazinyl-(3,4-dimethoxybenzoyl)] | >20 | |
| [structure: 1-phenyl-1H-tetrazol-5-ylthio-nitrophenyl-piperazinyl-ethanol] | — | |

| Structure | Aβ - ThT (IC$_{50}$/μM) | A-syn |
|---|---|---|
| 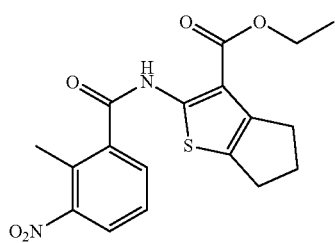 [SMILES: CCOC(=O)c1c(NC(=O)c2cccc([N+](=O)[O-])c2C)sc2c1CCC2] | >20 | |
| 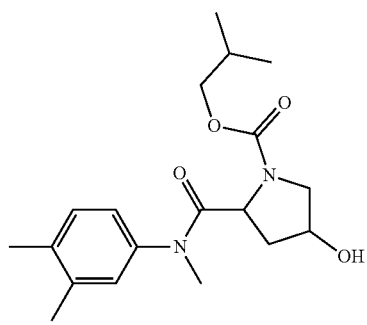 [SMILES: Cc1ccc(N(C)C(=O)C2CC(O)CN2C(=O)OCC(C)C)cc1C] | >20 | |
| 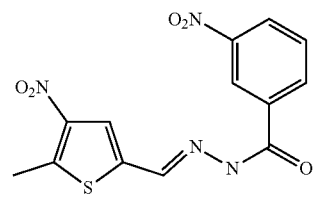 [SMILES: Cc1sc(/C=N/NC(=O)c2cccc([N+](=O)[O-])c2)cc1[N+](=O)[O-]] | >20 | |
| 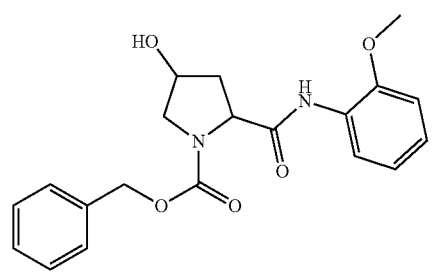 [SMILES: COc1ccccc1NC(=O)C1CC(O)CN1C(=O)OCc1ccccc1] | >20 | |
| 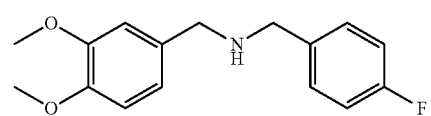 [SMILES: COc1ccc(CNCc2ccc(F)cc2)cc1OC] | >100 | |
| 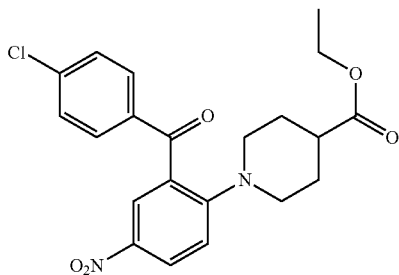 [SMILES: CCOC(=O)C1CCN(c2ccc([N+](=O)[O-])cc2C(=O)c2ccc(Cl)cc2)CC1] | >20 | |

-continued

| Structure | Aβ - ThT (IC$_{50}$/μM) | A-syn |
|---|---|---|
| 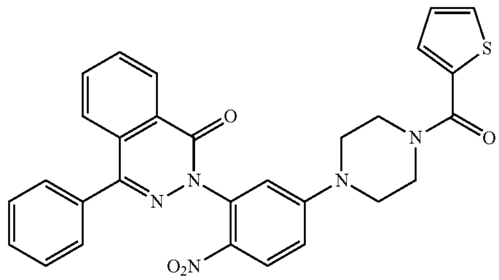 [SMILES: O=C(c1cccs1)N1CCN(c2ccc([N+](=O)[O-])c(-n3nc(-c4ccccc4)c4ccccc4c3=O)c2)CC1] | >20 |  |
|  | >100 |  |
|  | >100 |  |
| 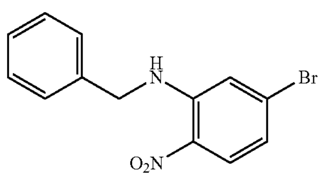 [SMILES: O=[N+]([O-])c1ccc(Br)cc1NCc1ccccc1] | 20-50 |  |
| 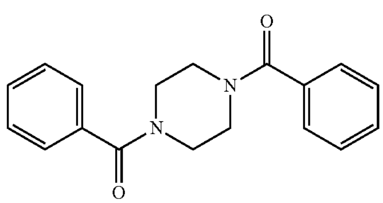 [SMILES: O=C(c1ccccc1)N1CCN(C(=O)c2ccccc2)CC1] | — |  |
| 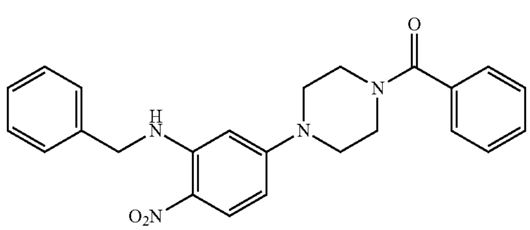 [SMILES: O=C(c1ccccc1)N1CCN(c2ccc([N+](=O)[O-])c(NCc3ccccc3)c2)CC1] | 10-20 | 51 |
| 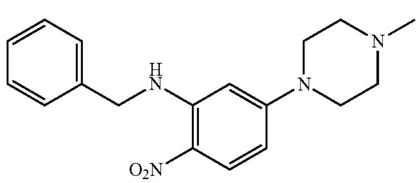 [SMILES: CN1CCN(c2ccc([N+](=O)[O-])c(NCc3ccccc3)c2)CC1] | 9.0 | 11.61 |

-continued

| Structure | Aβ - ThT (IC$_{50}$/μM) | A-syn |
|---|---|---|
| 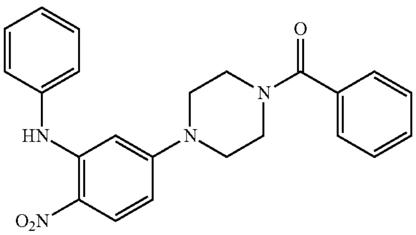 [SMILES: O=C(c1ccccc1)N1CCN(c2ccc([N+](=O)[O-])c(Nc3ccccc3)c2)CC1] | 0.85 | 6.34 |
| 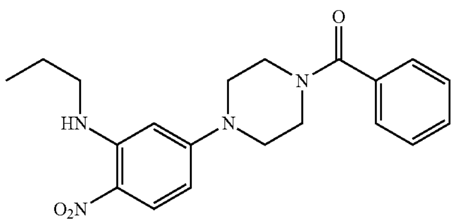 [SMILES: CCCNc1cc(N2CCN(C(=O)c3ccccc3)CC2)ccc1[N+](=O)[O-]] | 2.5 | 142 |
| 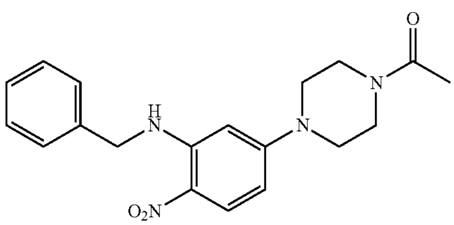 [SMILES: CC(=O)N1CCN(c2ccc([N+](=O)[O-])c(NCc3ccccc3)c2)CC1] | 25.8 | |
| | >50 | |
| | >50 | |
| | >50 | |
| | >50 | |

-continued

| Structure | Aβ - ThT (IC$_{50}$/μM) | A-syn |
|---|---|---|
| 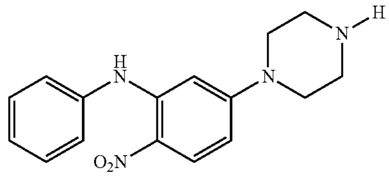 [SMILES: O=[N+]([O-])c1ccc(N2CCNCC2)cc1Nc1ccccc1] | 8.82 | |
| | >50 | |
| 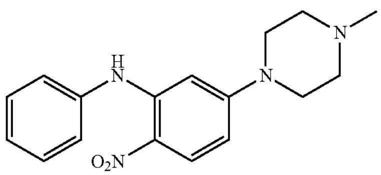 [SMILES: CN1CCN(c2ccc([N+](=O)[O-])c(Nc3ccccc3)c2)CC1] | 23.2 | |
| | >50 | |
| | >50 | |
| 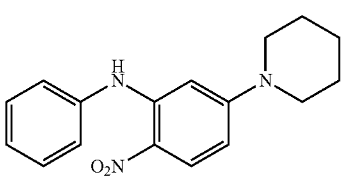 [SMILES: O=[N+]([O-])c1ccc(N2CCCCC2)cc1Nc1ccccc1] | INACTIVE | |
| 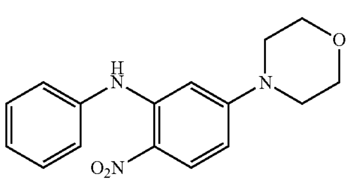 [SMILES: O=[N+]([O-])c1ccc(N2CCOCC2)cc1Nc1ccccc1] | 23 | |
| | >50 | |

-continued

| Structure | Aβ - ThT (IC$_{50}$/μM) | A-syn |
|---|---|---|
| [structure: phenyl-NH-(nitrophenyl)-piperazine-C(=O)-N(CH$_3$)$_2$] | 8.4 | |
| [structure: phenyl-NH-(nitrophenyl)-N(CH$_3$)$_2$] | 39 | |
| [structure: PhC(=O)NH-(nitrophenyl)-piperazine-C(=O)Ph] | 177.5 | |
| [structure: Ph-N(CH$_3$)-(nitrophenyl)-piperazine-C(=O)Ph] | 9.64 | 5 |
| [structure: CH$_3$C(=O)NH-(nitrophenyl)-piperazine-C(=O)Ph] | 44 | |
| [structure: (CH$_3$)$_2$N-(nitrophenyl)-piperazine-C(=O)Ph] | 25 | 4 |

-continued

| Structure | Aβ - ThT (IC$_{50}$/μM) | A-syn |
|---|---|---|
| 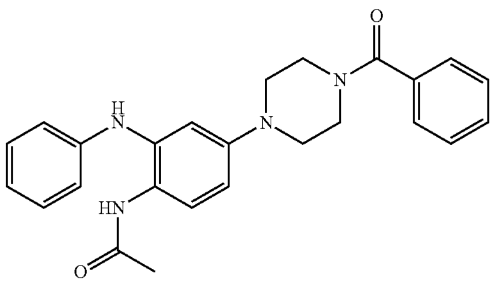 [SMILES: CC(=O)Nc1ccc(N2CCN(C(=O)c3ccccc3)CC2)cc1Nc1ccccc1] | 100 | |
| 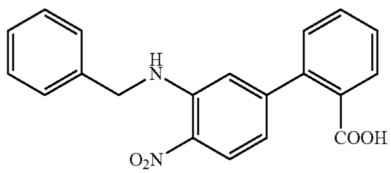 [SMILES: O=C(O)c1ccccc1-c1ccc([N+](=O)[O-])c(NCc2ccccc2)c1] | 41.9 | |
| 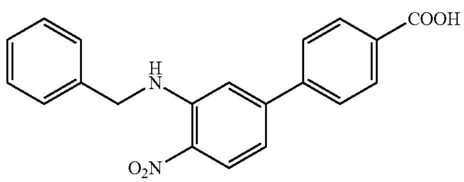 [SMILES: O=C(O)c1ccc(-c2ccc([N+](=O)[O-])c(NCc3ccccc3)c2)cc1] | 184 | |
| 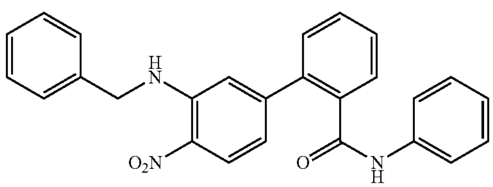 [SMILES: O=C(Nc1ccccc1)c1ccccc1-c1ccc([N+](=O)[O-])c(NCc2ccccc2)c1] | 152 | |
| 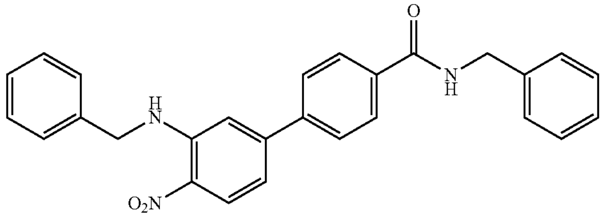 [SMILES: O=C(NCc1ccccc1)c1ccc(-c2ccc([N+](=O)[O-])c(NCc3ccccc3)c2)cc1] | 42 | |
| 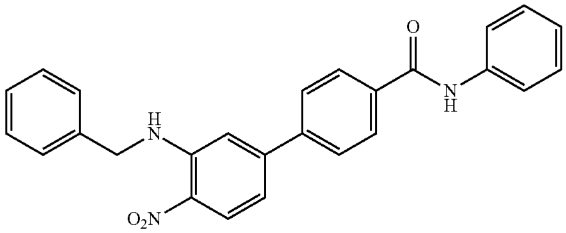 [SMILES: O=C(Nc1ccccc1)c1ccc(-c2ccc([N+](=O)[O-])c(NCc3ccccc3)c2)cc1] | 217 | |

-continued

| Structure | Aβ - ThT (IC$_{50}$/μM) | A-syn |
|---|---|---|
| (structure: 2-(4-benzoylpiperazin-1-yl)-5-nitrophenyl benzamide) | 1035 | |
| (structure: biphenyl with benzylamino, nitro, and N-benzylcarboxamide substituents) | 631 | |
| (structure: 2-(benzylamino)-4-(4-benzoylpiperazin-1-yl)benzoic acid) | 189 | |
| (structure: 2-(benzylamino)-4-(4-benzoylpiperazin-1-yl)-N-methylbenzamide) | ND | |
| (structure: 2-(benzylamino)-4-(4-benzoylpiperazin-1-yl)-N,N-dimethylbenzamide) | 84 | |

-continued

| Structure | Aβ - ThT (IC$_{50}$/μM) | A-syn |
|---|---|---|
| (3-nitrophenyl)-piperazine-benzoyl structure | 196 | |
| benzylamino-benzamide-piperazine-benzoyl structure | 265 | |
| benzylamino-N-ethylbenzamide-piperazine-benzoyl structure | 66.2 | |
| N-benzyl-2-nitroaniline structure | 63 | |
| benzylamino-methyl benzoate-piperazine-benzoyl structure | 174 | |

-continued

| Structure | Aβ - ThT (IC$_{50}$/μM) | A-syn |
|---|---|---|
| (structure) | 18 | |
| (structure) | 105 | |
| (structure) | 1.47 | 8 |
| (structure) | 5734 | |
| (structure) | 14935 | |
| (structure) | 23 | |
| (structure) | 544 | |

-continued

| Structure | Aβ - ThT (IC$_{50}$/μM) | A-syn |
|---|---|---|
| (benzyl-NH-, 4-O$_2$N, phenyl-piperidine-C(O)NH-benzyl) | 975 | |
| (phenyl-NH-, 4-O$_2$N-phenyl, piperazine-C(O)-phenyl) | 92 | |
| (phenyl-NH-, 4-H$_2$N-phenyl, piperazine-C(O)-phenyl) | 1.9 | |
| (benzyl-NH-, 4-(Et$_2$N-C(O))-phenyl, piperazine-C(O)-phenyl) | 361 | |
| (benzyl-NH-, 4-O$_2$N-phenyl, piperidine-3-COOH) | 21.7 | |
| (phenyl-NH-, 4-O$_2$N-phenyl, 3-COOH-phenyl) | 9.23 | 10 |

-continued

| Structure | Aβ - ThT (IC$_{50}$/μM) | A-syn |
|---|---|---|
| [structure: 2-(dimethylamino)-4-nitrophenyl piperazine benzamide] | 27 | 15 |
| [structure: 3-nitrophenyl piperazine benzamide] | 360 | |
| [structure: 3-aminophenyl piperazine benzamide] | 428 | |
| [structure: 3-(phenylamino)phenyl piperazine benzamide] | 539 | |
| [structure: biphenyl with NHPh, NH$_2$ and COOH] | 26.6 | 45 |
| [structure: N-benzyl-N-phenyl diamino phenyl piperazine benzamide] | 106.6 | |
| [structure: N-methyl-N-phenyl, N,N-dimethyl diamino phenyl piperazine benzamide] | 148 | |

-continued

| Structure | Aβ - ThT (IC$_{50}$/μM) | A-syn |
|---|---|---|
| [structure] | 3.5 | ~7 |
| [structure] | 15.5 | |
| [structure] | 7.8 | |
| [structure] | 2.29 | |
| [structure] | 90 | |

| Structure | Aβ - ThT (IC$_{50}$/μM) | A-syn |
|---|---|---|
| 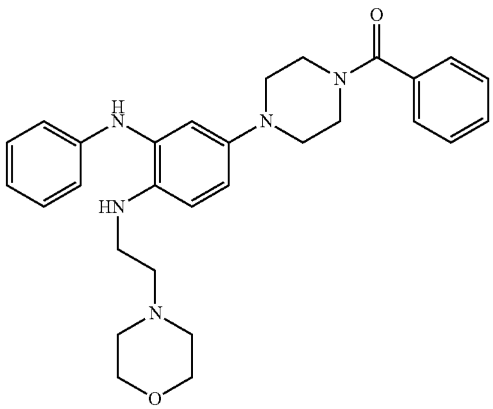 [SMILES: O=C(c1ccccc1)N1CCN(c2ccc(NCCN3CCOCC3)c(Nc3ccccc3)c2)CC1] | 54.4 | |
| 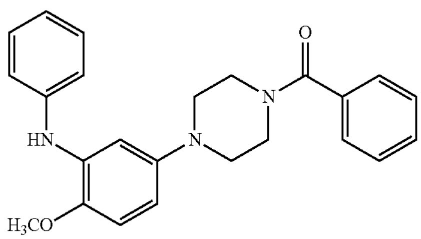 [SMILES: COc1ccc(N2CCN(C(=O)c3ccccc3)CC2)cc1Nc1ccccc1] | 238.4 | |

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A method of using a computer molecular modeling program on a computer system for identifying compounds that modulate amyloid aggregation comprising the steps of:
constructing a non-crystallographic model of amyloid protein aggregation comprising a three-dimensional model of a monomeric amyloid peptide; and a three-dimensional model of an amyloid protein consisting of one or more amyloid peptides, said amyloid protein model to be positioned with respect to said amyloid peptide model such that it forms a pocket in conjunction with said amyloid peptide model such that a candidate compound may be inserted into said pocket thereby modulating amyloid aggregation, wherein
said amyloid peptide model and said amyloid protein model are both composed of beta-amyloid protein or an amyloid-forming fragment thereof,
said amyloid peptide model is positioned with respect to said amyloid protein model substantially in the orientation shown in FIG. 2,
said amyloid peptide model is substantially SEQ ID: 1;
said amyloid protein model is substantially SEQ ID: 2; and
said amyloid peptide model is positioned with respect to said amyloid protein model such that:
the amino acid Val at position 8 of SEQ ID: 1 interacts with the amino acid Glu at position 6 of SEQ ID: 2;
the amino acid Gly at position 9 of SEQ ID: 1 interacts with the amino acid Glu at position 6 of SEQ ID: 2;
the amino acid Ser at position 10 of SEQ ID: 1 interacts with the amino acid Gly at position 9 of SEQ ID: 2;
the amino acid Ser at position 10 of SEQ ID: 1 interacts with the amino acid Ser at position 10 of SEQ ID:2; and
the amino acid Lys at position 12 of SEQ ID: 1 interacts with the amino acid Glu at position 6 of SEQ ID: 2;
selecting a list of candidate compounds;
constructing said candidate compounds in a computer molecular modeling program;
docking each candidate compound into said pocket and scoring each candidate compound to reflect its degree of complementarity with respect to said pocket in the computer molecular modeling program; and
identifying compounds that modulate amyloid aggregation or better modulate amyloid aggregation by reference to a score cutoff that reflects a degree of complementarity with respect to said pocket and substantially distinguishes active compounds from inactive compounds, or more active compounds from less active compounds, respectively, wherein the active compounds are output to be further evaluated experimentally as amyloid aggregation inhibitors.

2. The method of claim 1, further comprising determining the amyloid aggregation activity of the identified compounds in an in vitro assay.

3. The method of claim 2, wherein the in vitro assay is ThT assay.

4. The method of claim 1, wherein the candidate compounds are selected from
(a) a group consisting of a compound of Formula Ia, a compound of Formula Ib, a compound of Formula Ic, and pharmaceutically acceptable salts thereof:

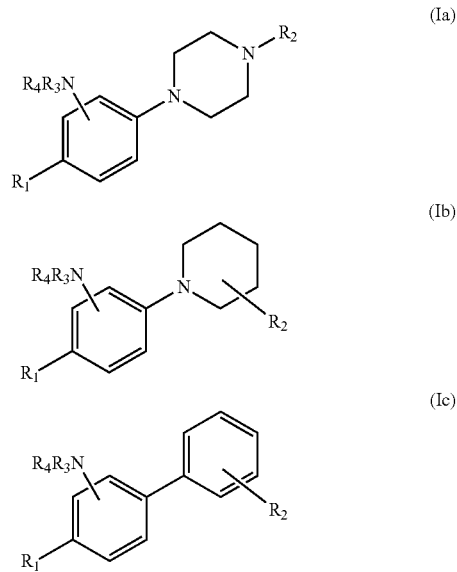

wherein
$R_1$ is selected from the group consisting of H, nitro, carboxylic acid, alkylcarboxylic acid, acetamide connected in either direction, N-(2-ethanol)amine, N-(2-morpholinethyl)amine, amine optionally substituted with one or more alkyl groups, amide optionally substituted with one or more alkyl groups, and alkoxy;
$R_2$ is selected from the group consisting of H, carboxylic acid, alkyl, alkanoyl, alkanesulfonyl, benzenesulfonyl, phenonyl optionally substituted with any one or more of alkoxy, halogen, or alkyl groups, benzyl optionally substituted with any one or more of alkoxy, halogen, or alkyl groups, and amide optionally substituted with any one or more of alkyl or aryl groups;
$R_3$ is selected from the group consisting of H, alkyl, furanylalkyl, thiophenealkyl, alkanoyl, phenyl optionally substituted with any one or more halogen, alkyl, or alkoxy groups, benzyl optionally substituted with any one or more halogen, alkyl, or alkoxy groups, and phenonyl optionally substituted with any one or more halogen, alkyl, or alkoxy groups; and
$R_4$ is selected from the group consisting of H, alkyl, or phenyl optionally substituted with any one or more halogen, alkyl, or alkoxy groups; or
b) a group consisting of a compound of Formula II, a compound of Formula III, and pharmaceutically acceptable salts thereof:

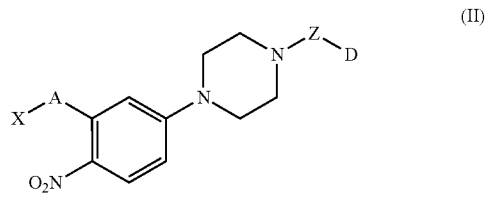

wherein
X is selected from the group consisting of hydrogen, methyl, amine, methoxy, phenyl optionally substituted with up to a total of three methyl and/or methoxy and/or halogen groups, cyclopentane, morpholine, piperidine, N-methylpiperidine, N-ethylpiperidine, (N,N-diethyl) formamide, pyridine, pyrazine, pyrrole, pyrrolidine, furan, thiophene, tetrahydrofuran, pyran, tetrahydroisoquinoline, isoquinoline, quinoline, N-phenylpiperazine optionally substituted with up to a total of three methoxy and/or halogen groups, or N-benzylpiperazine;

A is an optional spacer group, attachable in either direction, selected from the group consisting of —NH—, —NHCH$_2$—, —NHCH$_2$CH$_2$—, —NHCH$_2$CH$_2$O—, and —NHCH$_2$(CH$_3$);

D is selected from the group consisting of methyl, isopropyl, tert-butyl, dimethylamine, morpholine, alcohol, phenyl optionally substituted with up to a total of three methyl and/or ethyl and/or methoxy and/or halogen and/or acetamide and/or ethoxy and/or cyano groups, pyridine, pyrazine, pyrrole, pyrrolidine, furan, thiophene, tetrahydrofuran, and pyran; and Z is an optional spacer group, selected from the group consisting of —CH$_2$—, —SO$_2$—, —SO$_2$CH$_2$—, —CH$_2$C(=O)—, —CH$_2$CH$_2$—, —C(=O)—, and —C(=S)NHC(=O)—; or c) a group consisting of a compound of Formula III, and pharmaceutically acceptable salts thereof:

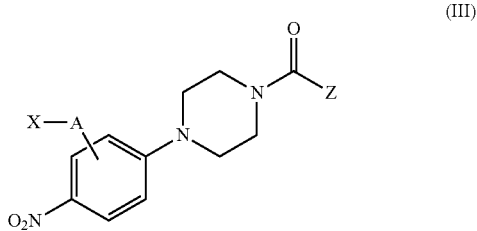

(III)

wherein

X is selected from the group consisting of methyl, methylamine, halogen, and phenyl optionally substituted with up to a total of three methyl and/or methoxy and/or halogen groups;

A is an optional spacer group, attachable in either direction, selected from the group consisting of —NH—, —N(CH$_3$)H—, —O—, —OCH$_3$—, —C(=O)NH—, and —NHCH$_2$—; and Z is selected from the group consisting of phenyl optionally substituted with up to a total of three methyl and/or ethyl and/or methoxy and/or halogen and/or acetamide and/or ethoxy and/or cyano groups; excepting those compounds that include X as phenyl and A as —NHCH$_2$—, the nitrogen in said A being connected to the nitro-containing phenyl ring in said formula and the carbon in said A being connected to said X in said formula.

5. The method of claim 4, wherein the IC50/μM for Aβ for the candidate compounds is from about 0.5 to about 5734, as determined by ThT functional aggregation assay.

6. The method according to claim 1, wherein the list of candidate compounds includes both the compound known to be active and analogs of said compound, and the score cutoff is that score which belongs to the compound known to be active.

7. The method of claim 1, wherein the structure of said amyloid protein model comprises two Aβ$_{17-42}$ monomers bound to each other near the N terminals, each monomer is folded in a loop from residues 23 through 33, and the loops are stabilized by intra-loop cationic-anionic interactions between Asp$_{23}$ and Lys$_{28}$.

8. The method of claim 1, wherein resveratrol can be bound in the pocket.

9. A method of using a computer molecular modeling program on a computer system for identifying compounds that modulate amyloid aggregation comprising the steps of:
using a computer molecular modeling program for constructing a non-crystallographic model of amyloid protein aggregation comprising a three-dimensional model of a monomeric amyloid peptide; and a three-dimensional model of an amyloid protein, wherein said amyloid peptide model is substantially SEQ ID: 1; said amyloid protein model is substantially SEQ ID: 2; and said amyloid protein model positioned with respect to said amyloid peptide model such that:
the amino acid Val at position 8 of SEQ ID: 1 interacts with the amino acid Glu at position 6 of SEQ ID: 2;
the amino acid Gly at position 9 of SEQ ID: 1 interacts with the amino acid Glu at position 6 of SEQ ID: 2;
the amino acid Ser at position 10 of SEQ ID: 1 interacts with the amino acid Gly at position 9 of SEQ ID: 2;
the amino acid Ser at position 10 of SEQ ID: 1 interacts with the amino acid Ser at position 10 of SEQ ID:2; and
the amino acid Lys at position 12 of SEQ ID: 1 interacts with the amino acid Glu at position 6 of SEQ ID: 2, and
a pocket is formed between said amyloid peptide model and said amyloid protein model;
constructing a candidate compound in a computer molecular modeling program;
docking the candidate compound into said pocket in the computer molecular modeling program and determining the candidate compound's degree of complementarity with respect to said pocket; and
using the determined degree of complementarity with respect to said pocket to determine whether the candidate compound is capable of modulating amyloid aggregation, wherein the compounds capable of modulating amyloid aggregation are output to be further evaluated experimentally as amyloid aggregation inhibitors.

10. The method of claim 9, further comprising determining the amyloid aggregation activity of the identified compounds in an in vitro assay.

11. The method of claim 10, wherein the in vitro assay is ThT assay.

12. The method of claim 9, wherein the amyloid protein is an amyloid oligomer or amyloidogenic fragment thereof comprising a region selected from the group consisting of approximately residues 17 through 40 of beta-amyloid protein of length 40 and approximately residues 17 through 42 of beta-amyloid protein of length 42.

13. The method of claim 9, wherein said amyloid peptide model and said amyloid protein model are both composed of beta-amyloid protein or an amyloid-forming fragment thereof.

14. The method of claim 9, wherein SEQ ID: 1 and SEQ ID: 2 interact in the manner depicted stereographically in FIG. 2 and form said packet, such that the candidate compound may be inserted into the pocket.

15. A method of using a computer molecular modeling program on a computer system for identifying compounds that modulate amyloid aggregation comprising the steps of:
using a computer molecular modeling program for constructing a non-crystallographic model of amyloid protein aggregation comprising a three-dimensional model of a monomeric amyloid peptide; and a three-dimensional model of an amyloid protein, said amyloid protein model positioned with respect to said amyloid peptide model such that a pocket is formed between said amyloid peptide model and said amyloid protein model in the computer molecular modeling program;

docking a candidate compound into said pocket, determining the candidate compound's degree of complementarity with respect to said pocket; and using the determined degree of complementarity with respect to said pocket to determine whether the candidate compound is capable of modulating amyloid aggregation, wherein compounds capable of modulating amyloid aggregation are output to be further evaluated experimentally as amyloid aggregation inhibitors;

wherein said amyloid peptide model is substantially SEQ ID: 1;

said amyloid protein model is substantially SEQ ID: 2; and during said docking, the amino acid Val at position 8 of SEQ ID: 1 interacts with the amino acid Glu at position 6 of SEQ ID: 2;

the amino acid Gly at position 9 of SEQ ID: 1 interacts with the amino acid Glu at position 6 of SEQ ID: 2;

the amino acid Ser at position 10 of SEQ ID: 1 interacts with the amino acid Gly at position 9 of SEQ ID: 2;

the amino acid Ser at position 10 of SEQ ID: 1 interacts with the amino acid Ser at position 10 of SEQ ID:2; and the amino acid Lys at position 12 of SEQ ID: 1 interacts with the amino acid Glu at position 6 of SEQ ID: 2.

* * * * *

```
                        SEQUENCE LISTING

<160> NUMBER OF SEQ ID NOS: 2

<210> SEQ ID NO 1
<211> LENGTH: 26
<212> TYPE: PRT
<213> ORGANISM: Unknown
<220> FEATURE:
<223> OTHER INFORMATION: peptide

<400> SEQUENCE: 1

Leu Val Phe Phe Ala Glu Asp Val Gly Ser Asn Lys Gly Ala Ile Ile
1               5                   10                  15

Gly Leu Met Val Gly Gly Val Val Ile Ala
            20                  25

<210> SEQ ID NO 2
<211> LENGTH: 26
<212> TYPE: PRT
<213> ORGANISM: unknown
<220> FEATURE:
<223> OTHER INFORMATION: peptide

<400> SEQUENCE: 2

Leu Val Phe Phe Ala Glu Asp Val Gly Ser Asn Lys Gly Ala Ile Ile
1               5                   10                  15

Gly Leu Met Val Gly Gly Val Val Ile Ala
            20                  25
```